US011492623B2

(12) United States Patent
Jadhav et al.

(10) Patent No.: US 11,492,623 B2
(45) Date of Patent: Nov. 8, 2022

(54) HEPATITIS B VIRUS (HBV) DSRNA AGENT COMPOSITIONS AND METHODS OF USE THEREOF

(71) Applicant: ALNYLAM PHARMACEUTICALS, INC., Cambridge, MA (US)

(72) Inventors: Vasant R. Jadhav, Cambridge, MA (US); Martin A. Maier, Cambridge, MA (US); Stuart Milstein, Cambridge, MA (US); Mark K. Schlegel, Cambridge, MA (US)

(73) Assignee: ALNYLAM PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 17/268,324

(22) PCT Filed: Aug. 12, 2019

(86) PCT No.: PCT/US2019/046142
§ 371 (c)(1),
(2) Date: Feb. 12, 2021

(87) PCT Pub. No.: WO2020/036862
PCT Pub. Date: Feb. 20, 2020

(65) Prior Publication Data
US 2021/0332365 A1    Oct. 28, 2021

Related U.S. Application Data

(60) Provisional application No. 62/718,314, filed on Aug. 13, 2018.

(51) Int. Cl.
*C12N 15/113* (2010.01)
*A61P 31/20* (2006.01)
*A61K 47/54* (2017.01)

(52) U.S. Cl.
CPC ........ *C12N 15/1131* (2013.01); *A61K 47/549* (2017.08); *A61P 31/20* (2018.01)

(58) Field of Classification Search
CPC ............ C12N 15/1131; C12N 2310/14; C12N 2310/322; A61K 31/713; A61P 45/06
See application file for complete search history.

(56) References Cited

U.S. PATENT DOCUMENTS 5,571,026 A    11/1996 Kahre
5,604,118 A    2/1997 Giri et al.
(Continued)

FOREIGN PATENT DOCUMENTS

CN    1566131 A    1/2005
CN    1793359 A    6/2006
(Continued)

OTHER PUBLICATIONS

"AASLD Abstracts, Poster Session 4: Hepatitis B Therapy, *Hepatology* 60: 1088A-1128A, 2014."
(Continued)

*Primary Examiner* — Terra C Gibbs
(74) *Attorney, Agent, or Firm* — Seed IP Law Group LLP

(57) ABSTRACT

The present disclosure relates to double stranded RNA agents targeting the hepatitis B virus (HBV) genome, and methods of using such agents to inhibit expression of one or more HBV genes and methods of treating subjects having an HBV infection or HBV-associated disorder, e.g., chronic hepatitis B infection.

36 Claims, 4 Drawing Sheets

Specification includes a Sequence Listing.

(56) References Cited

U.S. PATENT DOCUMENTS

| | | |
|---|---|---|
| 5,610,050 A | 3/1997 | Blum et al. |
| 5,629,153 A | 5/1997 | Urdea |
| 5,843,770 A | 12/1998 | Ill et al. |
| 5,981,274 A | 11/1999 | Tyrrell et al. |
| 5,994,517 A | 11/1999 | Ts'o et al. |
| 5,998,203 A | 12/1999 | Matulic-Adamic et al. |
| 6,001,990 A | 12/1999 | Wands et al. |
| 6,057,153 A | 5/2000 | George et al. |
| 6,287,770 B1 | 9/2001 | Weston et al. |
| 6,503,533 B1 | 1/2003 | Korba et al. |
| 6,518,417 B1 | 2/2003 | Sczakiel et al. |
| 6,558,954 B1 | 5/2003 | Takle et al. |
| 6,573,048 B1 | 6/2003 | Atta et al. |
| 6,906,182 B2 | 6/2005 | Ts'o et al. |
| 7,109,165 B2 | 9/2006 | Matulic-Adamic et al. |
| 7,491,805 B2 | 2/2009 | Vargeese et al. |
| 7,829,691 B2 | 11/2010 | Anthony et al. |
| 7,985,581 B2 | 7/2011 | Pachuk et al. |
| 7,989,612 B2 | 8/2011 | McSwiggen et al. |
| 8,350,021 B2 | 1/2013 | Pachuk et al. |
| 8,450,467 B2 | 5/2013 | Manoharan et al. |
| 8,575,327 B2 | 11/2013 | Pachuk et al. |
| 8,598,334 B2 | 12/2013 | Hamatake |
| 8,618,277 B2 | 12/2013 | Beigelman et al. |
| 8,648,185 B2 | 2/2014 | McSwigen et al. |
| 8,809,293 B2 | 8/2014 | Chin et al. |
| 9,029,341 B2 | 5/2015 | Bartz et al. |
| 9,034,841 B2 | 5/2015 | Swayze et al. |
| 9,200,281 B2 | 12/2015 | Pachuk et al. |
| 9,352,048 B2 | 5/2016 | Manoharan et al. |
| 9,464,290 B2 | 10/2016 | Bartz et al. |
| 9,879,262 B2 | 1/2018 | Bartz et al. |
| 9,982,263 B2 | 5/2018 | Pachuk et al. |
| 10,407,682 B2 | 9/2019 | Bartz et al. |
| 10,513,703 B2 | 12/2019 | Hinkle et al. |
| 10,662,428 B2 | 5/2020 | Beigelman et al. |
| 10,793,860 B2 | 10/2020 | Bartz et al. |
| 10,982,212 B2 | 4/2021 | Pachuk et al. |
| 11,060,091 B2 | 7/2021 | Hinkle et al. |
| 2002/0086356 A1 | 7/2002 | Tuschl et al. |
| 2002/0155124 A1 | 10/2002 | Sallberg et al. |
| 2003/0083294 A1 | 5/2003 | Sullenger et al. |
| 2003/0087855 A1 | 5/2003 | Ward et al. |
| 2003/0143732 A1 | 7/2003 | Fosnaugh et al. |
| 2003/0148928 A1 | 8/2003 | Beigelman et al. |
| 2003/0190659 A1 | 10/2003 | LaCasse et al. |
| 2003/0206887 A1 | 11/2003 | Morrissey et al. |
| 2004/0091457 A1 | 5/2004 | John et al. |
| 2004/0110296 A1 | 6/2004 | Vargeese et al. |
| 2004/0180351 A1 | 9/2004 | Giese et al. |
| 2004/0235775 A1 | 11/2004 | Kung et al. |
| 2004/0259247 A1 | 12/2004 | Tuschl et al. |
| 2005/0020521 A1 | 1/2005 | Rana |
| 2005/0080246 A1 | 4/2005 | Allerson et al. |
| 2006/0148740 A1 | 7/2006 | Platenburg |
| 2006/0275762 A1 | 12/2006 | Saigo et al. |
| 2007/0027099 A1 | 2/2007 | Lin et al. |
| 2007/0031844 A1 | 2/2007 | Khvorova et al. |
| 2009/0325297 A1 | 12/2009 | Tian et al. |
| 2010/0145038 A1 | 6/2010 | McSwiggen et al. |
| 2013/0005793 A1 | 1/2013 | Chin et al. |
| 2015/0374844 A1 | 12/2015 | Degrade et al. |
| 2018/0008724 A1 | 1/2018 | Rajeev et al. |
| 2018/0037886 A1 | 2/2018 | Bettencourt et al. |
| 2019/0233821 A1 | 8/2019 | Beigelman et al. |
| 2020/0038506 A1 | 2/2020 | Sepp-Lorenzino et al. |

FOREIGN PATENT DOCUMENTS

| | | |
|---|---|---|
| CN | 101314047 A | 12/2008 |
| CN | 101322847 A | 12/2008 |
| CN | 101603042 A | 12/2009 |
| CN | 101948827 A | 1/2011 |
| CN | 102559657 A | 7/2012 |
| CN | 103014045 A | 4/2013 |
| CN | 103275971 A | 9/2013 |
| CN | 103333890 A | 10/2013 |
| EP | 0 957 107 A1 | 11/1999 |
| EP | 1 591 524 A1 | 11/2005 |
| EP | 2 071 030 A2 | 6/2009 |
| JP | 7-303485 A | 11/1995 |
| JP | 2002-335968 A | 11/2002 |
| WO | 90/12096 A1 | 10/1990 |
| WO | 95/27788 A1 | 10/1995 |
| WO | 97/33991 A1 | 9/1997 |
| WO | 98/28004 A1 | 7/1998 |
| WO | 99/13886 A1 | 3/1999 |
| WO | 99/52932 A1 | 10/1999 |
| WO | 99/65925 A1 | 12/1999 |
| WO | 00/44914 A1 | 8/2000 |
| WO | 01/38498 A2 | 5/2001 |
| WO | 01/40279 A2 | 6/2001 |
| WO | 01/75164 A2 | 10/2001 |
| WO | 02/072763 A2 | 9/2002 |
| WO | 02/085908 A1 | 10/2002 |
| WO | 02/094185 A2 | 11/2002 |
| WO | 03/006477 A1 | 1/2003 |
| WO | 03/050308 A1 | 6/2003 |
| WO | 03/070918 A2 | 8/2003 |
| WO | 03/074654 A2 | 9/2003 |
| WO | 2004/011624 A2 | 2/2004 |
| WO | 2004/024757 A2 | 3/2004 |
| WO | 2004/045543 A2 | 6/2004 |
| WO | 2004/063375 A1 | 7/2004 |
| WO | 2004/078181 A1 | 9/2004 |
| WO | 2004/080406 A2 | 9/2004 |
| WO | 2004/090108 A2 | 10/2004 |
| WO | 2004/094595 A2 | 11/2004 |
| WO | 2005/014806 A2 | 2/2005 |
| WO | 2006/020768 A2 | 2/2006 |
| WO | 2006/033756 A2 | 3/2006 |
| WO | 2006/069064 A2 | 6/2006 |
| WO | 2006/078278 A2 | 7/2006 |
| WO | 2007/022369 A2 | 2/2007 |
| WO | 2007/032794 A2 | 3/2007 |
| WO | 2007/054279 A2 | 5/2007 |
| WO | 2008/103276 A2 | 8/2008 |
| WO | 2010/080724 A1 | 7/2010 |
| WO | 2011/047312 A1 | 4/2011 |
| WO | 2012/024170 A2 | 2/2012 |
| WO | 2012/145697 A1 | 10/2012 |
| WO | 2013/003520 A1 | 1/2013 |
| WO | 2013/074974 A2 | 5/2013 |
| WO | 2013/075035 A1 | 5/2013 |
| WO | 2013/155204 A2 | 10/2013 |
| WO | 2014/179627 A2 | 11/2014 |
| WO | 2016/077321 A1 | 5/2016 |
| WO | 2017/027350 A2 | 2/2017 |
| WO | 2017/121791 A1 | 7/2017 |
| WO | 2018/027106 A2 | 2/2018 |
| WO | 2018/195165 A1 | 10/2018 |

OTHER PUBLICATIONS

"EASL 2017 Clinical Practice Guidelines on the management of hepatitis B virus infection," *Journal of Hepatology* 67:370-398, 2017.

Al-Mahtab et al., "Therapeutic potential of a combined hepatitis B virus surface and core antigen vaccine in patients with chronic hepatitis B," *Hepatol. Int.* 7:981-989, 2013.

Amarzguioui et al., "Tolerance for mutations and chemical modifications in a siRNA" *Nucl. Acids. Res.* 31(2):589-595, 2003.

Andino, "RNAi puts a lid on virus replication," *Nature Biotechnology* 21(6):629-630, 2003.

Australian Search Report, dated Oct. 12, 2006, for Singaporean Application No. 200507781-3, 7 pages.

Australian Written Opinion, dated Oct. 12, 2006, for Singaporean Application No. 200507781-3, 6 pages.

Backes et al., "Protein-prime/modified vaccinia virus Ankara vector-boost vaccination overcomes tolerance in high-antigenemic HBV-transgenic mice," *Vaccine* 34(7):923-932, 2016.

Bertoletti et al., "Adaptive immunity in HBV infection," *Journal of Hepatology* 64(1):S71-S83, 2016.

(56) References Cited

OTHER PUBLICATIONS

Bertrand et al., "Comparison of antisense oligonucleotides and siRNAs in cell culture and in vivo," *BBRC* 296:1000-1004, 2002.
Biessen et al., "Synthesis of Cluster Galactosides with High Affinity for the Hepatic Asialoglycoprotein Receptor," *J. Med. Chem.* 38(9):1538-1546, 1995.
Biessen et al., "The Cholesterol Derivative of a Triantennary Galactoside with High Affinity for the Hepatic Asialoglycoprotein Receptor: a Potent Cholesterol Lowering Agent," *J. Med. Chem.* 38(11):1846-1852, 1995.
Braasch et al., "Novel antisense and peptide Nucleic Acid Strategies for Controlling Gene Expression," *Biochem.* 41(14):4503-4510, 2002.
Caplen et al., "Specific inhibition of gene expression by small double-stranded RNAs in invertebrate and vertebrate systems," *Proc. Natl. Acad. Sci.* 98(17):9742-9747, 2001.
Chen et al., "RNAi for treating Hepatitis B Viral Infection," *Pharmaceutical Research* 25(1):72-86, 2008.
Chi et al., "Comparison between Coexistence of HBV and HDV Infection and Simple HBV Infection," *Chinese Journal of Public Health* 13(4):254, 1997 (with English machine translation).
Chiu et al., "RNAi in Human Cells: Basic Structural and Functional Features of Small Interfering RNA," *Mol. Cell* 10:549-561, 2002.
Choi et al., "Targeting Cancer Cells with DNA-Assembled Dendrimers," *Cell Cycle* 4(5):669-671, 2005.
Chouteau et al., "A short N-proximal region in the large envelope protein harbors a Determinant That Contributes to the Species Specificity of Human Hepatitis B Virus," *Journal of Virology* 75(23):11565-11572, 2001.
Connolly et al., "Binding and Endocytosis of Cluster Glycosides by Rabbit Hepatocytes," *J. Biol. Chem.* 257(2):939-945, 1982.
Couzin, "Mini RNA Molecules Shield Mouse Liver From Hepatitis," *Science* 299:995, 2003. (2 pages).
Crossman Jr. et al., "Synthesis of some second-generation substrate analogues of early intermediates in the biosynthetic pathway of glycosylphosphatidylinositol membrane anchors," *Carbohydrate Research* 321(1-2):42-51, 1999.
Di Bisceglie, "Hepatitis B and Hepatocellular Carcinoma," *Hepatology* 49(5 Suppl):S56-S60, 2009 (NIH Public Access Author Manuscript, available in PMC Mar. 2, 2011)(10 pages).
Dubber et al., "Solid-Phase Synthesis of Multivalent Glycoconjugates on a DNA Synthesizer," *Bioconjugate Chem.* 14(1):239-246, 2003.
Elbashir et al., "Duplexes of 21-nucleotide RNAs mediate RNA interference in cultured mammalian cells," *Nature* 411:494-498, 2001.
Elbashir et al., "Functional anatomy of siRNA for mediating efficient RNAi in *Drosophila melanogaster* embryo lysate," *EMBO J.* 20(23):6877-6888, 2001.
Feitelson et al., "New Animal Models of Hepatitis B and C," *ILAR Journal* 42(2):127-138, 2001.
Flisiak et al., "siRNA drug development against hepatitis B virus infection," *Expert Opinion on Biological Therapy* 18(6):609-617, 2018.
Freier et al., "The ups and downs of nucleic acid duplex stability: structure-stability studies on chemically-modified DNA:RNA duplexes," *Nucl. Acids Res.* 25(22):4429-4443, 1997.
Fu et al., "Optimal design and validation of antiviral siRNA for targeting hepatitis B virus," *Acta Pharmacol Sin* 29(12):1522-1528, 2008.
Galibert et al., "Nucleotide sequence of the hepatitis B virus genome (subtype ayw) cloned in *E. coli,*" *Nature* 281:646-650, 1979.
GenBank: AFY08738.1, large S protein, partial [Hepatitis B virus], dated Jan. 31, 2013.
GenBank: AJR19223.1. core protein [Hepatitis B virus]. Dated Mar. 8, 2015.
Giladi et al., "Small Interfering RNA Inhibits Hepatitis B Virus Replication in Mice," *Mol. Ther.* 8(5):769-776, 2003.
Guo et al., "Construction of Folate-Conjugated pRNA of bacteriophage phi29 DNA packaging motor for delivery of chimeric siRNA to nasopharyngeal carcinoma cells," *Gene Ther.* 13(10):814-820, 2006 (NIH Public Access Author Manuscript, available in PMC Mar. 17, 2010)(14 pages).
Hamasaki et al., "Short interfering RNA-directed inhibition of hepatitis B virus replication," *FEBS Letters* 543(1-3):51-54, 2003.
Hamzavi et al., "Modulation of the Pharmacokinetic Properties of PNA: Preparation of Galactosyl, Mannosyl, Fucosyl, N-Acetylgalactosaminyl, and N-Acetylglucosaminyl Derivatives of Aminoethylglycine Peptide Nucleic Acid Monomers and Their Incorporation into PNA Oligomers," *Bioconjugate Chem.* 14:941-954, 2003.
Holen et al., "Positional effects of short interfering RNAs targeting the human coagulation trigger Tissue Factor," *Nucleic Acids Research* 30(8):1757-1766, 2002.
Holen T. et al., "Similar behavior of single-strand and double-strand siRNSs suggests they act through a common RNAi pathway," *Nucleic Acids Research* 31(9):2401-2407, 2003.
Hung et al., "Specific inhibition of gene expression and transactivation functions of hepatitis B virus X protein and c-myc by small interfering RNAs," *FEBS Letters* 560(1-3):210-214, 2004.
Ikeda et al., "Ligand-Targeted Delivery of Therapeutic siRNA," *Pharm. Res.* 23(8):1631-1640, 2006.
International Preliminary Report on Patentability, dated Jan. 7, 2007, for International Application No. PCT/US2004/019229, 6 pages.
International Search Report, dated Sep. 16, 2005, for International Application No. PCT/US2004/019229, 8 pages.
Janas et al., "Selection of GalNAc-conjugated siRNAs with limited off-target-driven rat hepatotoxicity," *Nature Communications* 9(723):1-10, 2018.
Kapadia et al., "Interference of hepatitis C virus RNA replication by short interfering RNAs," *Proceedings of the National Academy of Sciences of the USA* 100(4):2014-2018, 2003.
Karskela et al., "Synthesis and Cellular Uptake of Fluorescently Labeled Multivalent Hyaluronan Disaccharide Conjugates of Oligonucleotide Phosphorothioates," *Bioconjugate Chem.* 19(12):2549-2558, 2008.
Katajisto et al., "An Aminooxy-Functionalized Non-Nucleosidic Phosphoramidite for the Construction of Multiantennary Oligonucleotide Glycoconjugates on a Solid Support," *Current Protocols in Nucleic Acid Chemistry* 21(1):4.26.1-4.26.16, 2005.
Katajisto et al., "Solid-Phase Synthesis of Multiantennary Oligonucleotide Glycoconjugates Utilizing on-Support Oximation," *Bioconjugate Chem.* 15(4):890-896, 2004.
Katajisto et al., "Solid-Phase Synthesis of Oligonucleotide Glycoconjugates Bearing Three Different Glycosyl Groups: Orthogonally Protected Bis(hydroxymethyl)-N,N'-bis(3-hydroxypropyl)malondiamide Phosphoramidite as Key Building Block," *J. Org. Chem.* 69(22):7609-7615, 2004.
Kim et al., "Increased in vivo immunological potency of HB-110, a novel therapeutic HBV DNA vaccine, by electroporation," *Experimental and Molecular Medicine* 40(6):669-676, 2008.
Krapcho et al., "Mono-Protected Diamines. N-tert-Butoxycarbonyl-α, ω-Alkanediamines From α, ω-Alkanediamines," *Synthetic Communications* 20(16):2559-2564, 1990.
Li et al., "Folate-Mediated Targeting of Antisense Oligodeoxynucleotides to Ovarian Cancer Cells," *Pharm. Res.* 15(10):1540-1545, 1998.
Li et al., "siRNA Combinations Mediate Greater Suppression of Hepatitis B virus Replication in Mice," *Cell Biochemistry and Biophysics* 69(3):641-647, 2014.
Liang, "Hepatitis B: The Virus and Disease," *Hepatology* 49(Suppl 5):S13-S21, 2009 (NIH Public Access Author Manuscript, available in PMC Jan. 20, 2010)(17 pages).
Liu et al., "Targeted Drug Delivery to Chemoresistant Cells: Folic Acid Derivatization of FdUMP[10] Enhances Cytotoxicity toward 5-FU-Resistant Human Colorectal Tumor Cells," *J. Org. Chem.* 66(17):5655-5663, 2001.
Lv et al., "RNA Interference Inhibitis Hepatitis B Virus Gene," *Progress in Modern Biomedicine* 11(23):4569-4572, 2011 (with English abstract).
Mahato et al., "Modulation of gene expression by antisense and antigene oligodeoxynucleotides and small interfering RNA," *Expert Opin. Drug Deliv.* 2(1):3-28, 2005.

(56) References Cited

OTHER PUBLICATIONS

Mahato et al., "Physicochemical and Disposition Characteristics of Antisense Oligonucleotides Complexed with Glycosylated Poly(L-lysine)," *Biochem. Pharmacol.* 53:887-895, 1997.
Maier et al., "Synthesis of Antisense Oligonucleotides Conjugated to a Multivalent Carbohydrate Cluster for Cellular Targeting," *Bioconjugate Chem.* 14:18-29, 2003.
Manoharan, "GalNAc-siRNA with Enhanced Stabilization Chemistry: ESC-GalNAc-siRNA," TIDES: Oligonucleotide and Peptide Research, Technology and Product Development, May 14, 2014, URL=http://www.alnylam.com/web/assets/ALNY-ESC-GalNAc-siRNA-TIDES-May2014-Capella.pdf, download date Feb. 2, 2016, 28 pages.
McCafferey et al., "Inhibition of hepatitis B virus in mice by RNA interference," *Nature Biotechnology* 21(6):639-644, 2003 (Supplemental Online Data (1)), retrieved from the Internet: https://media.nature.com/original/nature-assets/nbt/journal/v21/n6/extref/nbt824-S1.pdf (1 page).
McCafferey et al., "Inhibition of hepatitis B virus in mice by RNA interference," *Nature Biotechnology* 21(6):639-644, 2003 (Supplemental Online Data (2)), retrieved from the Internet: https://media.nature.com/original/nature-assets/nbt/journal/v21/n6/extref/nbt824-S2.pdf (2 pages).
McCaffrey et al., "Inhibition of hepatitis B vims in mice by RNA interference," *Nature Biotechnology* 21(6):639-644, 2003.
McCaffrey et al., "RNA interference in adult mice," *Nature* 418(6893):38-39, 2002.
Meyers, "RNAi Roundtable: Advances in Delivery of RNAi Therapeutics with Enhanced Stabilization Chemistry (ESC)-GalNAc-siRNA Conjugates," Jul. 22, 2014, URL=http://www.alnylam.com/web/assets/Roundtable_ESC-GalNAc-Conjugates_072214.pdf, download date Feb. 2, 2016, 40 pages.
Michler et al., "Combinatorial RNAi/vaccination therapy for chronic hepatitis B achieves long-term functional cure in preclinical mouse model," *Journal of Hepatology* 68(Supp 1):S16, 2018.
Michler et al., "Preclinical study of a combinatorial RNAi/vaccination therapy as a potential cure for chronic hepatitis B," *Journal of Hepatology* 66(1):S112, 2017.
Murata et al., "Design of quaternary chitosan conjugate having antennary galactose residues as a gene delivery tool," *Carbohydrate Polymers* 32(2):105-109, 1997.
Nair et al., "Multivalent N-Acetylgalactosamine-Conjugated siRNA Localizes in Hepatocytes and Elicits Robust RNAi-Mediated Gene Silencing," *J. Am. Chem. Soc.* 136:16958-16961, 2014.
Nassal, "HBV cccDNA: viral persistence reservoir and key obstacle for a cure of chronic hepatitis B," *Gut* 64:1972-1984, 2015.
Okamoto et al., "Full-Length Sequence of a Hepatitis C Virus Genome Having Poor Homology to Reported Isolates: Comparative Study of Four Distinct Genotypes," *Virology* 188(1):331-341, 1992.
Okamoto et al., "Hepatitus B virus, complete genome," NCBI GenBank NC_003977.1, URL=https://www.ncbi.nlm.nih.gov/nuccore/21326584, accessed Mar. 1, 2021 (3 pages).
Olie et al., "Analysis of ribosyl-modified, mixed backbone analogs of a bcl-2/bcl-xL antisense oligonucleotide," *Biochim. Biophys. Acta* 1576(1-2):101-109, 2002.
Parrish et al., "Functional Anatomy of a dsRNA Trigger: Differential Requirement for the Two Trigger Strands in RNA interference," *Mol. Cell* 6:1077-1087, 2000.
Putlitz et al., "Antisense RNA Complementary to Hepatitis B Virus Specifically Inhibits Viral Replication," *Gastroenterology* 115:702-713, 1998.
Radhakrishnan et al., "RNA interference as a new strategy against viral hepatitis," *Virology* 323(2):173-181, 2004.
Randall et al., "Clearance of replicating hepatitis C virus replicon RNAs in cell culture by small interfering RNAs," *PNAS* 100(1):235-240, 2003.
Reid et al., "RNAi Roundtable: ALN-HBV in Development for the Treatment ofHepatitis B Virus (HBV) Infection," Jul. 29, 2014, URL=http://www.alnylam.com/web/assets/Roundtable_ALN-HBV_072914.pdf, download date Feb. 2, 2016, 56 pages.

Ren et al., "Changes in Innate and Permissive Immune Responses after HBV Transgenic Mouse Vaccination and ILong-Term-siRNA Treatment," *Plos One* 8(3):e51525, 2013 (13 pages).
Rensen et al., "Design and Synthesis of Novel N-Acetylgalactosamine-Terminated Glycolipids for Targeting of Lipoproteins to the Hepatic Asialoglycoprotein Receptor," *J. Med. Chem.* 47(23):5798-5808, 2004.
Schlegel et al., "Chirality Dependent Potency Enhancement and Structural Impact of Glycol Nucleic Acid Modification on siRNA," *J. Am. Chem. Soc.* 139(25): 8537-8546, 2017.
Seo et al., "Small Interfering RNA-Mediated Inhibition of Hepatitis C Virus Replication in the Human Hepatoma Cell Line Huh-7," *J. Virol.* 77(1):810-812, 2003.
Shlomai et al., "Inhibition of Hepatitis B Virus Expression and Replication by RNA Interference," *Hepatology* 37(4):764-770, 2003.
Sioud, "On the delivery of small interfering RNAs into mammalian cells," *Expert Opin. Drug Deliv.* 2(4):639-651, 2005.
Six et al., "An Efficient and Stereoselective Synthesis of 1,2-0-Dialkyl-3-0-$\beta$-D-Glycosyl-sn-Glycerols," *Tetrahedron Lett.* 24(12):1229-1232, 1983.
Six et al., "Influence of Carbohydrate Moities on Monolayer Properties of Dialkylglycerylletherglycosides, Simple Model Compounds of the Glycolipids of Halophilic Bacteria," *J. Colloid Interface Sci.* 93(1):109-114, 1983.
Sliedregt et al., "Design and Synthesis of Novel Amphiphilic Dendritic Galactosides for Selective Targeting of Liposomes to the Hepatic Asialoglycoprotein Receptor," *J. Med. Chem.* 42(4):609-618, 1999.
Sui et al., "A DNA vector-based RNAi technology to suppress gene expression in mammalian calls," *PNAS* 99(8):5515-5520, 2002.
Tuschl et al., "The siRNA user guide," Revised Aug. 26, 2001, URL=http://www.mpibpc.gwdg.de/abteilungen/100/105/sirna_u.html, download date Nov. 14, 2001, 5 pages.
Tuschl et al., "The siRNA user guide," Revised May 6, 2004, URL=http://diyhpl.us/~bryan/irc/protocol-online/protocol-cache/sirna.html, download date Oct. 10, 2018, 7 pages.
Vaino et al., "Synthesis of a $_D$-lactosyl cluster-nucleoside conjugate," *Chem. Commun.* 19:1871-1872, 1997.
Vitral et al., "The use of non-human primates as animal models for the study of hepatitis viruses," *Brazilian Journal of Medical and Biological Research* 31(8):1035-1048, 1998.
Wang et al., "Immunotherapeutic interventions in chronic hepatitis B virus infection: A review," *Journal of Immunological Methods* 407:1-8, 2014.
Wilson et al., "RNA interference blocks gene expression and RNA synthesis from hepatitis C replicons propagated in human liver cells," *Proceedings of the National Academy of Sciences of the USA* 100(5):2783-2788, 2003.
Wolfrum et al., "Mechanisms and optimization of in vivo delivery of lipophilic siRNAs," *Nature Biotechnology* 25(10):1149-1157, 2007.
Wong et al., "Lipid, Sugar and Liposaccharide Based Delivery Systems," *Curr. Med. Chem.* 8(9):1123-1136, 2001.
Yu et al., "The Role of Antiviral Therapy for HBV-Related Hepatocellular Carcinoma," *International Journal of Hepatology* 2011:416459, 2011, (9 pages).
Zatsepin et al., "Synthesis and Applications of Oligonucleotide-Carbohydrate Conjugates," *Chem. Biodivers.* 1(10):1401-1417, 2004.
Zhang et al., "RNA Interference inhibits Hepatitis B Virus of different genotypes in Vitro and in Vivo," *BMC Microbiology* 10:214, 2010 (10 pages).
Zhang et al., "Effects of Long-Term siRNA Treatment on the Immune System of HBV Transgene Mice," *Letters in Biotechnology* 2:217-220, 2014 (with English abstract).
Zheng et al., "Distribution and anti-HBV effects of antisense oligodeoxynu-cleotides conjugated to galactosylated poly-L-lysine," *World J. Gastroenterol.* 9(6):1251-1255, 2003.
Zimmermann et al., "RNAi-mediated gene silencing in non-human primates," *Nature* 441(7089):111-114, 2006.
Bramsen et al., "Chapter 5: Chemical Modification of Small Interfering RNA," in van Rij (ed.), *Antiviral RNAi: Concepts, Methods, and Applications*, Springer, New York, 2011, pp. 77-85 (16 pages).

(56) References Cited

OTHER PUBLICATIONS

Changhua et al., "Research progress of chemically modificed siRNA," *Int J Lab Med* 27(8):693-695, Aug. 2006 (with English Translation)(9 pages).

Chiu et al., "siRNA function in RNAi: A chemical modification analysis," *RNA* 9:1034-1048, 2003.

Huang-lei et al., "Chemical modifications of small interfering RNA: a research progress," *Journal of International Pharmaceutical Research* 35(6):419-424, Dec. 2008 (with English Translation)(17 pages).

Jagla et al., "Sequence characteristics of functional siRNAs," *RNA* 11:864-872, 2005.

Kanasty et al., "Delivery materials for siRNA therapeutics," *Nature Materials* 12:967-977, Nov. 2013.

Khvorova et al., "Functional siRNAs and miRNAs Exhibit Strand Bias," *Cell* 115:209-216, 2003.

Künne et al., "Planting the seed: target recognition of short guide RNAs," Trends in Microbiology 22(2):74-83, 2014.

Michler et al., "RNA Interference Mediated Suppression of HBV Transcripts Restores HBV-Specific Immunity and Enhances the Efficacy of Therapeutic Vaccination," *Journal of Hepatology* 64(2, Supplement):S148-S149, 2016.

Panjaworayan et al., "Effects of HBV Genetic Variability of RNAi Strategies," *Hepatitis Research and Treatment* 2011(367908):1-8, 2011.

Peacock et al., "Chemical Modification of siRNA Bases to Probe and Enhance RNA Interference," *J Org Chem.* 76(18):7295-7300, Sep. 2011 (NIH Public Access Author Manuscript, available in PMC Sep. 16, 2012)(13 pages).

Prakash et al., "Positional Effect of Chemical Modifications on Short Interference RNA Activity in Mammalian Cells," *J. Med. Chem.* 48:4247-4253, May 2005.

Rana, "Illuminating the silence: understanding the structure and function of small RNAs," *Nature Reviews* 8:23-36, Jan. 2007.

Reynolds et al., "Rational siRNA design for RNA interference," *Nature Biotechnology* 22(3):326-330, Mar. 2004.

Schwarz et al., "Asymmetry in the Assembly of the RNAi Enzyme Complex," *Cell* 115:199-208, 2003.

Somoza et al., "Steric Effects in RNA Interference: Probing the Influence of Nucleobase Size and Shape," *Chem. Eur. J.* 14:7978-7987, 2008.

Wei et al., "Designing of siRNAs," *J Int Pharm Res* 37(2):133-135, Apr. 2010. (with English Translation)(8 pages).

SEQUENCE LISTING

<160> NUMBER OF SEQ ID NOS: 49

<210> SEQ ID NO 1
<211> LENGTH: 3215
<212> TYPE: DNA
<213> ORGANISM: Hepatitis B virus
<220> FEATURE:
<223> OTHER INFORMATION: NC_003977.1, Hepatitis B virus, complete genome

<400> SEQUENCE: 1

```
ctccacaaca ttccaccaag ctctgctaga tcccagagtg aggggcctat attttcctgc      60
tggtggctcc agttccggaa cagtaaaccc tgttccgact actgcctcac ccatatcgtc     120
aatcttctcg aggactgggg accctgcacc gaacatggag agcacaacat caggattcct     180
aggacccctg ctcgtgttac aggcggggtt tttcttgttg acaagaatcc tcacaatacc     240
acagagtcta gactcgtggt ggacttctct caattttcta gggggagcac ccacgtgtcc     300
tggccaaaat tcgcagtccc caacctccaa tcactcacca acctcttgtc ctccaacttg     360
tcctggctat cgctggatgt gtctgcggcg ttttatcata ttcctcttca tcctgctgct     420
atgcctcatc ttcttgttgg ttcttctgga ctaccaaggt atgttgcccg tttgtcctct     480
acttccagga acatcaacta ccagcacggg accatgcaga acctgcacga ttcctgctca     540
aggaacctct atgtttccct cttgttgctg tacaaaacct tcggacggaa actgcacttg     600
tattcccatc ccatcatcct gggctttcgc aagattccta tgggagtggg cctcagtccg     660
tttctcctgg ctcagtttac tagtgccatt tgttcagtgg ttcgtagggc tttcccccac     720
tgtttggctt tcagctatat ggatgatgtg gtattggggg ccaagtctgt acaacatctt     780
gagtcccttt ttacctctat taccaatttt cttttgtctt gggtataca tttgaaccct     840
```

-continued

```
aataaaaccaa aacgttgggg ctactcccttt aacttcatgg gatatgtaat tggaagttgg      900
ggtactttac cgcaggaaca tattgtacaa aaactcaagc aatgttttcg aaaattgcct       960
gtaaatagac ctattgattg gaaagtatgt caaagaattg tgggtctttt gggctttgct      1020
gcccctttta cacaatgtgg ctatcctgcc ttgatgcctt tatatgcatg tatacaatct      1080
aagcaggctt tcactttctc gccaacttac aaggcctttc tgtgtaaaca atatctaaac      1140
ctttaccccg ttgcccggca acggtcaggt ctctgccaag tgtttgctga cgcaaccccc      1200
acgggttggg gcttggccat aggccatcgg cgcatgcgtg gaacctttgt ggctcctctg      1260
ccgatccata ctgcggaact cctagcagct tgttttgctc gcagccggtc tggagcgaaa      1320
cttatcggaa ccgacaactc agttgtcctc tctcggaaat acacctcctt tccatggctg      1380
ctaggctgtg ctgccaactg gatcctgcgc gggacgtcct ttgtctacgt cccgtcggcg      1440
ctgaatcccg cggacgaccc gtctcggggc cgtttgggcc tctaccgtcc ccttcttcat      1500
ctgccgttcc ggccgaccac ggggcgcacc tctctttacg cggtctcccc gtctgtgcct      1560
tctcatctgc cggaccgtgt gcacttcgct tcacctctgc acgtagcatg gagaccaccg      1620
tgaacgccca ccaggtcttg cccaaggtct tacacaagag gactcttgga ctctcagcaa      1680
tgtcaacgac cgaccttgag gcatacttca aagactgttt gtttaaagac tgggaggagt      1740
tgggggagga gattaggtta aaggtctttg tactaggagg ctgtaggcat aaattggtct      1800
gttcaccagc accatgcaac tttttcccct ctgcctaatc atctcatgtt catgtcctac      1860
tgttcaagcc tccaagctgt gccttgggtg gctttggggc atggacattg acccgtataa      1920
agaatttgga gcttctgtgg agttactctc ttttttgcct tctgacttct ttccttctat      1980
tcgagatctc ctcgacaccg cctctgctct gtatcgggag gccttagagt ctccggaaca      2040
ttgttcacct caccatacag cactcaggca agctattctg tgttggggtg agttgatgaa      2100
tctggccacc tgggtgggaa gtaatttgga agacccagca tccagggaat tagtagtcag      2160
ctatgtcaat gttaatatgg gcctaaaaat tagacaacta ttgtggtttc acatttcctg      2220
ccttactttt ggaagagaaa ctgtccttga gtatttggtg tcttttggag tgtggattcg      2280
cactcctccc gcttacagac caccaaatgc ccctatctta tcaacacttc cggaaactac      2340
tgttgttaga cgacgaggca ggtcccctag aagaagaact ccctcgcctc gcagacgaag      2400
gtctcaatcg ccgcgtcgca gaagatctca atctcgggaa tctcaatgtt agtatcccctt     2460
ggactcataa ggtgggaaac tttactgggc tttattcttc tactgtacct gtctttaatc      2520
ctgattggaa aactccctcc tttcctcaca ttcatttaca ggaggacatt attaatagat      2580
gtcaacaata tgtgggccct ctgacagtta atgaaaaaag gagattaaaa ttaattatgc      2640
ctgctaggtt ctatcctaac cttaccaaat atttgcccctt ggacaaaggc attaaaccgt      2700
attatcctga atatgcagtt aatcattact tcaaaactag gcattatttta catactctgt      2760
ggaaggctgg cattctatat aagagagaaa ctacacgcag cgcctcattt tgtgggtcac      2820
catattcttg ggaacaagag ctacagcatg ggaggttggt cttccaaacc tcgacaaggc      2880
atggggacga atctttctgt tcccaatcct ctgggattct ttcccgatca ccagttggac      2940
cctgcgttcg gagccaactc aaacaatcca gattgggact tcaaccccaa caaggatcac      3000
tggccagagg caaatcaggt aggagcggga gcatttggtc cagggttcac cccaccacac      3060
ggaggccttt tggggtggag ccctcaggct caggcatat tgacaacact gccagcagca      3120
cctcctcctg cctccaccaa tcggcagtca ggaagacagc ctactcccat ctctccacct      3180
ctaagagaca gtcatcctca ggccatgcag tggaa                                 3215
```

<210> SEQ ID NO 2
<211> LENGTH: 3215
<212> TYPE: DNA
<213> ORGANISM: Artificial Sequence
<220> FEATURE:
<223> OTHER INFORMATION: Reverse Complement of SEQ ID NO:1

<400> SEQUENCE: 2

```
ttccactgca tggcctgagg atgactgtct cttagaggtg gagagatggg agtaggctgt    60
cttcctgact gccgattggt ggaggcagga ggaggtgctg ctggcagtgt tgtcaatatg   120
ccctgagcct gagggctcca ccccaaaagg cctccgtgtg gtggggtgaa ccctggacca   180
aatgctcccg ctcctacctg atttgcctct ggccagtgat ccttgttggg gttgaagtcc   240
caatctggat tgtttgagtt ggctccgaac gcagggtcca actggtgatc gggaaagaat   300
cccagaggat tgggaacaga aagattcgtc cccatgcctt gtcgaggttt ggaagaccaa   360
cctcccatgc tgtagctctt gttcccaaga atatggtgac ccacaaaatg aggcgctgcg   420
tgtagtttct ctcttatata gaatgccagc cttccacaga gtatgtaaat aatgcctagt   480
tttgaagtaa tgattaactg catattcagg ataatacggt ttaatgcctt tgtccaaggg   540
caaatatttg gtaaggttag gatagaacct agcaggcata attaatttta atctcctttt   600
ttcattaact gtcagagggc ccacatattg ttgacatcta ttaataatgt cctcctgtaa   660
atgaatgtga ggaaaggagg gagttttcca atcaggatta aagacaggta cagtagaaga   720
ataaagccca gtaaagtttc ccaccttatg agtccaaggg atactaacat tgagattccc   780
gagattgaga tcttctgcga cgcggcgatt gagaccttcg tctgcgaggc gagggagttc   840
ttcttctagg ggacctgcct cgtcgtctaa caacagtagt ttccggaagt gttgataaga   900
taggggcatt tggtggtctg taagcgggag gagtgcgaat ccacactcca aaagacacca   960
aatactcaag gacagtttct cttccaaaag taaggcagga aatgtgaaac cacaatagtt  1020
gtctaatttt taggcccata ttaacattga catagctgac tactaattcc ctggatgctg  1080
ggtcttccaa attacttccc acccaggtgg ccagattcat caactcaccc aacacagaa   1140
tagcttgcct gagtgctgta tggtgaggtg aacaatgttc cggagactct aaggcctccc  1200
gatacagagc agaggcggtg tcgaggagat ctcgaataga aggaaagaag tcagaaggca  1260
aaaaagagag taactccaca gaagctccaa attctttata cgggtcaatg tccatgcccc  1320
aaagccaccc aaggcacagc ttggaggctt gaacagtagg acatgaacat gagatgatta  1380
ggcagagggg aaaagttgc atggtgctgg tgaacagacc aatttatgcc tacagcctcc  1440
tagtacaaag accttaacc taatctcctc ccccaactcc tcccagtctt taaacaaaca  1500
gtctttgaag tatgcctcaa ggtcggtcgt tgacattgct gagagtccaa gagtcctctt  1560
gtgtaagacc ttgggcaaga cctggtgggc gttcacggtg gtctccatgc tacgtgcaga  1620
ggtgaagcga agtgcacacg gtccggcaga tgagaaggca cagacgggga gaccgcgtaa  1680
agagaggtgc gccccgtggt cggccggaac ggcagatgaa gaagggacg gtagaggccc   1740
aaacggcccc gagacgggtc gtccgcggga ttcagcgccg acgggacgta gacaaaggac  1800
gtcccgcgca ggatccagtt ggcagcacag cctagcagcc atgaaaggga gtgtatttc   1860
cgagagagga caactgagtt gtcggttccg ataagtttcg ctccagaccg gctgcgagca  1920
aaacaagctg ctaggagttc gcagtatgg atcggcagag gagccacaaa ggttccacgc   1980
atgcgccgat ggcctatggc caagccccaa cccgtggggg ttgcgtcagc aaacacttgg  2040
```

-continued

```
cagagacctg accgttgccg ggcaacgggg taaaggttta gatattgttt acacagaaag    2100
gccttgtaag ttggcgagaa agtgaaagcc tgcttagatt gtatacatgc atataaaggc    2160
atcaaggcag gatagccaca ttgtgtaaaa ggggcagcaa agcccaaaag acccacaatt    2220
ctttgacata ctttccaatc aataggtcta tttacaggca attttcgaaa acattgcttg    2280 agttttgta caatatgttc ctgcggtaaa gtaccccaac ttccaattac atatcccatg     2340
aagttaaggg agtagcccca acgtttggtt ttattagggt tcaaatgtat acccaaagac    2400
aaaagaaaat tggtaataga ggtaaaaagg gactcaagat gttgtacaga cttggccccc    2460
aataccacat catccatata gctgaaagcc aaacagtggg ggaaagccct acgaaccact    2520
gaacaaatgg cactagtaaa ctgagccagg agaaacggac tgaggcccac tcccatagga    2580
atcttgcgaa agcccaggat gatgggatgg gaatacaagt gcagtttccg tccgaaggtt    2640
ttgtacagca acaagaggga aacatagagg ttccttgagc aggaatcgtg caggttctgc    2700
atggtcccgt gctggtagtt gatgttcctg gaagtagagg acaaacgggc aacatacctt    2760
ggtagtccag aagaaccaac aagaagatga ggcatagcag caggatgaag aggaatatga    2820
taaaacgccg cagacacatc cagcgatagc caggacaagt tggaggacaa gaggttggtg    2880
agtgattgga ggttggggac tgcgaatttt ggccaggaca cgtgggtgct cccctagaa     2940 aattgagaga agtccaccac gagtctagac tctgtggtat tgtgaggatt cttgtcaaca    3000
agaaaaaccc cgcctgtaac acgagcaggg gtcctaggaa tcctgatgtt gtgctctcca    3060
tgttcggtgc agggtcccca gtcctcgaga agattgacga tatgggtgag gcagtagtcg    3120
gaacagggtt tactgttccg gaactggagc caccagcagg aaaatatagg cccctcactc    3180
tgggatctag cagagcttgg tggaatgttg tggag                                3215
```

<210> SEQ ID NO 3
<211> LENGTH: 3215
<212> TYPE: DNA
<213> ORGANISM: Hepatitis B virus
<220> FEATURE:
<223> OTHER INFORMATION: AB014381.1, Hepatitis B virus genomic DNA, complete sequence, isolate 22Y04HCC
<220> FEATURE:
<221> NAME/KEY: misc_feature
<222> LOCATION: (1)...(3215)
<223> OTHER INFORMATION: n = A,T,C or G

<400> SEQUENCE: 3

```
ctccaccaca ttccaccaag ctctgctaca ccccagagta aggggcctat actttcctgc     60
tggtggctcc agttccggaa cagtaaaccc tgttccgact actgcctctc ccatatcgtc    120
aatcttctcg aggactgggg accctgcacc gaacatggag aacacaacat caggattcct    180
aggacccctg ctcgtgttac aggcggggtt tttcttgttg acaagaatcc tcacaatacc    240
acagagtcta gactcgtggt ggacttctct caattttcta ggggagcac ccacgtgtcc     300 tggccaaaat tcgcagtccc caacctccaa tcactcacca acctcttgtc ctccaatttg    360
tcctggctat cgctggatgt gtctgcggcg ttttatcata ttcctcttca tcctgctgct    420
atgcctcatc ttcttgttgg ttcttctgga ctaccaaggt atgttgcccg tttgtcctct    480
acttccagga acatcaacta ccagcacggg accatgcaag acctgcacga ttcctgctca    540
aggcacctct atgtttccct cttgttgctg tacaaaacct tcggacggaa actgcacttg    600
tattcccatc ccatcatcct gggctttcgc aagattccta tgggagtggg cctcagtccg    660
tttctcctgg ctcagtttac tagtgccatt tgttcagtgg ttcgtagggc tttcccccac    720
```

```
tgtttggctt tcagttatat ggatgatgtg gtattggggg ccaagtctgt acaacatctt    780
gagtcccttt ttaccgctgt taccaatttt cttttgtctt tgggtataca tttgaaccct    840
aataaaacca aacgttgggg ttactccctt aacttcatgg gatatgtaat tggaagttgg    900
ggtactttac cgcaagacca tattgtacta aaaatcaagc aatgttttcg aaaactgcct    960
gtaaatagac ctattgattg gaaagtatgt cagagaattg tgggtctttt gggctttgct   1020
gcccctttta cacaatgtgg ctatcctgcc ttaatgcctt tatatgcatg tatacaatct   1080
aagcaggctt tcactttctc gccaacttac aaggcctttc tgtgtaaaca atatctgaac   1140
ctttaccccg ttgcccggca acggtcaggt ctctgccaag tgtttgctga cgcaaccccc   1200
actggatggg gcttggctat tggccatcgc cgcatgcgtg aacctttgt ggctcctctg    1260
ccgatccata ctgcggaact cctagcagct tgttttgctc gcagccggtc tggagcgaaa   1320
ctgatcggaa cggacaactc tgttgttctc tctcggaaat acacctcctt tccatggctg   1380
ctagggtgtg ctgccaactg gatcctgcgc gggacgtcct ttgtttacgt cccgtcggcg   1440
ctgaatcccg cggacgaccc atctcggggc cgtttgggtc tctaccgtcc ccttcttcat   1500
ctgccgttcc ggccgaccac ggggcgcacc tctctttacg cggtctcccc gtctgtgcct   1560
tctcatctgc cggaccgtgt gcacttcgct tcacctctgc acgtcgcatg gagaccaccg   1620
tgaacgccca ccaggtcttg cccaaggtct tatataagag gactcttgga ctctcagcaa   1680
tgtcaacgac cgaccttgag gcatacttca aagactgttt gtttaaggac tgggaggagt   1740
tgggggagga gattaggtta atgatctttg tactaggagg ctgtaggcat aaattggtct   1800
gttcaccagc accatgcaac tttttcacct ctgcctaatc atctcatgtt catgtcctac   1860
tgttcaagcc tccaagctgt gccttgggtg gctttaggac atggacattg acccatataa   1920
agaatttgga gcttctgtgg agttactctc ttttttgcct tctgactttt ttccttctat   1980
tcgagatctc ctcgacaccg cctctgctct gtatcgggag gccttagagt ctccggaaca   2040
ttgttcacct caccatacag cactcagaca agccattctg tgttggggtg agttgatgaa   2100
tctggccacc tgggtgggaa gtaatttgga agacccagca tccagggaat tagtagtcag   2160
ctatgtcaat gttaatatgg gcctaaaaat cagacaacta ctgtggtttc acatttcctg   2220
tcttactttt ggaagagaaa ctgttcttga gtatttggtg tcttttggag tgtggattcg   2280
cactcctcct gcttacagac catcaaatgc ccctatctta tcaacacttc cggaaactac   2340
tgttgttaga cgacgaggca ggtcccctag aagaagaact ccctcgcctc gcagacgaag   2400
gtctcaatcg ccgcgtcgca gaagatctca atctcgggaa cctcaatgtt agtatcccct   2460
ggactcataa ggtgggaaac tttactgggc tttattcttc tactgtacct gtctttaatc   2520
ctgagtggca aactccctct tttcctcata ttcatttgca ggaggacatt attaatagat   2580
gtcaacaata tgtgggccct cttacagtta atgaaaaaag gagattaaaa ttaattatgc   2640
ctgctaggtt ctatcctaac cttaccaaat atttgccctt ggacaaaggc attaaaccat   2700
attatccgga acatgcagtt aatcattact tcaaaactag gcattattta catactctgt   2760
ggaaggcngg cattctatat aagagagaaa ctacacgcag cgcctcattt tgtgggtcac   2820
catattcttg gaacaagag ctacagcatg ggaggttggt cttccaaacc tcgacaaggc    2880
atgggacaa atctttctgt tcccaatcct ctgggattct ttcccgatca ccagttggac    2940
cctgcgttcg gagccaactc aaacaatcca gattgggact tcaacccaa caaggatcac    3000
tggccagagg caaatcaggt aggagcggga gcattcgggc cagggttcac cccaccacac   3060
ggcggtctttt tggggtggag ccctcaggct cagggcacat tgacaacagt gccagtagca   3120
```
cctcctcctg cctccaccaa tcggcagtca ggaagacagc ctactcccat ctctccacct    3180
ctaagagaca gtcatcctca ggccatgcag tggaa                              3215

<210> SEQ ID NO 4
<211> LENGTH: 3215
<212> TYPE: DNA
<213> ORGANISM: Artificial Sequence
<220> FEATURE:
<223> OTHER INFORMATION: Reverse Complement of SEQ ID NO:3
<220> FEATURE:
<221> NAME/KEY: misc_feature
<222> LOCATION: (1)...(3215)
<223> OTHER INFORMATION: n = A,T,C or G

<400> SEQUENCE: 4
ttccactgca tggcctgagg atgactgtct cttagaggtg gagagatggg agtaggctgt      60
cttcctgact gccgattggt ggaggcagga ggaggtgcta ctggcactgt tgtcaatgtg     120
ccctgagcct gagggctcca ccccaaaaga ccgccgtgtg gtgggtgaa ccctggcccg      180 aatgctcccg ctcctacctg atttgcctct ggccagtgat ccttgttggg gttgaagtcc    240
caatctggat tgtttgagtt ggctccgaac gcagggtcca actggtgatc gggaaagaat     300
cccagaggat tgggaacaga aagatttgtc cccatgcctt gtcgaggttt ggaagaccaa    360
cctcccatgc tgtagctctt gttcccaaga atatggtgac ccacaaaatg aggcgctgcg    420
tgtagtttct ctcttatata gaatgccngc cttccacaga gtatgtaaat aatgcctagt    480
tttgaagtaa tgattaactg catgttccgg ataatatggt ttaatgcctt tgtccaaggg    540
caaatatttg gtaaggttag gatagaacct agcaggcata attaatttta atctcctttt    600
ttcattaact gtaagagggc ccacatattg ttgacatcta ttaataatgt cctcctgcaa    660
atgaatatga ggaaaagagg gagtttgcca ctcaggatta aagacaggta cagtagaaga    720
ataaagccca gtaaagtttc ccaccttatg agtccaaggg atactaacat tgaggttccc    780
gagattgaga tcttctgcga cgcggcgatt gagaccttcg tctgcgaggc gagggagttc    840
ttcttctagg ggacctgcct cgtcgtctaa caacagtagt ttccggaagt gttgataaga    900
taggggcatt tgatggtctg taagcaggag gagtgcgaat ccacactcca aaagacacca    960
aatactcaag aacagtttct cttccaaaag taagacagga aatgtgaaac cacagtagtt   1020
gtctgatttt taggcccata ttaacattga catagctgac tactaattcc ctggatgctg   1080
ggtcttccaa attacttccc acccaggtgg ccagattcat caactcaccc caacacagaa   1140
tggcttgtct gagtgctgta tggtgaggtg aacaatgttc cggagactct aaggcctccc   1200
gatacagagc agaggcggtg tcgaggagat ctcgaataga aggaaaaaag tcagaaggca   1260
aaaaagagag taactccaca gaagctccaa attctttata tgggtcaatg tccatgtcct   1320
aaagccaccc aaggcacagc ttggaggctt gaacagtagg acatgaacat gagatgatta   1380
ggcagaggtg aaaagttgc atggtgctgg tgaacagacc aatttatgcc tacagcctcc    1440
tagtacaaag atcattaacc taatctcctc ccccaactcc tcccagtcct aaacaaaca    1500 gtctttgaag tatgcctcaa ggtcggtcgt tgacattgct gagagtccaa gagtcctctt   1560
atataagacc ttgggcaaga cctggtgggc gttcacggtg gtctccatgc gacgtgcaga   1620
ggtgaagcga agtgcacacg gtccggcaga tgagaaggca cagacgggga gaccgcgtaa   1680
agagaggtgc gccccgtggt cggccggaac ggcagatgaa gaaggggacg gtagagaccc   1740
aaacggcccc gagatgggtc gtccgcggga ttcagcgccg acggacgta aacaaaggac    1800

```
gtcccgcgca ggatccagtt ggcagcacac cctagcagcc atggaaagga ggtgtatttc    1860
cgagagagaa caacagagtt gtccgttccg atcagtttcg ctccagaccg gctgcgagca    1920
aaacaagctg ctaggagttc cgcagtatgg atcggcagag gagccacaaa ggttccacgc    1980
atgcggcgat ggccaatagc caagccccat ccagtggggg ttgcgtcagc aaacacttgg    2040
cagagacctg accgttgccg ggcaacgggg taaaggttca gatattgttt acacagaaag    2100
gccttgtaag ttggcgagaa agtgaaagcc tgcttagatt gtatacatgc atataaaggc    2160
attaaggcag gatagccaca ttgtgtaaaa ggggcagcaa agcccaaaag acccacaatt    2220
ctctgacata ctttccaatc aataggtcta tttacaggca gttttcgaaa acattgcttg    2280
atttttagta caatatggtc ttgcggtaaa gtaccccaac ttccaattac atatcccatg    2340
aagttaaggg agtaacccca acgtttggtt ttattagggt tcaaatgtat acccaaagac    2400
aaaagaaaat tggtaacagc ggtaaaaagg gactcaagat gttgtacaga cttggccccc    2460
aataccacat catccatata actgaaagcc aaacagtggg ggaaagccct acgaaccact    2520
gaacaaatgg cactagtaaa ctgagccagg agaaacggac tgaggcccac tcccatagga    2580
atcttgcgaa agcccaggat gatgggatgg gaatacaagt gcagtttccg tccgaaggtt    2640
ttgtacagca acaagaggga aacatagagg tgccttgagc aggaatcgtg caggtcttgc    2700
atggtcccgt gctggtagtt gatgttcctg gaagtagagg acaaacgggc aacatacctt    2760
ggtagtccag aagaaccaac aagaagatga ggcatagcag caggatgaag aggaatatga    2820
taaaacgccg cagacacatc cagcgatagc caggacaaat tggaggacaa gaggttggtg    2880
agtgattgga ggttggggac tgcgaatttt ggccaggaca cgtgggtgct cccccctagaa   2940 aattgagaga agtccaccac gagtctagac tctgtggtat tgtgaggatt cttgtcaaca    3000
agaaaaaccc cgcctgtaac acgagcaggg gtcctaggaa tcctgatgtt gtgttctcca    3060
tgttcggtgc agggtcccca gtcctcgaga agattgacga tatgggagag gcagtagtcg    3120
gaacagggtt tactgttccg gaactggagc caccagcagg aaagtatagg ccccttactc    3180
tggggtgtag cagagcttgg tggaatgtgg tggag                               3215
```

<210> SEQ ID NO 5
<211> LENGTH: 1200
<212> TYPE: DNA
<213> ORGANISM: Artificial Sequence
<220> FEATURE:
<223> OTHER INFORMATION: psiCHECK2-HBV plasmid

<400> SEQUENCE: 5

```
ctccacaaca ttccaccaag ctctgcaaga tcccagagtc aggggcctgt attttcctgc      60
tggtggctcc agttcaggaa cagtgaaccc tgttccgact attgcctctc ccatatcgtc     120
aatcttctcg aggactgggg accctgcacc gaacatggag aacatcacat caggattcct     180
aggacccctg ctcgtgttac aggcggggtt tttcttgttg acaaaaatcc tcacaatacc     240
acagagtcta gactcgtggt ggacttctct caattttcta gggggagcac ccgtgtgtcc     300
tggccaaaat tcgcagtccc caacctccaa tcactcacca acctcctgtc tccaacttg     360 tcctggctat cgttggatgt gtctgcggcg ttttatcatc ttcctcttca tcctgctgct     420
atgcctcatc ttcttgttgg ttcttctgga ctatcaaggt atgttgcccg tttgtcctct     480
aattccagga tcatcaacca ccagcacggg accatgcaaa acctgcacga ctcctgctca     540
aggaacctct atgtttccct catgttgctg tacaaaacct tcggacgaa attgcacctg      600 tattcccatc ccatcatctt gggctttcgc aaaataccta tgggagtggg cctcagtccg     660
```

```
tttctcttgg ctcagtttac tagtgccatt tgttcagtgg ttcgtagggc tttcccccac    720
tgtctggctt tcagttatat ggatgatgtg gtattggggg ccaagtctgt acagcatctt    780
gagtcccttt ataccgctgt taccaatttt cttttgtctt tgggtataca tttaaaccct    840
aacaaaacaa aaagatgggg ttattcccta aacttcatgg gttatgtaat tggaagttgg    900
gggacattgc cacaggaaca tattgtacaa aaaatcaaac aatgttttag aaaacttcct    960
gttaacaggc ctattgattg gaaagtatgt caacgaattg tgggtctttt gggctttgct   1020 gccccttta cacaatgtgg ttatcctgct taatgcctt tgtatgcatg tatacaagct   1080
aaacaggctt ttactttctc gccaacttac aaggcctttc tctgtaaaca atacatgaac   1140
ctttaccccg ttgctcggca acggccaggt ctgtgccaag tgtttgctga cgcaaccccc   1200
```

<210> SEQ ID NO 6
<211> LENGTH: 681
<212> TYPE: DNA
<213> ORGANISM: Hepatitis B virus
<220> FEATURE:
<223> OTHER INFORMATION: HBV, genotype A

<400> SEQUENCE: 6

```
atggagaaca tcacatcagg attcctagga cccctgctcg tgttacaggc ggggtttttc     60
ttgttgacaa gaatcctcac aataccgcag agtctagact cgtggtggac ttctctcaat    120
tttctagggg gatcacccgt gtgtcttggc caaaattcgc agtccccaac ctccaatcac    180
tcaccaacct cctgtcctcc aatttgtcct ggttatcgct ggatgtgtct gcggcgtttt    240
atcatattcc tcttcatcct gctgctatgc ctcatcttct tattggttct tctggattat    300
caaggtatgt tgcccgtttg tcctctaatt ccaggatcaa caacaaccag tacgggacca    360
tgcaaaacct gcacgactcc tgctcaaggc aactctatgt ttccctcatg ttgctgtaca    420
aaacctacgg atgaaattg cacctgtatt cccatcccat cgtcctgggc tttcgcaaaa    480
tacctatggg agtgggcctc agtccgtttc tcttggctca gtttactagt gccatttgtt    540
cagtggttcg tagggctttc ccccactgtt tggctttcag ctatatggat gatgtggtat    600
tgggggccaa gtctgtacag catcgtgagt cccttatac cgctgttacc aattttcttt    660
tgtctctggg tatacattta a                                              681
```

<210> SEQ ID NO 7
<211> LENGTH: 681
<212> TYPE: DNA
<213> ORGANISM: Hepatitis B virus
<220> FEATURE:
<223> OTHER INFORMATION: HBV, genotype C

<400> SEQUENCE: 7

```
atggagaaca caacatcagg attcctagga cccctgctcg tgttacaggc ggggtttttc     60
ttgttgacaa gaatcctcac aataccacag agtctagact cgtggtggac ttctctcaat    120
tttctagggg gagcacccac gtgtcctggc caaaattcgc agtccccaac ctccaatcac    180
tcaccaacct cttgtcctcc aatttgtcct ggctatcgct ggatgtgtct gcggcgtttt    240
atcatattcc tcttcatcct gctgctatgc ctcatcttct tgttggttct tctggactac    300
caaggtatgt tgcccgtttg tcctctactt ccaggaacat caactaccag cacgggacca    360
tgcaagacct gcacgattcc tgctcaagga acctctatgt ttccctcttg ttgctgtaca    420
aaaccttcgg acggaaactg cacttgtatt cccatcccat catcctgggc tttcgcaaga    480
```

```
ttcctatggg agtgggcctc agtccgtttc tcctggctca gtttactagt gccatttgtt    540
cagtggttcg tagggctttc ccccactgtt tggctttcag ttatatggat gatgtggtat    600
tgggggccaa gtctgtacaa catcttgagt ccctttttac ctctattacc aattttcttt    660
tgtctttggg tatacatttg a                                              681
```

```
<210> SEQ ID NO 8
<211> LENGTH: 681
<212> TYPE: DNA
<213> ORGANISM: Hepatitis B virus
<220> FEATURE:
<223> OTHER INFORMATION: HBV, genotype E

<400> SEQUENCE: 8
atggaaagca tcacatcagg attcctagga cccctgctcg tgttacaggc ggggtttttc     60
ttgttgacaa aaatcctcac aataccgcag agtctagact cgtggtggac ttctctcaat    120
tttctagggg gagctcccgt gtgtcttggc caaaattcgc agtccccaac ctccaatcac    180
tcaccaacct cttgtcctcc aatttgtcct ggctatcgct ggatgtgtct gcggcgtttt    240
atcatcttcc tcttcatcct gctgctatgc ctcatcttct tgttggttct tctggactat    300
caaggtatgt tgcccgtttg tcctctaatt ccaggatcat caaccaccag tacgggaccc    360
tgccgaacct gcacgactct tgctcaagga acctctatgt ttccctcatg ttgctgttca    420
aaaccttcgg acggaaattg cacttgtatt cccatcccat catcatgggc tttcggaaaa    480
ttcctatggg agtgggcctc agcccgtttc tcctggctca gtttactagt gccatttgtt    540
cagtggttcg ccgggctttc ccccactgtc tggctttcag ttatatggat gatgtggtat    600
tgggggccaa gtctgtacaa catcttgagt cccttttatac ctctgttacc aattttcttt    660
tgtctttggg tatacattta a                                              681
```

```
<210> SEQ ID NO 9
<211> LENGTH: 681
<212> TYPE: DNA
<213> ORGANISM: Hepatitis B virus
<220> FEATURE:
<223> OTHER INFORMATION: HBV, genotype F

<400> SEQUENCE: 9
atggacaaca tcacatcagg actcctagga cccctgctcg tgttacaggc ggtgtgtttc     60
ttgttgacaa aaatcctcac aataccacag agtctagact cgtggtggac ttctctcaat    120
tttctagggg gactacccgg gtgtcctggc caaaattcgc agtccccaac ctccaatcac    180
ttaccaacct cctgtcctcc aacttgtcct ggctatcgtt ggatgtgtct gcggcgtttt    240
atcatcttcc tcttcatcct gctgctatgc ctcatcttct tgttggttct tctggactat    300
caaggtatgt tgcccgtttg tcctctactt ccaggatcca cgaccaccag cacgggacca    360
tgcaaaacct gcacaactct tgctcaagga acctctatgt ttccctcctg ttgctgttcc    420
aaaccctcgg acggaaactg cacctgtatt cccatcccat catcttgggc tttaggaaaa    480 taccctatggg agtgggcctc agcccgtttc tcctggctca gtttactagt gcaatttgtt    540
cagtggtgcg tagggctttc ccccactgtc tggcttttag ttatatggat gatctggtat    600
tgggggccaa atctgtgcag catcttgagt cccttttatac cgctgttacc aattttctgt    660
tatctgtggg tatccattta a                                              681
```

```
<210> SEQ ID NO 10
<211> LENGTH: 19
```

```
<212> TYPE: RNA
<213> ORGANISM: Artificial Sequence
<220> FEATURE:
<223> OTHER INFORMATION: Synthetic oligonucleotide (sense)

<400> SEQUENCE: 10
gugugcacuu cgcuucaca                                                    19

<210> SEQ ID NO 11
<211> LENGTH: 19
<212> TYPE: DNA
<213> ORGANISM: Artificial Sequence
<220> FEATURE:
<223> OTHER INFORMATION: Synthetic oligonucleotide (sense)

<400> SEQUENCE: 11
gugugcactu cgcuucaca                                                    19

<210> SEQ ID NO 12
<211> LENGTH: 19
<212> TYPE: DNA
<213> ORGANISM: Artificial Sequence
<220> FEATURE:
<223> OTHER INFORMATION: Synthetic oligonucleotide (sense)

<400> SEQUENCE: 12
gugugcactu cgcuucaca                                                    19

<210> SEQ ID NO 13
<211> LENGTH: 21
<212> TYPE: RNA
<213> ORGANISM: Artificial Sequence
<220> FEATURE:
<223> OTHER INFORMATION: AD-66810 Antisense

<400> SEQUENCE: 13
ugugaagcga agugcacacu u                                                 21

<210> SEQ ID NO 14
<211> LENGTH: 21
<212> TYPE: RNA
<213> ORGANISM: Artificial Sequence
<220> FEATURE:
<223> OTHER INFORMATION: AD-192282 Antisense

<400> SEQUENCE: 14
ugugaagcga agugcacacu u                                                 21

<210> SEQ ID NO 15
<211> LENGTH: 21
<212> TYPE: RNA
<213> ORGANISM: Artificial Sequence
<220> FEATURE:
<223> OTHER INFORMATION: AD-192289 Antisense

<400> SEQUENCE: 15
ugugaagcga agugcacacu u                                                 21

<210> SEQ ID NO 16
<211> LENGTH: 21
<212> TYPE: RNA
<213> ORGANISM: Artificial Sequence
<220> FEATURE:
<223> OTHER INFORMATION: AD-81890 Antisense

<400> SEQUENCE: 16
```
ugugaagcga agugcacacu u                                              21

<210> SEQ ID NO 17
<211> LENGTH: 21
<212> TYPE: RNA
<213> ORGANISM: Artificial Sequence
<220> FEATURE:
<223> OTHER INFORMATION: AD-81892 Antisense

<400> SEQUENCE: 17
ugugaagcga agugcacacu u                                              21

<210> SEQ ID NO 18
<211> LENGTH: 21
<212> TYPE: RNA
<213> ORGANISM: Artificial Sequence
<220> FEATURE:
<223> OTHER INFORMATION: AD-192283 Antisense

<400> SEQUENCE: 18
ugugaagcga agugcacacu u                                              21

<210> SEQ ID NO 19
<211> LENGTH: 21
<212> TYPE: RNA
<213> ORGANISM: Artificial Sequence
<220> FEATURE:
<223> OTHER INFORMATION: AD-192291 Antisense

<400> SEQUENCE: 19
ugugaagcga agugcacacu u                                              21

<210> SEQ ID NO 20
<211> LENGTH: 21
<212> TYPE: RNA
<213> ORGANISM: Artificial Sequence
<220> FEATURE:
<223> OTHER INFORMATION: AD-192277 Antisense

<400> SEQUENCE: 20
ugugaagcga agugcacacu u                                              21

<210> SEQ ID NO 21
<211> LENGTH: 21
<212> TYPE: RNA
<213> ORGANISM: Artificial Sequence
<220> FEATURE:
<223> OTHER INFORMATION: AD-192284 Antisense

<400> SEQUENCE: 21
ugugaagcga agugcacacu u                                              21

<210> SEQ ID NO 22
<211> LENGTH: 21
<212> TYPE: RNA
<213> ORGANISM: Artificial Sequence
<220> FEATURE:
<223> OTHER INFORMATION: AD-192285 Antisense

<400> SEQUENCE: 22
ugugaagcga agugcacacu u                                              21

<210> SEQ ID NO 23
<211> LENGTH: 21
<212> TYPE: RNA
<213> ORGANISM: Artificial Sequence

```
<220> FEATURE:
<223> OTHER INFORMATION: AD-192293 Antisense

<400> SEQUENCE: 23
ugugaagcga agugcacacu u                                              21

<210> SEQ ID NO 24
<211> LENGTH: 21
<212> TYPE: RNA
<213> ORGANISM: Artificial Sequence
<220> FEATURE:
<223> OTHER INFORMATION: AD-192279 Antisense

<400> SEQUENCE: 24
ugugaagcga agugcacacu u                                              21

<210> SEQ ID NO 25
<211> LENGTH: 21
<212> TYPE: RNA
<213> ORGANISM: Artificial Sequence
<220> FEATURE:
<223> OTHER INFORMATION: AD-192294 Antisense

<400> SEQUENCE: 25
ugugaagcga agugcacacu u                                              21

<210> SEQ ID NO 26
<211> LENGTH: 21
<212> TYPE: RNA
<213> ORGANISM: Artificial Sequence
<220> FEATURE:
<223> OTHER INFORMATION: AD-192280 Antisense

<400> SEQUENCE: 26
ugugaagcga agugcacacu u                                              21

<210> SEQ ID NO 27
<211> LENGTH: 21
<212> TYPE: RNA
<213> ORGANISM: Artificial Sequence
<220> FEATURE:
<223> OTHER INFORMATION: AD-192287 Antisense

<400> SEQUENCE: 27
ugugaagcga agugcacacu u                                              21

<210> SEQ ID NO 28
<211> LENGTH: 21
<212> TYPE: RNA
<213> ORGANISM: Artificial Sequence
<220> FEATURE:
<223> OTHER INFORMATION: AD-192281 Antisense

<400> SEQUENCE: 28
ugugaagcga agugcacacu u                                              21

<210> SEQ ID NO 29
<211> LENGTH: 19
<212> TYPE: RNA
<213> ORGANISM: Artificial Sequence
<220> FEATURE:
<223> OTHER INFORMATION: Synthetic oligonucleotide (sense)

<400> SEQUENCE: 29
gugugcacuu cgcuucaca                                                 19
```

<210> SEQ ID NO 30
<211> LENGTH: 19
<212> TYPE: DNA
<213> ORGANISM: Artificial Sequence
<220> FEATURE:
<223> OTHER INFORMATION: Synthetic oligonucleotide (sense)

<400> SEQUENCE: 30
gugugcactu cgcuucaca                                                    19

<210> SEQ ID NO 31
<211> LENGTH: 19
<212> TYPE: DNA
<213> ORGANISM: Artificial Sequence
<220> FEATURE:
<223> OTHER INFORMATION: Synthetic oligonucleotide (sense)

<400> SEQUENCE: 31
gugugcactu cgcuucaca                                                    19

<210> SEQ ID NO 32
<211> LENGTH: 832
<212> TYPE: PRT
<213> ORGANISM: Hepatitis B virus
<220> FEATURE:
<223> OTHER INFORMATION: HBV P protein (YP_009173866)

<400> SEQUENCE: 32

```
Met Pro Leu Ser Tyr Gln His Phe Arg Arg Leu Leu Leu Leu Asp Asp
1               5                   10                  15

Glu Ala Gly Pro Leu Glu Glu Glu Leu Pro Arg Leu Ala Asp Glu Gly
            20                  25                  30

Leu Asn Arg Arg Val Ala Glu Asp Leu Asn Leu Gly Asn Leu Asn Val
        35                  40                  45

Ser Ile Pro Trp Thr His Lys Val Gly Asn Phe Thr Gly Leu Tyr Ser
    50                  55                  60

Ser Thr Val Pro Val Phe Asn Pro His Trp Lys Thr Pro Ser Phe Pro
65                  70                  75                  80

Asn Ile His Leu His Gln Asp Ile Ile Lys Lys Cys Glu Gln Phe Val
                85                  90                  95

Gly Pro Leu Thr Val Asn Glu Lys Arg Arg Leu Gln Leu Ile Met Pro
            100                 105                 110

Ala Arg Phe Tyr Pro Lys Val Thr Lys Tyr Leu Pro Leu Asp Lys Gly
        115                 120                 125

Ile Lys Pro Tyr Tyr Pro Glu His Leu Val Asn His Tyr Phe Gln Thr
    130                 135                 140

Arg His Tyr Leu His Thr Leu Trp Lys Ala Gly Ile Leu Tyr Lys Arg
145                 150                 155                 160

Glu Thr Thr His Ser Ala Ser Phe Cys Gly Ser Pro Tyr Ser Trp Glu
                165                 170                 175

Gln Asp Leu Gln His Gly Ala Glu Ser Phe His Gln Gln Ser Ser Gly
            180                 185                 190

Ile Leu Ser Arg Pro Pro Val Gly Ser Ser Leu Gln Ser Lys His Arg
        195                 200                 205

Lys Ser Arg Leu Gly Leu Gln Ser Gln Gln Gly His Leu Ala Arg Arg
    210                 215                 220

Gln Gln Gly Arg Ser Trp Ser Ile Arg Ala Gly Phe His Pro Thr Ala
225                 230                 235                 240
```

Arg Arg Pro Phe Gly Val Glu Pro Ser Gly Ser Gly His Thr Thr Asn
            245                 250                 255

Phe Ala Ser Lys Ser Ala Ser Cys Leu His Gln Ser Pro Val Arg Lys
        260                 265                 270

Ala Ala Tyr Pro Ala Val Ser Thr Phe Glu Lys His Ser Ser Ser Gly
            275                 280                 285

His Ala Val Glu Phe His Asn Leu Pro Pro Asn Ser Ala Arg Ser Gln
        290                 295                 300

Ser Glu Arg Pro Val Phe Pro Cys Trp Trp Leu Gln Phe Arg Asn Ser
305                 310                 315                 320

Lys Pro Cys Ser Asp Tyr Cys Leu Ser Leu Ile Val Asn Leu Leu Glu
            325                 330                 335

Asp Trp Gly Pro Cys Ala Glu His Gly Glu His His Ile Arg Ile Pro
        340                 345                 350

Arg Thr Pro Ser Arg Val Thr Gly Gly Val Phe Leu Val Asp Lys Asn
            355                 360                 365

Pro His Asn Thr Ala Glu Ser Arg Leu Val Val Asp Phe Ser Gln Phe
        370                 375                 380

Ser Arg Gly Asn Tyr Arg Val Ser Trp Pro Lys Phe Ala Val Pro Asn
385                 390                 395                 400

Leu Gln Ser Leu Thr Asn Leu Leu Ser Ser Asn Leu Ser Trp Leu Ser
            405                 410                 415

Leu Asp Val Ser Ala Ala Phe Tyr His Leu Pro Leu His Pro Ala Ala
        420                 425                 430

Met Pro His Leu Leu Val Gly Ser Ser Gly Leu Ser Arg Tyr Val Ala
            435                 440                 445

Arg Leu Ser Ser Asn Ser Arg Ile Leu Asn Asn Gln His Gly Thr Met
450                 455                 460

Pro Asp Leu His Asp Tyr Cys Ser Arg Asn Leu Tyr Val Ser Leu Leu
465                 470                 475                 480

Leu Leu Tyr Gln Thr Phe Gly Arg Lys Leu His Leu Tyr Ser His Pro
            485                 490                 495

Ile Ile Leu Gly Phe Arg Lys Ile Pro Met Gly Val Gly Leu Ser Pro
        500                 505                 510

Phe Leu Leu Ala Gln Phe Thr Ser Ala Ile Cys Ser Val Val Arg Arg
        515                 520                 525

Ala Phe Pro His Cys Leu Ala Phe Ser Tyr Met Asp Asp Val Val Leu
        530                 535                 540

Gly Ala Lys Ser Val Gln His Leu Glu Ser Leu Phe Thr Ala Val Thr
545                 550                 555                 560

Asn Phe Leu Leu Ser Leu Gly Ile His Leu Asn Pro Asn Lys Thr Lys
            565                 570                 575

Arg Trp Gly Tyr Ser Leu Asn Phe Met Gly Tyr Val Ile Gly Cys Tyr
        580                 585                 590

Gly Ser Leu Pro Gln Glu His Ile Ile Gln Lys Ile Lys Glu Cys Phe
        595                 600                 605

Arg Lys Leu Pro Ile Asn Arg Pro Ile Asp Trp Lys Val Cys Gln Arg
610                 615                 620

Ile Val Gly Leu Leu Gly Phe Ala Ala Pro Phe Thr Gln Cys Gly Tyr
625                 630                 635                 640

Pro Ala Leu Met Pro Leu Tyr Ala Cys Ile Gln Ser Lys Gln Ala Phe
            645                 650                 655

Thr Phe Ser Pro Thr Tyr Lys Ala Phe Leu Cys Lys Gln Tyr Leu Asn

```
              660                 665                 670
Leu Tyr Pro Val Ala Arg Gln Arg Pro Gly Leu Cys Gln Val Phe Ala
            675                 680                 685

Asp Ala Thr Pro Thr Gly Trp Gly Leu Val Met Gly His Gln Arg Met
        690                 695                 700

Arg Gly Thr Phe Ser Ala Pro Leu Pro Ile His Thr Ala Glu Leu Leu
705                 710                 715                 720

Ala Ala Cys Phe Ala Arg Ser Arg Ser Gly Ala Asn Ile Ile Gly Thr
                725                 730                 735

Asp Asn Ser Val Val Leu Ser Arg Lys Tyr Thr Ser Phe Pro Trp Leu
            740                 745                 750

Leu Gly Cys Ala Ala Asn Trp Ile Leu Arg Gly Thr Ser Phe Val Tyr
        755                 760                 765

Val Pro Ser Ala Leu Asn Pro Ala Asp Asp Pro Ser Arg Gly Arg Leu
    770                 775                 780

Gly Leu Ser Arg Pro Leu Leu Arg Leu Pro Phe Arg Pro Thr Thr Gly
785                 790                 795                 800

Arg Thr Ser Leu Tyr Ala Asp Ser Pro Ser Val Pro Ser His Leu Pro
                805                 810                 815

Asp Arg Val His Phe Ala Ser Pro Leu His Val Ala Trp Arg Pro Pro
            820                 825                 830

<210> SEQ ID NO 33
<211> LENGTH: 389
<212> TYPE: PRT
<213> ORGANISM: Hepatitis B virus
<220> FEATURE:
<223> OTHER INFORMATION: HBV S protein (YP_009173869)

<400> SEQUENCE: 33

Met Gly Gln Asn Leu Ser Thr Ser Asn Pro Leu Gly Phe Phe Pro Asp
1               5                   10                  15

His Gln Leu Asp Pro Ala Phe Arg Ala Asn Thr Ala Asn Pro Asp Trp
            20                  25                  30

Asp Phe Asn Pro Asn Lys Asp Thr Trp Pro Asp Ala Asn Lys Val Gly
        35                  40                  45

Ala Gly Ala Phe Gly Leu Gly Phe Thr Pro Pro His Gly Gly Leu Leu
    50                  55                  60

Gly Trp Ser Pro Gln Ala Gln Gly Ile Leu Gln Thr Leu Pro Ala Asn
65                  70                  75                  80

Pro Pro Pro Ala Ser Thr Asn Arg Gln Ser Gly Arg Gln Pro Thr Pro
                85                  90                  95

Leu Ser Pro Pro Leu Arg Asn Thr His Pro Gln Ala Met Gln Trp Asn
            100                 105                 110

Ser Thr Thr Phe His Gln Thr Leu Gln Asp Pro Arg Val Arg Gly Leu
        115                 120                 125

Tyr Phe Pro Ala Gly Gly Ser Ser Ser Gly Thr Val Asn Pro Val Leu
    130                 135                 140

Thr Thr Ala Ser Pro Leu Ser Ser Ile Phe Ser Arg Ile Gly Asp Pro
145                 150                 155                 160

Ala Leu Asn Met Glu Asn Ile Thr Ser Gly Phe Leu Gly Pro Leu Leu
                165                 170                 175

Val Leu Gln Ala Gly Phe Phe Leu Leu Thr Arg Ile Leu Thr Ile Pro
            180                 185                 190

Gln Ser Leu Asp Ser Trp Trp Thr Ser Leu Asn Phe Leu Gly Gly Thr
```

```
                195                 200                 205
Thr Val Cys Leu Gly Gln Asn Ser Gln Ser Pro Thr Ser Asn His Ser
210                 215                 220

Pro Thr Ser Cys Pro Pro Thr Cys Pro Gly Tyr Arg Trp Met Cys Leu
225                 230                 235                 240

Arg Arg Phe Ile Ile Phe Leu Phe Ile Leu Leu Cys Leu Ile Phe
                245                 250                 255

Leu Leu Val Leu Leu Asp Tyr Gln Gly Met Leu Pro Val Cys Pro Leu
            260                 265                 270

Ile Pro Gly Ser Ser Thr Thr Ser Thr Gly Pro Cys Arg Thr Cys Met
            275                 280                 285

Thr Thr Ala Gln Gly Thr Ser Met Tyr Pro Ser Cys Cys Cys Thr Lys
        290                 295                 300

Pro Ser Asp Gly Asn Cys Thr Cys Ile Pro Ile Pro Ser Ser Trp Ala
305                 310                 315                 320

Phe Gly Lys Phe Leu Trp Glu Trp Ala Ser Ala Arg Phe Ser Trp Leu
                325                 330                 335

Ser Leu Leu Val Pro Phe Val Gln Trp Phe Val Gly Leu Ser Pro Thr
            340                 345                 350

Val Trp Leu Ser Val Ile Trp Met Met Trp Tyr Trp Gly Pro Ser Leu
            355                 360                 365

Tyr Ser Ile Leu Ser Pro Phe Leu Pro Leu Leu Pro Ile Phe Phe Cys
370                 375                 380

Leu Trp Val Tyr Ile
385

<210> SEQ ID NO 34
<211> LENGTH: 281
<212> TYPE: PRT
<213> ORGANISM: Hepatitis B virus
<220> FEATURE:
<223> OTHER INFORMATION: HBV PreS2 protein (YP_009173870.1)

<400> SEQUENCE: 34

Met Gln Trp Asn Ser Thr Thr Phe His Gln Thr Leu Gln Asp Pro Arg
1               5                   10                  15

Val Arg Gly Leu Tyr Phe Pro Ala Gly Gly Ser Ser Ser Gly Thr Val
                20                  25                  30

Asn Pro Val Leu Thr Thr Ala Ser Pro Leu Ser Ser Ile Phe Ser Arg
            35                  40                  45

Ile Gly Asp Pro Ala Leu Asn Met Glu Asn Ile Thr Ser Gly Phe Leu
        50                  55                  60

Gly Pro Leu Leu Val Leu Gln Ala Gly Phe Phe Leu Leu Thr Arg Ile
65                  70                  75                  80

Leu Thr Ile Pro Gln Ser Leu Asp Ser Trp Trp Thr Ser Leu Asn Phe
                85                  90                  95

Leu Gly Gly Thr Thr Val Cys Leu Gly Gln Asn Ser Gln Ser Pro Thr
            100                 105                 110

Ser Asn His Ser Pro Thr Ser Cys Pro Pro Thr Cys Pro Gly Tyr Arg
        115                 120                 125

Trp Met Cys Leu Arg Arg Phe Ile Ile Phe Leu Phe Ile Leu Leu Leu
    130                 135                 140

Cys Leu Ile Phe Leu Leu Val Leu Leu Asp Tyr Gln Gly Met Leu Pro
145                 150                 155                 160

Val Cys Pro Leu Ile Pro Gly Ser Ser Thr Thr Ser Thr Gly Pro Cys
```

```
                    165                 170                 175
Arg Thr Cys Met Thr Thr Ala Gln Gly Thr Ser Met Tyr Pro Ser Cys
                180                 185                 190

Cys Cys Thr Lys Pro Ser Asp Gly Asn Cys Thr Cys Ile Pro Ile Pro
            195                 200                 205

Ser Ser Trp Ala Phe Gly Lys Phe Leu Trp Glu Trp Ala Ser Ala Arg
    210                 215                 220

Phe Ser Trp Leu Ser Leu Leu Val Pro Phe Val Gln Trp Phe Val Gly
225                 230                 235                 240

Leu Ser Pro Thr Val Trp Leu Ser Val Ile Trp Met Met Trp Tyr Trp
                245                 250                 255

Gly Pro Ser Leu Tyr Ser Ile Leu Ser Pro Phe Leu Pro Leu Leu Pro
                260                 265                 270

Ile Phe Phe Cys Leu Trp Val Tyr Ile
                275                 280

<210> SEQ ID NO 35
<211> LENGTH: 226
<212> TYPE: PRT
<213> ORGANISM: Hepatitis B virus
<220> FEATURE:
<223> OTHER INFORMATION: HBV S protein (YP_009173871.1)

<400> SEQUENCE: 35

Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
                20                  25                  30

Asp Ser Trp Trp Thr Ser Leu Asn Phe Leu Gly Gly Thr Thr Val Cys
            35                  40                  45

Leu Gly Gln Asn Ser Gln Ser Pro Thr Ser Asn His Ser Pro Thr Ser
    50                  55                  60

Cys Pro Pro Thr Cys Pro Gly Tyr Arg Trp Met Cys Leu Arg Arg Phe
65                  70                  75                  80

Ile Ile Phe Leu Phe Ile Leu Leu Cys Leu Ile Phe Leu Leu Val
                85                  90                  95

Leu Leu Asp Tyr Gln Gly Met Leu Pro Val Cys Pro Leu Ile Pro Gly
                100                 105                 110

Ser Ser Thr Thr Ser Thr Gly Pro Cys Arg Thr Cys Met Thr Thr Ala
            115                 120                 125

Gln Gly Thr Ser Met Tyr Pro Ser Cys Cys Cys Thr Lys Pro Ser Asp
    130                 135                 140

Gly Asn Cys Thr Cys Ile Pro Ile Pro Ser Ser Trp Ala Phe Gly Lys
145                 150                 155                 160

Phe Leu Trp Glu Trp Ala Ser Ala Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Ser Ile
    195                 200                 205

Leu Ser Pro Phe Leu Pro Leu Pro Ile Phe Phe Cys Leu Trp Val
                210                 215                 220

Tyr Ile
225
```

-continued

```
<210> SEQ ID NO 36
<211> LENGTH: 154
<212> TYPE: PRT
<213> ORGANISM: Hepatitis B virus
<220> FEATURE:
<223> OTHER INFORMATION: HBV X protein (YP_009173867.1)

<400> SEQUENCE: 36

Met Ala Ala Arg Leu Cys Cys Gln Leu Asp Pro Ala Arg Asp Val Leu
1               5                   10                  15

Cys Leu Arg Pro Val Gly Ala Glu Ser Cys Gly Arg Pro Phe Ser Gly
                20                  25                  30

Ser Leu Gly Thr Leu Ser Ser Pro Ser Pro Ser Ala Val Pro Thr Asp
            35                  40                  45

His Gly Ala His Leu Ser Leu Arg Gly Leu Pro Val Cys Ala Phe Ser
        50                  55                  60

Ser Ala Gly Pro Cys Ala Leu Arg Phe Thr Ser Ala Arg Arg Met Glu
65                  70                  75                  80

Thr Thr Val Asn Ala His Gln Ile Leu Pro Lys Val Leu His Lys Arg
                85                  90                  95

Thr Leu Gly Leu Ser Ala Met Ser Thr Thr Asp Leu Glu Ala Tyr Phe
            100                 105                 110

Lys Asp Cys Leu Phe Lys Asp Trp Glu Glu Leu Gly Glu Glu Ile Arg
        115                 120                 125

Leu Lys Val Phe Val Leu Gly Gly Cys Arg His Lys Leu Val Cys Ala
    130                 135                 140

Pro Ala Pro Cys Asn Phe Phe Thr Ser Ala
145                 150

<210> SEQ ID NO 37
<211> LENGTH: 212
<212> TYPE: PRT
<213> ORGANISM: Hepatitis B virus
<220> FEATURE:
<223> OTHER INFORMATION: HBV PreC protein (YP_009173857.1)

<400> SEQUENCE: 37

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
                20                  25                  30

Asp Pro Tyr Lys Glu Phe Gly Ala Thr Val Glu Leu Leu Ser Phe Leu
            35                  40                  45

Pro Ser Asp Phe Phe Pro Ser Val Arg Asp Leu Leu Asp Thr Ala Ser
        50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160
```

-continued

```
Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210

<210> SEQ ID NO 38
<211> LENGTH: 843
<212> TYPE: PRT
<213> ORGANISM: Hepatitis B virus
<220> FEATURE:
<223> OTHER INFORMATION: HBV pol protein (BAA32913.1)

<400> SEQUENCE: 38

Met Pro Leu Ser Tyr Gln His Phe Arg Lys Leu Leu Leu Leu Asp Asp
1               5                   10                  15

Glu Ala Gly Pro Leu Glu Glu Glu Leu Pro Arg Leu Ala Asp Glu Gly
            20                  25                  30

Leu Asn Arg Arg Val Ala Glu Asp Leu Asn Leu Gly Asn Leu Asn Val
        35                  40                  45

Ser Ile Pro Trp Thr His Lys Val Gly Asn Phe Thr Gly Leu Tyr Ser
    50                  55                  60

Ser Thr Val Pro Val Phe Asn Pro Glu Trp Gln Thr Pro Ser Phe Pro
65                  70                  75                  80

His Ile His Leu Gln Glu Asp Ile Ile Asn Arg Cys Gln Gln Tyr Val
                85                  90                  95

Gly Pro Leu Thr Val Asn Glu Lys Arg Arg Leu Lys Leu Ile Met Pro
            100                 105                 110

Ala Arg Phe Tyr Pro Asn Leu Thr Lys Tyr Leu Pro Leu Asp Lys Gly
        115                 120                 125

Ile Lys Pro Tyr Tyr Pro Glu His Ala Val Asn His Tyr Phe Lys Thr
    130                 135                 140

Arg His Tyr Leu His Thr Leu Trp Lys Ala Gly Ile Leu Tyr Lys Arg
145                 150                 155                 160

Glu Thr Thr Arg Ser Ala Ser Phe Cys Gly Ser Pro Tyr Ser Trp Glu
                165                 170                 175

Gln Glu Leu Gln His Gly Arg Leu Val Phe Gln Thr Ser Thr Arg His
            180                 185                 190

Gly Asp Lys Ser Phe Cys Ser Gln Ser Ser Gly Ile Leu Ser Arg Ser
        195                 200                 205

Pro Val Gly Pro Cys Val Arg Ser Gln Leu Lys Gln Ser Arg Leu Gly
    210                 215                 220

Leu Gln Pro Gln Gln Gly Ser Leu Ala Arg Gly Lys Ser Gly Arg Ser
225                 230                 235                 240

Gly Ser Ile Arg Ala Arg Val His Pro Thr Thr Arg Arg Ser Phe Gly
                245                 250                 255

Val Glu Pro Ser Gly Ser Gly His Ile Asp Asn Ser Ala Ser Ser Thr
            260                 265                 270

Ser Ser Cys Leu His Gln Ser Ala Val Arg Lys Thr Ala Tyr Ser His
        275                 280                 285

Leu Ser Thr Ser Lys Arg Gln Ser Ser Ser Gly His Ala Val Glu Leu
    290                 295                 300
```

```
His His Ile Pro Pro Ser Ser Ala Thr Pro Gln Ser Lys Gly Pro Ile
305                 310                 315                 320

Leu Ser Cys Trp Trp Leu Gln Phe Arg Asn Ser Lys Pro Cys Ser Asp
                325                 330                 335

Tyr Cys Leu Ser His Ile Val Asn Leu Leu Glu Asp Trp Gly Pro Cys
            340                 345                 350

Thr Glu His Gly Glu His Asn Ile Arg Ile Pro Arg Thr Pro Ala Arg
        355                 360                 365

Val Thr Gly Gly Val Phe Leu Val Asp Lys Asn Pro His Asn Thr Thr
    370                 375                 380

Glu Ser Arg Leu Val Val Asp Phe Ser Gln Phe Ser Arg Gly Ser Thr
385                 390                 395                 400

His Val Ser Trp Pro Lys Phe Ala Val Pro Asn Leu Gln Ser Leu Thr
                405                 410                 415

Asn Leu Leu Ser Ser Asn Leu Ser Trp Leu Ser Leu Asp Val Ser Ala
                420                 425                 430

Ala Phe Tyr His Ile Pro Leu His Pro Ala Ala Met Pro His Leu Leu
            435                 440                 445

Val Gly Ser Ser Gly Leu Pro Arg Tyr Val Ala Arg Leu Ser Ser Thr
    450                 455                 460

Ser Arg Asn Ile Asn Tyr Gln His Gly Thr Met Gln Asp Leu His Asp
465                 470                 475                 480

Ser Cys Ser Arg His Leu Tyr Val Ser Leu Leu Leu Leu Tyr Lys Thr
                485                 490                 495

Phe Gly Arg Lys Leu His Leu Tyr Ser His Pro Ile Ile Leu Gly Phe
                500                 505                 510

Arg Lys Ile Pro Met Gly Val Gly Leu Ser Pro Phe Leu Leu Ala Gln
            515                 520                 525

Phe Thr Ser Ala Ile Cys Ser Val Val Arg Arg Ala Phe Pro His Cys
            530                 535                 540

Leu Ala Phe Ser Tyr Met Asp Asp Val Val Leu Gly Ala Lys Ser Val
545                 550                 555                 560

Gln His Leu Glu Ser Leu Phe Thr Ala Val Thr Asn Phe Leu Leu Ser
                565                 570                 575

Leu Gly Ile His Leu Asn Pro Asn Lys Thr Lys Arg Trp Gly Tyr Ser
                580                 585                 590

Leu Asn Phe Met Gly Tyr Val Ile Gly Ser Trp Gly Thr Leu Pro Gln
                595                 600                 605

Asp His Ile Val Leu Lys Ile Lys Gln Cys Phe Arg Lys Leu Pro Val
            610                 615                 620

Asn Arg Pro Ile Asp Trp Lys Val Cys Gln Arg Ile Val Gly Leu Leu
625                 630                 635                 640

Gly Phe Ala Ala Pro Phe Thr Gln Cys Gly Tyr Pro Ala Leu Met Pro
                645                 650                 655

Leu Tyr Ala Cys Ile Gln Ser Lys Gln Ala Phe Thr Phe Ser Pro Thr
                660                 665                 670

Tyr Lys Ala Phe Leu Cys Lys Gln Tyr Leu Asn Leu Tyr Pro Val Ala
            675                 680                 685

Arg Gln Arg Ser Gly Leu Cys Gln Val Phe Ala Asp Ala Thr Pro Thr
        690                 695                 700

Gly Trp Gly Leu Ala Ile Gly His Arg Met Arg Gly Thr Phe Val
705                 710                 715                 720

Ala Pro Leu Pro Ile His Thr Ala Glu Leu Leu Ala Ala Cys Phe Ala
```

-continued

```
                    725                 730                 735
Arg Ser Arg Ser Gly Ala Lys Leu Ile Gly Thr Asp Asn Ser Val Val
            740                 745                 750

Leu Ser Arg Lys Tyr Thr Ser Phe Pro Trp Leu Leu Gly Cys Ala Ala
            755                 760                 765

Asn Trp Ile Leu Arg Gly Thr Ser Phe Val Tyr Val Pro Ser Ala Leu
            770                 775                 780

Asn Pro Ala Asp Asp Pro Ser Arg Gly Arg Leu Gly Leu Tyr Arg Pro
785                 790                 795                 800

Leu Leu His Leu Pro Phe Arg Pro Thr Thr Gly Arg Thr Ser Leu Tyr
                    805                 810                 815

Ala Val Ser Pro Ser Val Pro Ser His Leu Pro Asp Arg Val His Phe
            820                 825                 830

Ala Ser Pro Leu His Val Ala Trp Arg Pro Pro
            835                 840

<210> SEQ ID NO 39
<211> LENGTH: 400
<212> TYPE: PRT
<213> ORGANISM: Hepatitis B virus
<220> FEATURE:
<223> OTHER INFORMATION: HBV envelope protein (BAA32914.1)

<400> SEQUENCE: 39

Met Gly Gly Trp Ser Ser Lys Pro Arg Gln Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Asn
        35                  40                  45

Lys Asp His Trp Pro Glu Ala Asn Gln Val Gly Ala Gly Ala Phe Gly
    50                  55                  60

Pro Gly Phe Thr Pro Pro His Gly Gly Leu Leu Gly Trp Ser Pro Gln
65                  70                  75                  80

Ala Gln Gly Thr Leu Thr Thr Val Pro Val Ala Pro Pro Pro Ala Ser
                85                  90                  95

Thr Asn Arg Gln Ser Gly Arg Gln Pro Thr Pro Ile Ser Pro Pro Leu
            100                 105                 110

Arg Asp Ser His Pro Gln Ala Met Gln Trp Asn Ser Thr Thr Phe His
        115                 120                 125

Gln Ala Leu Leu His Pro Arg Val Arg Gly Leu Tyr Phe Pro Ala Gly
    130                 135                 140

Gly Ser Ser Ser Gly Thr Val Asn Pro Val Pro Thr Thr Ala Ser Pro
145                 150                 155                 160

Ile Ser Ser Ile Phe Ser Arg Thr Gly Asp Pro Ala Pro Asn Met Glu
                165                 170                 175

Asn Thr Thr Ser Gly Phe Leu Gly Pro Leu Leu Val Leu Gln Ala Gly
            180                 185                 190

Phe Phe Leu Leu Thr Arg Ile Leu Thr Ile Pro Gln Ser Leu Asp Ser
        195                 200                 205

Trp Trp Thr Ser Leu Asn Phe Leu Gly Gly Ala Pro Thr Cys Pro Gly
    210                 215                 220

Gln Asn Ser Gln Ser Pro Thr Ser Asn His Ser Pro Thr Ser Cys Pro
225                 230                 235                 240

Pro Ile Cys Pro Gly Tyr Arg Trp Met Cys Leu Arg Arg Phe Ile Ile
```

```
                     245                 250                 255
Phe Leu Phe Ile Leu Leu Leu Cys Leu Ile Phe Leu Leu Val Leu Leu
                260                 265                 270

Asp Tyr Gln Gly Met Leu Pro Val Cys Pro Leu Leu Pro Gly Thr Ser
            275                 280                 285

Thr Thr Ser Thr Gly Pro Cys Lys Thr Cys Thr Ile Pro Ala Gln Gly
        290                 295                 300

Thr Ser Met Phe Pro Ser Cys Cys Cys Thr Lys Pro Ser Asp Gly Asn
305                 310                 315                 320

Cys Thr Cys Ile Pro Ile Pro Ser Ser Trp Ala Phe Ala Arg Phe Leu
                325                 330                 335

Trp Glu Trp Ala Ser Val Arg Phe Ser Trp Leu Ser Leu Leu Val Pro
                340                 345                 350

Phe Val Gln Trp Phe Val Gly Leu Ser Pro Thr Val Trp Leu Ser Val
                355                 360                 365

Ile Trp Met Met Trp Tyr Trp Gly Pro Ser Leu Tyr Asn Ile Leu Ser
                370                 375                 380

Pro Phe Leu Pro Leu Leu Pro Ile Phe Phe Cys Leu Trp Val Tyr Ile
385                 390                 395                 400

<210> SEQ ID NO 40
<211> LENGTH: 210
<212> TYPE: PRT
<213> ORGANISM: Hepatitis B virus
<220> FEATURE:
<223> OTHER INFORMATION: HBV X protein (BAA32912.1)

<400> SEQUENCE: 40

Met Gly Leu Gly Tyr Trp Pro Ser Pro His Ala Trp Asn Leu Cys Gly
1               5                   10                  15

Ser Ser Ala Asp Pro Tyr Cys Gly Thr Pro Ser Ser Leu Phe Cys Ser
            20                  25                  30

Gln Pro Val Trp Ser Glu Thr Asp Arg Asn Gly Gln Leu Cys Cys Ser
        35                  40                  45

Leu Ser Glu Ile His Leu Leu Ser Met Ala Ala Arg Val Cys Cys Gln
    50                  55                  60

Leu Asp Pro Ala Arg Asp Val Leu Cys Leu Arg Pro Val Gly Ala Glu
65                  70                  75                  80

Ser Arg Gly Arg Pro Ile Ser Gly Pro Phe Gly Ser Leu Pro Ser Pro
                85                  90                  95

Ser Ser Ser Ala Val Pro Ala Asp His Gly Ala His Leu Ser Leu Arg
            100                 105                 110

Gly Leu Pro Val Cys Ala Phe Ser Ser Ala Gly Pro Cys Ala Leu Arg
        115                 120                 125

Phe Thr Ser Ala Arg Arg Met Glu Thr Thr Val Asn Ala His Gln Val
    130                 135                 140

Leu Pro Lys Val Leu Tyr Lys Arg Thr Leu Gly Leu Ser Ala Met Ser
145                 150                 155                 160

Thr Thr Asp Leu Glu Ala Tyr Phe Lys Asp Cys Leu Phe Lys Asp Trp
                165                 170                 175

Glu Glu Leu Gly Glu Glu Ile Arg Leu Met Ile Phe Val Leu Gly Gly
            180                 185                 190

Cys Arg His Lys Leu Val Cys Ser Pro Ala Pro Cys Asn Phe Phe Thr
        195                 200                 205

Ser Ala
```

<210> SEQ ID NO 41
<211> LENGTH: 389
<212> TYPE: PRT
<213> ORGANISM: Hepatitis B virus
<220> FEATURE:
<223> OTHER INFORMATION: HBV Large S protein (P03138.3)

<400> SEQUENCE: 41

```
Met Gly Gln Asn Leu Ser Thr Ser Asn Pro Leu Gly Phe Phe Pro Asp
1               5                   10                  15

His Gln Leu Asp Pro Ala Phe Arg Ala Asn Thr Ala Asn Pro Asp Trp
            20                  25                  30

Asp Phe Asn Pro Asn Lys Asp Thr Trp Pro Asp Ala Asn Lys Val Gly
        35                  40                  45

Ala Gly Ala Phe Gly Leu Gly Phe Thr Pro Pro His Gly Gly Leu Leu
    50                  55                  60

Gly Trp Ser Pro Gln Ala Gln Gly Ile Leu Gln Thr Leu Pro Ala Asn
65                  70                  75                  80

Pro Pro Pro Ala Ser Thr Asn Arg Gln Ser Gly Arg Gln Pro Thr Pro
                85                  90                  95

Leu Ser Pro Pro Leu Arg Asn Thr His Pro Gln Ala Met Gln Trp Asn
            100                 105                 110

Ser Thr Thr Phe His Gln Thr Leu Gln Asp Pro Arg Val Arg Gly Leu
        115                 120                 125

Tyr Phe Pro Ala Gly Gly Ser Ser Ser Gly Thr Val Asn Pro Val Leu
    130                 135                 140

Thr Thr Ala Ser Pro Leu Ser Ser Ile Phe Ser Arg Ile Gly Asp Pro
145                 150                 155                 160

Ala Leu Asn Met Glu Asn Ile Thr Ser Gly Phe Leu Gly Pro Leu Leu
                165                 170                 175

Val Leu Gln Ala Gly Phe Phe Leu Leu Thr Arg Ile Leu Thr Ile Pro
            180                 185                 190

Gln Ser Leu Asp Ser Trp Trp Thr Ser Leu Asn Phe Leu Gly Gly Thr
        195                 200                 205

Thr Val Cys Leu Gly Gln Asn Ser Gln Ser Pro Thr Ser Asn His Ser
    210                 215                 220

Pro Thr Ser Cys Pro Pro Thr Cys Pro Gly Tyr Arg Trp Met Cys Leu
225                 230                 235                 240

Arg Arg Phe Ile Ile Phe Leu Phe Ile Leu Leu Leu Cys Leu Ile Phe
                245                 250                 255

Leu Leu Val Leu Leu Asp Tyr Gln Gly Met Leu Pro Val Cys Pro Leu
            260                 265                 270

Ile Pro Gly Ser Ser Thr Thr Ser Thr Gly Pro Cys Arg Thr Cys Met
        275                 280                 285

Thr Thr Ala Gln Gly Thr Ser Met Tyr Pro Ser Cys Cys Cys Thr Lys
    290                 295                 300

Pro Ser Asp Gly Asn Cys Thr Cys Ile Pro Ile Pro Ser Ser Trp Ala
305                 310                 315                 320

Phe Gly Lys Phe Leu Trp Glu Trp Ala Ser Ala Arg Phe Ser Trp Leu
                325                 330                 335

Ser Leu Leu Val Pro Phe Val Gln Trp Phe Val Gly Leu Ser Pro Thr
            340                 345                 350

Val Trp Leu Ser Val Ile Trp Met Met Trp Tyr Trp Gly Pro Ser Leu
```

```
                    355                 360                 365
Tyr Ser Ile Leu Ser Pro Phe Leu Pro Leu Leu Pro Ile Phe Phe Cys
        370                 375                 380

Leu Trp Val Tyr Ile
385

<210> SEQ ID NO 42
<211> LENGTH: 183
<212> TYPE: PRT
<213> ORGANISM: Hepatitis B virus
<220> FEATURE:
<223> OTHER INFORMATION: HBV Core protein (P03146.1)

<400> SEQUENCE: 42

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 43
<211> LENGTH: 3182
<212> TYPE: DNA
<213> ORGANISM: Hepatitis B virus
<220> FEATURE:
<223> OTHER INFORMATION: Hepatitis B virus (strain ayw) genome

<400> SEQUENCE: 43
aattccactg catggcctga ggatgagtgt ttctcaaagg tggagacagc ggggtaggct      60
gccttcctga ctggcgattg gtggaggcag gaggcggatt tgctggcaaa gtttgtagta     120
tgccctgagc ctgagggctc accccaaaa ggcctccgtg cggtggggtg aaacccagcc     180
cgaatgctcc agctcctacc ttgttggcgt ctggccaggt gtccttgttg ggattgaagt     240
cccaatctgg atttgcggtg tttgctctga aggctggatc caactggtgg tcgggaaaga     300
atcccagagg attgctggtg gaaagattct gccccatgct gtagatcttg ttcccaagaa     360
tatggtgacc cacaaaatga ggcgctatgt gttgtttctc tcttatataa tatacccgcc     420
ttccatagag tgtgtaaata gtgtctagtt tggaagtaat gattaactag atgttctgga     480
```

```
taataaggtt taatacccct atccaatggt aaatatttgg taacctttgg ataaaacctg    540
gcaggcataa tcaattgcaa tcttcttttc tcattaactg tgagtgggcc tacaaactgt    600
tcacattttt tgataatgtc ttggtgtaaa tgtatattag gaaagatgg tgttttccaa     660 tgaggattaa agacaggtac agtagaagaa taaagcccag taaagttccc caccttatga    720
gtccaaggaa tactaacatt gagattcccg agattgagat cttctgcgac gcggcgattg    780
agaccttcgt ctgcgaggcg agggagttct cttctaggg gacctgcctc gtcgtctaac    840
aacagtagtc tccggaagtg ttgataggat aggggcattt ggtggtctat aagctggagg    900
agtgcgaatc cacactccga aagacaccaa atactctata actgtttctc ttccaaaagt    960
gagacaagaa atgtgaaacc acaagagttg cctgaacttt aggcccatat tagtgttgac   1020
ataactgact actaggtctc tagacgctgg atcttccaaa ttaacaccca cccaggtagc   1080
tagagtcatt agttccccc agcaaagaat tgcttgcctg agtgcagtat ggtgaggtga    1140
acaatgctca ggagactcta aggcttcccg atacagagct gaggcggtat ctagaagatc   1200
tcgtactgaa ggaaagaagt cagaaggcaa aaacgagagt aactccacag tagctccaaa   1260
ttctttataa gggtcgatgt ccatgcccca agccaccca aggcacagct tggaggcttg    1320
aacagtagga catgaacaag atgattag gcagaggtga aaaagttgca tggtgctggt     1380
gcgcagacca atttatgcct acagcctcct agtacaaaga cctttaacct aatctcctcc   1440
cccaactcct cccagtcttt aaacaaacag tctttgaagt atgcctcaag gtcggtcgtt   1500
gacattgctg agagtccaag agtcctctta tgtaagacct tgggcaatat ttggtgggcg   1560
ttcacggtgg tctccatgcg acgtgcagag gtgaagcgaa gtgcacacgg tccggcagat   1620
gagaaggcac agacggggag tccgcgtaaa gagaggtgcg ccccgtggtc ggtcggaacg   1680
gcagacggag aagggacga gagagtccca agcgaccccg agaagggtcg tccgcaggat    1740
tcagcgccga cgggacgtaa acaaaggacg tcccgcgcag gatccagttg gcagcacagc   1800
ctagcagcca tggaaacgat gtatatttgc gggataggac aacagagtta tcagtcccga   1860
taatgtttgc tccagacctg ctgcgagcaa acaagcggc taggagttcc gcagtatgga    1920
tcggcagagg agccgaaaag gttccacgca tgcgctgatg gccatgacc aagccccagc    1980 cagtgggggt tgcgtcagca aacacttggc acagacctgg ccgttgccgg gcaacgggt    2040 aaaggttcag gtattgttta cacagaaagg ccttgtaagt tggcgagaaa gtgaaagcct   2100
gcttagattg aatacatgca tacaaaggca tcaacgcagg ataaccacat tgtgtaaaag   2160
gggcagcaaa acccaaaaga cccacaattc gttgacatac tttccaatca ataggcctgt   2220
taataggaag ttttctaaaa cattctttga tttttgtat gatgtgttct tgtggcaagg    2280
acccataaca tccaatgaca taacccctaa aatttagaga gtaaccccat ctctttgttt   2340
tgttagggtt taaatgtata cccaaagaca aagaaaatt ggtaacagcg gtaaaaaggg    2400
actcaagatg ctgtacagac ttggccccca ataccacatc atccatataa ctgaaagcca   2460
aacagtgggg gaaagcccta cgaaccactg aacaaatggc actagtaaac tgagccagga   2520
gaaacgggct gaggcccact cccataggaa ttttccgaaa gcccaggatg atgggatggg   2580
aatacaggtg caatttccgt ccgaaggttt ggtacagcaa caggagggat acatagaggt   2640
tccttgagca gtagtcatgc aggtccggca tggtcccgtg ctggttgttg aggatcctgg   2700
aattagagga caaacgggca acataccttg atagtccaga agaaccaaca agaagatgag   2760
gcatagcagc aggatgaaga ggaagatgat aaaacgccgc agacacatcc agcgataacc   2820
```

```
aggacaagtt ggaggacaag aggttggtga gtgattggag gttggggact gcgaattttg    2880
gccaagacac acggtagttc cccctagaaa attgagagaa gtccaccacg agtctagact    2940
ctgcggtatt gtgaggattc ttgtcaacaa gaaaaacccc gcctgtaaca cgagaagggg    3000
tcctaggaat cctgatgtga tgttctccat gttcagcgca gggtcccaa tcctcgagaa     3060 gattgacgat aagggagagg cagtagtcag aacagggttt actgttcctg aactggagcc    3120
accagcaggg aaatacaggc ctctcactct gggatcttgc agagtttggt ggaaggttgt    3180
gg                                                                    3182

<210> SEQ ID NO 44
<211> LENGTH: 3182
<212> TYPE: DNA
<213> ORGANISM: Artificial Sequence
<220> FEATURE:
<223> OTHER INFORMATION: Reverse complement of SEQ ID NO: 16

<400> SEQUENCE: 44
ccacaacctt ccaccaaact ctgcaagatc ccagagtgag aggcctgtat ttccctgctg      60
gtggctccag ttcaggaaca gtaaaccctg ttctgactac tgcctctccc ttatcgtcaa     120
tcttctcgag gattggggac cctgcgctga acatggagaa catcacatca ggattcctag    180 gacccttct cgtgttacag gcggggtttt tcttgttgac aagaatcctc acaataccgc      240
agagtctaga ctcgtggtgg acttctctca attttctagg ggaactacc gtgtgtcttg     300 gccaaaattc gcagtcccca acctccaatc actcaccaac ctcttgtcct ccaacttgtc    360
ctggttatcg ctggatgtgt ctgcggcgtt ttatcatctt cctcttcatc ctgctgctat    420
gcctcatctt cttgttggtt cttctggact atcaaggtat gttgcccgtt tgtcctctaa    480
ttccaggatc ctcaacaacc agcacgggac catgccggac ctgcatgact actgctcaag    540
gaacctctat gtatccctcc tgttgctgta ccaaaccttc ggacggaaat tgcacctgta    600
ttcccatccc atcatcctgg gctttcggaa aattcctatg ggagtgggcc tcagcccgtt    660
tctcctggct cagtttacta gtgccatttg ttcagtggtt cgtagggctt tccccactg     720 tttggctttc agttatatgg atgatgtggt attggggggcc aagtctgtac agcatcttga    780
gtcccttttt accgctgtta ccaattttct tttgtctttg ggtatacatt taaaccctaa    840
caaaacaaag atgggggtt actctctaaa tttatgggt tatgtcattg gatgttatgg      900
gtccttgcca caagaacaca tcatacaaaa aatcaaagaa tgttttagaa aacttcctat    960
taacaggcct attgattgga agtatgtca acgaattgtg ggtcttttgg gttttgctgc    1020
cccttttaca caatgtggtt atcctgcgtt gatgcctttg tatgcatgta ttcaatctaa    1080
gcaggctttc actttctcgc caacttacaa ggccttctg tgtaaacaat acctgaacct     1140
ttaccccgtt gcccggcaac ggccaggtct gtgccaagtg tttgctgacg caaccccac    1200 tggctggggc ttggtcatgg ccatcagcg catgcgtgga acctttcgg ctcctctgcc     1260 gatccatact gcggaactcc tagccgcttg ttttgctcgc agcaggtctg gagcaaacat    1320
tatcgggact gataactctg ttgtcctatc ccgcaaatat acatcgtttc catggctgct    1380
aggctgtgct gccaactgga tcctgcgcgg gacgtccttt gtttacgtcc cgtcggcgct    1440
gaatcctgcg gacgaccctt ctcggggtcg cttgggactc tctcgtcccc ttctccgtct    1500
gccgttccga ccgaccacgg ggcgcacctc tctttacgcg gactcccgt ctgtgccttc     1560 tcatctgccg gaccgtgtgc acttcgcttc acctctgcac gtcgcatgga gccaccgtg    1620 aacgcccacc aaatattgcc caaggtctta cataagagga ctcttggact ctcagcaatg    1680
```

```
tcaacgaccg accttgaggc atacttcaaa gactgtttgt ttaaagactg ggaggagttg    1740
ggggaggaga ttaggttaaa ggtctttgta ctaggaggct gtaggcataa attggtctgc    1800
gcaccagcac catgcaactt tttcacctct gcctaatcat ctcttgttca tgtcctactg    1860
ttcaagcctc caagctgtgc cttgggtggc tttgggcat ggacatcgac ccttataaag    1920
aatttggagc tactgtggag ttactctcgt ttttgccttc tgacttcttt ccttcagtac    1980
gagatcttct agataccgcc tcagctctgt atcgggaagc cttagagtct cctgagcatt    2040
gttcacctca ccatactgca ctcaggcaag caattctttg ctgggggaa ctaatgactc    2100 tagctacctg ggtgggtgtt aatttggaag atccagcgtc tagagaccta gtagtcagtt    2160
atgtcaacac taatatgggc ctaaagttca ggcaactctt gtggtttcac atttcttgtc    2220
tcacttttgg aagagaaaca gttatagagt atttggtgtc tttcggagtg tggattcgca    2280
ctcctccagc ttatagacca ccaaatgccc ctatcctatc aacacttccg gagactactg    2340
ttgttagacg acgaggcagg tcccctagaa gaagaactcc ctcgcctcgc agacgaaggt    2400
ctcaatcgcc gcgtcgcaga agatctcaat ctcgggaatc tcaatgttag tattccttgg    2460
actcataagg tggggaactt tactgggctt tattcttcta ctgtacctgt ctttaatcct    2520
cattggaaaa caccatcttt tcctaatata catttacacc aagacattat caaaaaatgt    2580
gaacagtttg taggcccact cacagttaat gagaaaagaa gattgcaatt gattatgcct    2640
gccaggtttt atccaaaggt taccaaatat ttaccattgg ataagggtat taaaccttat    2700
tatccagaac atctagttaa tcattacttc caaactagac actatttaca cactctatgg    2760
aaggcgggta tattatataa gagagaaaca acacatagcg cctcattttg tgggtcacca    2820
tattcttggg aacaagatct acagcatggg gcagaatctt tccaccagca atcctctggg    2880
attctttccc gaccaccagt tggatccagc cttcagagca acaccgcaa atccagattg    2940 ggacttcaat cccaacaagg acacctggcc agacgccaac aaggtaggag ctggagcatt    3000
cgggctgggt ttcaccccac cgcacggagg ccttttgggg tggagccctc aggctcaggg    3060
catactacaa actttgccag caaatccgcc tcctgcctcc accaatcgcc agtcaggaag    3120
gcagcctacc ccgctgtctc cacctttgag aaacactcat cctcaggcca tgcagtggaa    3180
tt                                                                   3182
```

<210> SEQ ID NO 45
<211> LENGTH: 389
<212> TYPE: PRT
<213> ORGANISM: Hepatitis B virus
<220> FEATURE:
<223> OTHER INFORMATION: HBV S protein (P03142.4)

<400> SEQUENCE: 45

Met Gly Thr Asn Leu Ser Val Pro Asn Pro Leu Gly Phe Leu Pro Asp
1               5                   10                  15

His Gln Leu Asp Pro Ala Phe Gly Ala Asn Ser Thr Asn Pro Asp Trp
            20                  25                  30

Asp Phe Asn Pro Ile Lys Asp His Trp Pro Ala Ala Asn Gln Val Gly
        35                  40                  45

Val Gly Ala Phe Gly Pro Gly Leu Thr Pro His Gly Gly Ile Leu
    50                  55                  60

Gly Trp Ser Pro Gln Ala Gln Gly Ile Leu Thr Thr Val Ser Thr Ile
65                  70                  75                  80

Pro Pro Pro Ala Ser Thr Asn Arg Gln Ser Gly Arg Gln Pro Thr Pro

```
                    85                  90                  95
Ile Ser Pro Pro Leu Arg Asp Ser His Pro Gln Ala Met Gln Trp Asn
                100                 105                 110

Ser Thr Ala Leu His Gln Ala Leu Gln Asp Pro Arg Val Arg Gly Leu
            115                 120                 125

Tyr Leu Pro Ala Gly Gly Ser Ser Gly Thr Val Asn Pro Ala Pro
        130                 135                 140

Asn Ile Ala Ser His Ile Ser Ser Ile Ser Ala Arg Thr Gly Asp Pro
145                 150                 155                 160

Val Thr Ile Met Glu Asn Ile Thr Ser Gly Phe Leu Gly Pro Leu Leu
                165                 170                 175

Val Leu Gln Ala Gly Phe Phe Leu Leu Thr Arg Ile Leu Thr Ile Pro
            180                 185                 190

Gln Ser Leu Asp Ser Trp Trp Thr Ser Leu Asn Phe Leu Gly Gly Ser
        195                 200                 205

Pro Val Cys Leu Gly Gln Asn Ser Gln Ser Pro Thr Ser Asn His Ser
    210                 215                 220

Pro Thr Ser Cys Pro Pro Ile Cys Pro Gly Tyr Arg Trp Met Cys Leu
225                 230                 235                 240

Arg Arg Phe Ile Ile Phe Leu Phe Ile Leu Leu Leu Cys Leu Ile Phe
                245                 250                 255

Leu Leu Val Leu Leu Asp Tyr Gln Gly Met Leu Pro Val Cys Pro Leu
            260                 265                 270

Ile Pro Gly Ser Thr Thr Thr Ser Thr Gly Pro Cys Lys Thr Cys Thr
        275                 280                 285

Thr Pro Ala Gln Gly Asn Ser Lys Phe Pro Ser Cys Cys Cys Thr Lys
    290                 295                 300

Pro Thr Asp Gly Asn Cys Thr Cys Ile Pro Ile Pro Ser Ser Trp Ala
305                 310                 315                 320

Phe Ala Lys Tyr Leu Trp Glu Trp Ala Ser Val Arg Phe Ser Trp Leu
                325                 330                 335

Ser Leu Leu Val Pro Phe Val Gln Trp Phe Val Gly Leu Ser Pro Thr
            340                 345                 350

Val Trp Leu Ser Ala Ile Trp Met Met Trp Tyr Trp Gly Pro Ser Leu
        355                 360                 365

Tyr Ser Ile Val Ser Pro Phe Ile Pro Leu Leu Pro Ile Phe Phe Cys
    370                 375                 380

Leu Trp Val Tyr Ile
385

<210> SEQ ID NO 46
<211> LENGTH: 185
<212> TYPE: PRT
<213> ORGANISM: Hepatitis B virus
<220> FEATURE:
<223> OTHER INFORMATION: HBV Core protein (P03149.1)

<400> SEQUENCE: 46

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
```

```
                  50                  55                  60

Leu Met Thr Leu Ala Thr Trp Val Gly Asn Asn Leu Gln Asp Pro Ala
 65                  70                  75                  80

Ser Arg Asp Leu Val Val Asn Tyr Val Asn Thr Asn Met Gly Leu Lys
                 85                  90                  95

Ile Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
130                 135                 140

Glu Thr Thr Val Val Arg Arg Arg Asp Arg Gly Arg Ser Pro Arg Arg
145                 150                 155                 160

Arg Thr Pro Ser Pro Arg Arg Arg Arg Ser Gln Ser Pro Arg Arg Arg
                165                 170                 175

Arg Ser Gln Ser Arg Glu Ser Gln Cys
            180                 185

<210> SEQ ID NO 47
<211> LENGTH: 3200
<212> TYPE: DNA
<213> ORGANISM: Hepatitis B virus
<220> FEATURE:
<223> OTHER INFORMATION: Hepatitis B virus complete DNA sequence
      (subtype adw)

<400> SEQUENCE: 47
ttccactgcc ttgcaccaag ctctgcagga tcccagagtc aggggtctgt atcttcctgc      60
tggtggctcc agttcaggaa cagtaaaccc tgctccgaat attgcctctc acatctcgtc    120
aatctccgcg aggactgggg accctgtgac gatcatggag aacatcacat caggattcct    180
aggacccctg ctcgtgttac aggcggggtt tttcttgttg acaagaatcc tcacaatacc    240
gcagagtcta gactcgtggt ggacttctct caattttcta ggggatcac  ccgtgtgtct    300 tggccaaaat tcgcagtccc caacctccaa tcactcacca acctcctgtc ctccaatttg    360
tcctggttat cgctggatgt gtctgcggcg ttttatcata ttcctcttca tcctgctgct    420
atgcctcatc ttcttattgg ttcttctgga ttatcaaggt atgttgcccg tttgtcctct    480
aattccagga tcaacaacaa ccagtacggg accatgcaaa acctgcacga ctcctgctca    540
aggcaactct aagtttccct catgttgctg tacaaaacct acggatggaa attgcacctg    600
tattcccatc ccatcgtcct gggctttcgc aaaataccta tgggagtggg cctcagtccg    660
tttctcttgg ctcagtttac tagtgccatt tgttcagtgg ttcgtagggc tttcccccac    720
tgtttggctt tcagctatat ggatgatgtg gtattggggg ccaagtctgt acagcatcgt    780
gagtcccttt ataccgctgt taccaatttt cttttgtctc tgggtataca tttaaaccct    840
aacaaaacaa aaagatgggg ttattcccta aacttcatgg ctacataatg gaagttgg     900 ggaactttgc cacaggatca tattgtacaa agatcaaac  actgttttag aaacttcct     960 gttaacaggc ctattgattg aaagtatgt  caaagaattg tgggtctttt gggctttgct   1020
gctccattta cacaatgtgg atatcctgcc ttaatgcctt tgtatgcatg tatacaagct   1080
aaacaggctt tcactttctc gccaacttac aaggcctttc taagtaaaca gtacatgaac   1140
ctttaccccg ttgctcggca acggcctggt ctgtgccaag tgtttgctga cgcaaccccc   1200
actggctggg gcttagccat aggccatcag cgcatgcgtg gaacctttgt ggctcctctg   1260
```

```
ccgatccata ctgcggaact cctagccgct tgttttgctc gcagccggtc tggagcaaag    1320
ctcatcggaa ctgacaattc tgtcgtcctc tcgcggaaat atacatcatt tccatggctg    1380
ctaggctgta ctgccaactg gatccttcgc gggacgtcct ttgtttacgt cccgtcggcg    1440
ctgaatcccg cggacgaccc ctctcggggc cgcttgggac tctctcgtcc ccttctccgt    1500
ctgccgttcc agccgaccac ggggcgcacc tctctttacg cggtctcccc gtctgtgcct    1560
tctcatctgc cggtccgtgt gcacttcgct tcacctctgc acgttgcatg gcgaccaccg    1620
tgaacgccca tcagatcctg cccaaggtct tacataagag gactcttgga ctcccagcaa    1680
tgtcaacgac cgaccttgag gcctacttca aagactgtgt gtttaaggac tgggaggagt    1740
tgggggagga gattaggtta atgatctttg tattaggagg ctgtaggcat aaattggtct    1800
gcgcaccagc accatgcaac ttttcacct ctgcctaatc atctcttgta catgtcccac    1860
tgttcaagcc tccaagctgt gccttgggtg gctttggggc atggacattg acccttataa    1920
agaatttgga gctactgtgg agttactctc gttttgcct tctgacttct ttccttccgt    1980
acgagatctc ctagacaccg cctcagctct gtatcgagaa gccttagagt ctcctgagca    2040
ttgctcacct caccatactg cactcaggca agccattctc tgctgggggg aattgatgac    2100
tctagctacc tgggtgggta ataatttgca agatccagca tccagagatc tagtagtcaa    2160
ttatgttaat actaacatgg gtttaaagat caggcaacta ttgtggtttc atatatcttg    2220
ccttactttt ggaagagaga ctgtacttga atatttggtc tctttcggag tgtggattcg    2280
cactcctcca gcctatagac caccaaatgc ccctatctta tcaacacttc cggaaactac    2340
tgttgttaga cgacgggacc gaggcaggtc ccctagaaga agaactccct cgcctcgcag    2400
acgcagatct caatcgccgc gtcgcagaag atctcaatct cgggaatctc aatgttagta    2460
ttccttggac tcataaggtc ggaaacttta cggggcttta ttcctctaca gtacctatct    2520
ttaatcctga atggcaaact ccttcctttc ctaagattca tttacaagag gacattatta    2580
ataggtgtca acaatttgtg ggccctctca ctgtaaatga aaagagaaga ttgaaattaa    2640
ttatgcctgc tagattctat cctacccaca ctaaatattt gcccttagac aaaggaatta    2700
aaccttatta tccagatcag gtagttaatc attacttcca aaccgacat tatttacata    2760 ctctttggaa ggctggtatt ctatataaga gggaaaccac acgtagcgca tcattttgcg    2820
ggtcaccata ttcttgggaa caagagctac agcattcgca aaggcatggg gacgaatctt    2880
tctgttccca accctctggg attccttccc gatcatcagt tggaccctgc attcggagcc    2940
aactcaacaa atccagattg ggacttcaac cccatcaagg accactggcc agcagccaac    3000
caggtaggag tgggagcatt cgggccaggg ctcacccctc cacacggcgg tattttgggg    3060
tggagccctc aggctcaggg catattgacc acagtgtcaa caattcctcc tcctgcctcc    3120
accaatcggc agtcaggaag gcagcctact cccatctctc cacctctaag agacagtcat    3180
cctcaggcca tgcagtggaa                                                 3200
```

<210> SEQ ID NO 48
<211> LENGTH: 3200
<212> TYPE: DNA
<213> ORGANISM: Artificial Sequence
<220> FEATURE:
<223> OTHER INFORMATION: Reverse complement of SEQ ID NO: 47

<400> SEQUENCE: 48

```
ttccactgca tggcctgagg atgactgtct cttagaggtg gagagatggg agtaggctgc      60
cttcctgact gccgattggt ggaggcagga ggaggaattg ttgacactgt ggtcaatatg     120
```

```
ccctgagcct gagggctcca ccccaaaata ccgccgtgtg gaggggtgag ccctggcccg    180
aatgctccca ctcctacctg gttggctgct ggccagtggt ccttgatggg gttgaagtcc    240
caatctggat ttgttgagtt ggctccgaat gcagggtcca actgatgatc gggaaggaat    300
cccagagggt tgggaacaga aagattcgtc cccatgcctt tgcgaatgct gtagctcttg    360
ttcccaagaa tatggtgacc cgcaaaatga tgcgctacgt gtggtttccc tcttatatag    420
aataccagcc ttccaaagag tatgtaaata atgtctggtt tggaagtaat gattaactac    480
ctgatctgga taataaggtt taattccttt gtctaagggc aaatatttag tgtgggtagg    540
atagaatcta gcaggcataa ttaatttcaa tcttctcttt tcatttacag tgagagggcc    600
cacaaattgt tgacacctat taataatgtc ctcttgtaaa tgaatcttag gaaaggaagg    660
agtttgccat tcaggattaa agataggtac tgtagaggaa taaagccccg taagtttcc     720 gaccttatga gtccaaggaa tactaacatt gagattcccg agattgagat cttctgcgac    780
gcggcgattg agatctgcgt ctgcgaggcg agggagttct tcttctaggg gacctgcctc    840
ggtcccgtcg tctaacaaca gtagtttccg gaagtgttga taagataggg gcatttggtg    900
gtctataggc tggaggagtg cgaatccaca ctccgaaaga gaccaaatat tcaagtacag    960
tctctcttcc aaaagtaagg caagatatat gaaaccacaa tagttgcctg atctttaaac   1020
ccatgttagt attaacataa ttgactacta gatctctgga tgctggatct tgcaaattat   1080
tacccaccca ggtagctaga gtcatcaatt ccccccagca gagaatggct tgcctgagtg   1140
cagtatggtg aggtgagcaa tgctcaggag actctaaggc ttctcgatac agagctgagg   1200
cggtgtctag gagatctcgt acggaaggaa agaagtcaga aggcaaaaac gagagtaact   1260
ccacagtagc tccaaattct ttataagggt caatgtccat gccccaaagc cacccaaggc   1320
acagcttgga ggcttgaaca gtgggacatg tacaagagat gattaggcag aggtgaaaaa   1380
gttgcatggt gctggtgcgc agaccaattt atgcctacag cctcctaata caaagatcat   1440
taacctaatc tcctccccca actcctccca gtccttaaac acacagtctt tgaagtaggc   1500
ctcaaggtcg gtcgttgaca ttgctgggag tccaagagtc ctcttatgta agaccttggg   1560
caggatctga tgggcgttca cggtggtcgc catgcaacgt gcagaggtga agcgaagtgc   1620
acacggaccg gcagatgaga aggcacagag ggggagaccg cgtaaagaga ggtgcgcccc   1680
gtggtcggct ggaacggcag acggagaagg ggacagagag gtcccaagcg gccccgagag   1740
gggtcgtccg cgggattcag cgccgacggg acgtaaacaa aggacgtccc gcgaaggatc   1800
cagttggcag tacagcctag cagccatgga aatgatgtat atttccgcga gaggacgaca   1860
gaattgtcag ttccgatgag ctttgctcca gaccggctgc gagcaaaaca agcggctagg   1920
agttccgcag tatggatcgg cagaggagcc acaaaggttc cacgcatgcg ctgatggcct   1980
atggctaagc cccagccagt gggggttgcg tcagcaaaca cttggcacag accaggccgt   2040
tgccgagcaa cggggtaaag gttcatgtac tgtttactta gaaaggcctt gtaagttggc   2100
gagaaagtga agcctgtttt agcttgtata catgcataca aaggcattaa ggcaggatat   2160
ccacattgtg taaatggagc agcaaagccc aaaagaccca caattctttg acatactttc   2220
caatcaatag gcctgttaac aggaagtttt ctaaacagt gtttgatctt ttgtacaata    2280
tgatcctgtg gcaaagttcc ccaacttcca attatgtagc ccatgaagtt tagggaataa   2340
ccccatcttt ttgttttgtt agggtttaaa tgtatacccca gagacaaaag aaaattggta   2400
acagcggtat aaagggactc acgatgctgt acagacttgg ccccaatac cacatcatcc    2460
```

```
atatagctga aagccaaaca gtgggggaaa gccctacgaa ccactgaaca aatggcacta    2520
gtaaactgag ccaagagaaa cggactgagg cccactccca taggtatttt gcgaaagccc    2580
aggacgatgg gatgggaata caggtgcaat ttccatccgt aggttttgta cagcaacatg    2640
agggaaactt agagttgcct tgagcaggag tcgtgcaggt tttgcatggt cccgtactgg    2700
ttgttgttga tcctggaatt agaggacaaa cgggcaacat accttgataa tccagaagaa    2760
ccaataagaa gatgaggcat agcagcagga tgaagaggaa tatgataaaa cgccgcagac    2820
acatccagcg ataaccagga caaattggag gacaggaggt tggtgagtga ttggaggttg    2880
gggactgcga attttggcca agacacacgg gtgatccccc tagaaaattg agagaagtcc    2940
accacgagtc tagactctgc ggtattgtga ggattcttgt caacaagaaa accccgcct     3000 gtaacacgag caggggtcct aggaatcctg atgtgatgtt ctccatgatc gtcacagggt    3060
ccccagtcct cgcggagatt gacgagatgt gagaggcaat attcggagca gggtttactg    3120
ttcctgaact ggagccacca gcaggaagat acagacccct gactctggga tcctgcagag    3180
cttggtgcaa ggcagtggaa                                                 3200
```

<210> SEQ ID NO 49
<211> LENGTH: 3182
<212> TYPE: DNA
<213> ORGANISM: Hepatitis B virus
<220> FEATURE:
<223> OTHER INFORMATION: Hepatitis B virus subtype ayw, complete genome

<400> SEQUENCE: 49

```
aattccacaa cctttcacca aactctgcaa gatcccagag tgagaggcct gtatttccct      60
gctggtggct ccagttcagg agcagtaaac cctgttccga ctactgcctc tcccttatcg     120
tcaatcttct cgaggattgg ggaccctgcg ctgaacatgg agaacatcac atcaggattc     180
ctaggacccc ttctcgtgtt acaggcgggg ttttcttgt tgacaagaat cctcacaata     240
ccgcagagtc tagactcgtg gtggacttct ctcaattttc tagggggaac taccgtgtgt     300
cttggccaaa attcgcagtc cccaacctcc aatcactcac caacctcctg tcctccaact     360
tgtcctggtt atcgctggat gtgtctgcgg cgttttatca tcttcctctt catcctgctg     420
ctatgcctca tcttcttgtt ggttcttctg gactatcaag gtatgttgcc cgtttgtcct     480
ctaattccag gatcctcaac caccagcacg ggaccatgcc gaacctgcat gactactgct     540
caaggaacct ctatgtatcc ctcctgttgc tgtaccaaac cttcggacgg aaattgcacc     600
tgtattccca tcccatcatc ctgggctttc ggaaaattcc tatgggagtg gcctcagcc     660 cgtttctcct ggctcagttt actagtgcca tttgttcagt ggttcgtagg gctttccccc    720
actgtttggc tttcagttat atggatgatg tggtattggg ggccaagtct gtacagcatc    780
ttgagtccct ttttaccgct gttaccaatt tcttttgtc tttgggtata catttaaacc    840
ctaacaaaac aaagagatgg ggttactctc tgaattttat gggttatgtc attggaagtt    900
atgggtcctt gccacaagaa cacatcatac aaaaaatcaa gaatgttttt agaaaacttc    960
ctattaacag gcctattgat tggaaagtat gtcaacgaat tgtgggtctt ttgggttttg    1020
ctgccccatt tacacaatgt ggttatcctg cgttaatgcc cttgtatgca tgtattcaat    1080
ctaagcaggc tttcactttc tcgccaactt acaaggcctt tctgtgtaaa caatacctga    1140 accttttaccc cgttgcccgg caacggccag gtctgtgcca agtgtttgct gacgcaaccc    1200
ccactggctg gggcttggtc atgggccatc agcgcgtgcg tggaaccttt tcggctcctc    1260
tgccgatcca tactgcggaa ctcctagccg cttgttttgc tcgcagcagg tctggagcaa    1320
```

```
acattatcgg gactgataac tctgttgtcc tctcccgcaa atatacatcg tatccatggc    1380
tgctaggctg tgctgccaac tggatcctgc gcgggacgtc ctttgtttac gtcccgtcgg    1440
cgctgaatcc tgcggacgac ccttctcggg gtcgcttggg actctctcgt ccccttctcc    1500
gtctgccgtt ccgaccgacc acggggcgca cctctcttta cgcggactcc ccgtctgtgc    1560
cttctcatct gccggaccgt gtgcacttcg cttcacctct gcacgtcgca tggagaccac    1620
cgtgaacgcc caccgaatgt tgcccaaggt cttacataag aggactcttg gactctctgc    1680
aatgtcaacg accgaccttg aggcatactt caaagactgt tgtttaaag actgggagga    1740 gttgggggag gagattagat taaaggtctt tgtactagga ggctgtaggc ataaattggt    1800
ctgcgcacca gcaccatgca acttttttcac ctctgcctaa tcatctcttg ttcatgtcct    1860
actgttcaag cctccaagct gtgccttggg tggctttggg gcatggacat cgacccttat    1920
aaagaatttg gagctactgt ggagttactc tcgttttgc cttctgactt cttccttca    1980 gtacgagatc ttctagatac cgcctcagct ctgtatcggg aagccttaga gtctcctgag    2040
cattgttcac ctcaccatac tgcactcagg caagcaattc tttgctgggg ggaactaatg    2100
actctagcta cctgggtggg tgttaatttg gaagatccag catctagaga cctagtagtc    2160
agttatgtca acactaatat gggcctaaag ttcaggcaac tcttgtggtt tcacatttct    2220
tgtctcactt ttggaagaga aaccgttata gagtatttgg tgtctttcgg agtgtggatt    2280
cgcactcctc cagcttatag accaccaaat gccccctatcc tatcaacact tccggaaact    2340
actgttgtta gacgacgagg caggtcccct agaagaagaa ctccctcgcc tcgcagacga    2400
aggtctcaat cgccgcgtcg cagaagatct caatctcggg aacctcaatg ttagtattcc    2460
ttggactcat aaggtgggga actttactgg tctttattct tctactgtac ctgtctttaa    2520
tcctcattgg aaaacaccat cttttcctaa tatacattta caccaagaca ttatcaaaaa    2580
atgtgaacag tttgtaggcc cacttacagt taatgagaaa agaagattgc aattgattat    2640
gcctgctagg ttttatccaa aggttaccaa atatttacca ttggataagg gtattaaacc    2700
ttattatcca gaacatctag ttaatcatta cttccaaact agacactatt tacacactct    2760
atggaaggcg ggtatattat ataagagaga acaacacat agcgcctcat tttgtgggtc    2820
accatattct tgggaacaag atctacagca tggggcagaa tctttccacc agcaatcctc    2880
tgggattctt tcccgaccac cagttggatc cagccttcag agcaaacaca gcaaatccag    2940
attgggactt caatcccaac aaggacacct ggccagacgc caacaaggta ggagctggag    3000
cattcgggct gggtttcacc ccaccgcacg gaggcctttt ggggtggagc cctcaggctc    3060
agggcatact acaaactttg ccagcaaatc cgcctcctgc ctccaccaat cgccagacag    3120
gaaggcagcc taccccgctg tctccacctt tgagaaacac tcatcctcag gccatgcagt    3180
gg                                                                  3182
```

HEPATITIS B VIRUS (HBV) DSRNA AGENT COMPOSITIONS AND METHODS OF USE THEREOF

STATEMENT REGARDING SEQUENCE LISTING

The Sequence Listing associated with this application is provided in text format in lieu of a paper copy, and is hereby incorporated by reference into the specification. The name of the text file containing the Sequence Listing is 930385_410USPC_SEQUENCE LISTING.txt. The text file is 83.1 KB, was created on Feb. 11, 2021, and is being submitted electronically via EFS-Web.

BACKGROUND

Worldwide more than 400 million people are chronically infected with HBV and are, thus, at increased risk of developing serious liver disease, such as chronic hepatitis, cirrhosis, liver failure, and hepatocellular carcinoma (HCC) resulting in an estimated 600,000 deaths each year.

The natural evolution of chronic HBV infection includes four consecutive phases: (1) early 'immunotolerant' phase, high levels of virus replication and minimal liver inflammation; (2) immune reactive phase, significant hepatic inflammation and elevated serum aminotransferases; with some patients progressing to (3) 'non-replicative' phase, seroconversion to anti-HBe, undetectable or low level of viremia (below 2000 IU/ml by PCR-based assays), and resolution of hepatic inflammation; and (4) HBeAg-negative chronic hepatitis B, due to the emergence of specific viral mutations, which prevent the production of HBeAg but do not hamper virus replication. This form of chronic hepatitis B (CHB) is characterized by fluctuating serum HBV DNA and serum aminotransferases (ALT and AST) levels and progressive liver disease. It is important to note that CHB may present either as HBeAg-positive or HBeAg-negative CHB. Longitudinal studies of patients with CHB indicate that the 5-year cumulative incidence of developing cirrhosis ranges from 8 to 20%. The 5-year cumulative incidence of hepatic decompensation is approximately 20%. The worldwide incidence of HCC has increased and presently constitutes the fifth most common cancer. The annual incidence of HBV-related HCC is high, ranging from 2-5% when cirrhosis is established.

The primary goal of treatment for HBV is to permanently suppress HBV replication and improve liver disease. Clinically important short-term goals are to achieve HBeAg-seroconversion, normalization of serum ALT and AST, resolution of liver inflammation, and prevention of hepatic decompensation. The ultimate goal of treatment is to achieve durable response to prevent development of cirrhosis and liver cancer to prolong survival. HBV infection cannot be eradicated completely due to persistence of a particular form of viral covalently closed circular DNA (cccHBV DNA) in the nuclei of infected hepatocytes. However, treatment-induced clearance of serum HBsAg is a marker of termination of chronic HBV infection and has been associated with the best long-term outcome.

The current standard methods of treatment for HBV include interferon- or thymosin α1-based immunotherapies and the suppression of viral production by inhibition of the HBV polymerase. HBV polymerase inhibitors are effective in reducing viral production but have little to no effect in rapidly reducing HBsAg or can slowly reduce HBsAg with long term treatment in a limited number of patients (as is the case with tenofovir disoproxil fumarate). Interferon-based immunotherapy can achieve a reduction of both viral production and early removal of HBsAg from the blood, but only in a small percentage of treated subjects. The generally accepted role of HBsAg in the blood is to sequester anti-HBsAg antibodies and allow infectious viral particles to escape immune detection, which is likely one of the reasons why HBV infection remains a chronic condition. In addition HBsAg, HBeAg, and HBcAg all have immuno-inhibitory properties and the persistence of these viral proteins in the blood of patients following the administration of any of the currently available treatments for HBV is likely having a significant impact in preventing patients from achieving immunological control of their HBV infection.

Although the three primary HBV proteins (HBsAg, HBeAg, and HBcAg) all have immunoinhibitory properties, HBsAg comprises the overwhelming majority of HBV protein in the circulation of HBV infected subjects. Additionally, while the removal (via seroconversion) of HBeAg or reductions in serum viremia are not correlated with the development of sustained control of HBV infection off treatment, the removal of serum HBsAg from the blood (and seroconversion) in HBV infection is a well-recognized prognostic indicator of antiviral response on treatment that will lead to control of HBV infection off treatment (although this only occurs in a small fraction of patients receiving immunotherapy). Thus, while reduction of all three major HBV proteins (HBsAg, HBeAg, and HBcAg) may result in the optimal removal of inhibitory effect, the removal of HBsAg alone is likely sufficient in and of itself to remove the bulk of the viral inhibition of immune function in subjects with HBV infection.

Therefore, in the absence of any current treatment regimen that can restore immunological control of HBV in a large proportion of patients, there is a need for an effective treatment against HBV infection that can inhibit viral replication as well as restore immunological control in the majority of patients. Accordingly, there is a need in the art for alternative therapies and combination therapies for subjects infected with HBV or having an HBV-associated disease.

SUMMARY OF THE INVENTION

In some embodiments, the present disclosure provides double stranded ribonucleic acid (dsRNA) agent compositions that affect the RNA-induced silencing complex (RISC)-mediated cleavage of RNA transcripts of a Hepatitis B virus (HBV) gene. The HBV gene may be within a cell, e.g., a cell within a subject, such as a human.

The present disclosure also provides methods and therapies for treating a subject having a disorder that would benefit from inhibiting expression of an HBV gene, e.g., an HBV infection or an HBV-associated disease, such as chronic Hepatitis B infection (CHB), using dsRNA agent compositions that affect the RNA-induced silencing complex (RISC)-mediated cleavage of RNA transcripts of an HBV gene for inhibiting the expression of an HBV gene.

In one aspect, the present disclosure provides dsRNA agents for inhibiting expression of HBV. For example, the present disclosure provides a dsRNA agent comprising a sense strand and an antisense strand forming a double stranded region, wherein the antisense strand comprises the modified nucleotide sequence as set forth in:

```
                                        (SEQ ID NO: 16)
5'-usGfsuga(Agn)gCfGfaaguGfcAfcacsusu-3', (SEQ ID NO: 18)
5'-usGfsuga(Agn)gcgaaguGfdCAfcacsusu-3', (SEQ ID NO: 20)
5'-usGfsudGa(Agn)gCfGfaaguGfcAfcacsusu-3', (SEQ ID NO: 23)
5'-usGfsudGadAgdCGfaaguGfcAfcacsusu-3', (SEQ ID NO: 24)
5'-usGfsuga(Agn)dGCfGfaaguGfcAfcacsusu-3', (SEQ ID NO: 25)
5'-usGfsudGadAgdCGfaaguGfcAfdCacsusu-3',
or (SEQ ID NO: 28)
5'-usGfsuga(Agn)gCfGfaaguGfdCAfcacsusu-3',
``` wherein a, c, g, and u are 2'-O-methyladenosine-3'-phosphate, 2'-O-methylcytidine-3'-phosphate, 2'-O-methylguanosine-3'-phosphate, and 2'-O-methyluridine-3'-phosphate, respectively;

Af, Cf, Gf, and Uf are 2'-fluoroadenosine-3'-phosphate, 2'-fluorocytidine-3'-phosphate, 2'-fluoroguanosine-3'-phosphate, and 2'-fluorouridine-3'-phosphate, respectively;

dA, dC, dG, and dT are 2'-deoxyadenosine-3'-phosphate, 2'-deoxycytidine-3'-phosphate, 2'-deoxyguanosine-3'-phosphate, and 2'-deoxythymidine-3'-phosphate, respectively;

(Agn) is adenosine-glycol nucleic acid (GNA); and s is a phosphorothioate linkage.

In some embodiments, the sense strand comprises the modified nucleotide

```
sequence
                                        (SEQ ID NO: 29)
5'-gsusguGfcAfCfUfucgcuucaca-3',
``` wherein a, c, g, and u are 2'-O-methyladenosine-3'-phosphate, 2'-O-methylcytidine-3'-phosphate, 2'-O-methylguanosine-3'-phosphate, and 2'-O-methyluridine-3'-phosphate, respectively;

Af, Cf, Gf, and Uf are 2'-fluoroadenosine-3'-phosphate, 2'-fluorocytidine-3'-phosphate, 2'-fluoroguanosine-3'-phosphate, and 2'-fluorouridine-3'-phosphate, respectively; and s is a phosphorothioate linkage.

In some embodiments, the antisense strand and the sense strand comprise the modified nucleotide sequences as set forth in:

```
(a)
                                        (SEQ ID NO: 16)
5'-usGfsuga(Agn)gCfGfaaguGfcAfcacsusu-3'
and (SEQ ID NO: 29)
5'-gsusguGfcAfCfUfucgcuucaca-3';

(b)
                                        (SEQ ID NO: 18)
5'-usGfsuga(Agn)gcgaaguGfdCAfcacsusu-3'
and (SEQ ID NO: 29)
5'-gsusguGfcAfCfUfucgcuucaca-3';

(c)
                                        (SEQ ID NO: 20)
5'-usGfsudGa(Agn)gCfGfaaguGfcAfcacsusu-3'
and (SEQ ID NO: 29)
5'-gsusguGfcAfCfUfucgcuucaca-3';

(d)
                                        (SEQ ID NO: 23)
5'-usGfsudGadAgdCGfaaguGfcAfcacsusu-3'
and (SEQ ID NO: 29)
5'-gsusguGfcAfCfUfucgcuucaca-3';

(e)
                                        (SEQ ID NO: 24)
5'-usGfsuga(Agn)dGCfGfaaguGfcAfcacsusu-3'
and (SEQ ID NO: 29)
5'-gsusguGfcAfCfUfucgcuucaca-3';

(f)
                                        (SEQ ID NO: 25)
5'-usGfsudGadAgdCGfaaguGfcAfdCacsusu-3'
and (SEQ ID NO: 29)
5'-gsusguGfcAfCfUfucgcuucaca-3';
or (g)
                                        (SEQ ID NO: 28)
5'-usGfsuga(Agn)gCfGfaaguGfdCAfcacsusu-3'
and (SEQ ID NO: 29)
5'-gsusguGfcAfCfUfucgcuucaca-3';
``` wherein a, c, g, and u are 2'-O-methyladenosine-3'-phosphate, 2'-O-methylcytidine-3'-phosphate, 2'-O-methylguanosine-3'-phosphate, and 2'-O-methyluridine-3'-phosphate, respectively;

Af, Cf, Gf, and Uf are 2'-fluoroadenosine-3'-phosphate, 2'-fluorocytidine-3'-phosphate, 2'-fluoroguanosine-3'-phosphate, and 2'-fluorouridine-3'-phosphate, respectively;

dA, dC, dG, and dT are 2'-deoxyadenosine-3'-phosphate, 2'-deoxycytidine-3'-phosphate, 2'-deoxyguanosine-3'-phosphate, and 2'-deoxythymidine-3'-phosphate, respectively;

(Agn) is adenosine-glycol nucleic acid (GNA); and s is a phosphorothioate linkage.

In some embodiments, at least one strand of the dsRNA agent comprises a 3' overhang of at least 1 nucleotide. In some embodiments, at least one strand of the dsRNA agent comprises a 3' overhang of 2 nucleotides.

In some embodiments, the double stranded region of the dsRNA agent is 19-21 nucleotide pairs in length.

In some embodiments, each strand of the dsRNA agent independently has 19-23 nucleotides. In some embodiments, each strand of the dsRNA agent independently has 19-21 nucleotides.

In some embodiments, dsRNA agent further comprises a ligand. In some embodiments, the ligand is conjugated to the 3' end of the sense strand of the dsRNA agent. In some embodiments, the ligand is an N-acetylgalactosamine (GalNAc) derivative. In certain embodiments, the ligand is

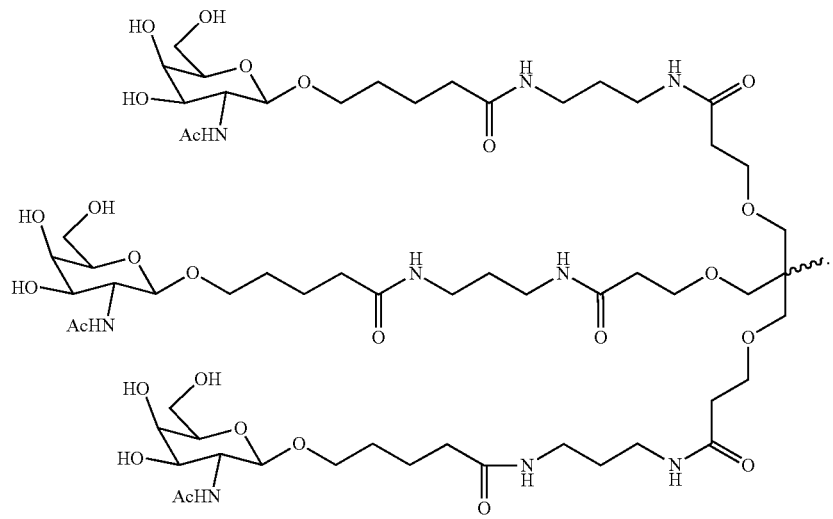 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In some embodiments, the dsRNA agent is conjugated to the ligand as shown in the following schematic

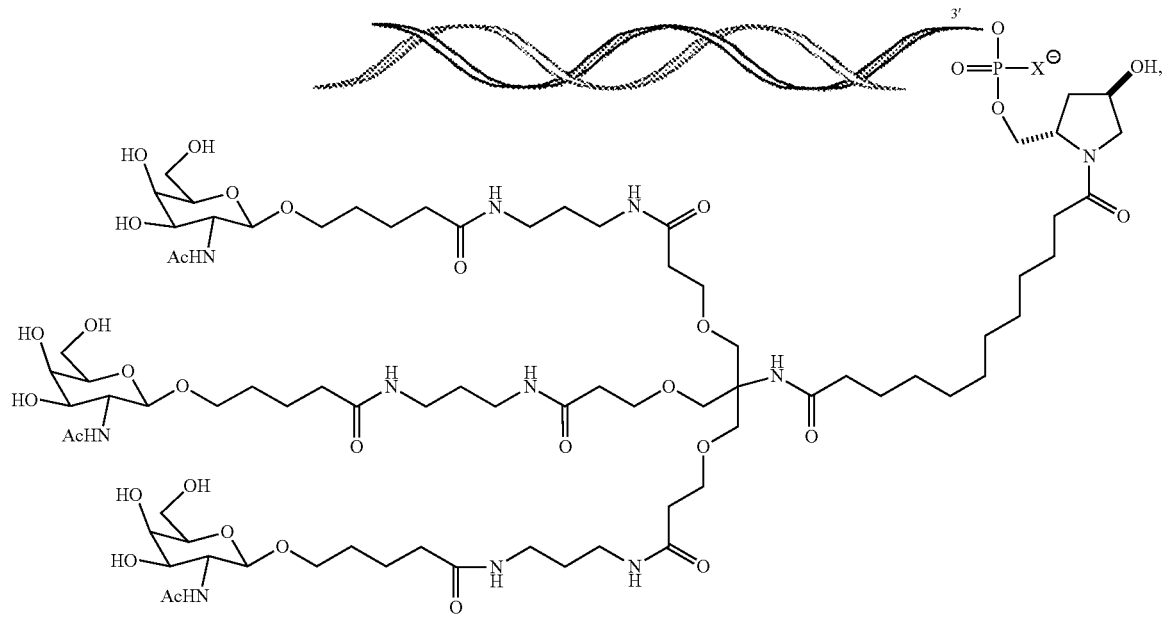

wherein X is O or S. In some embodiments, the X is O.

In some embodiments, the antisense strand consists of the modified nucleotide sequence as set forth in:

```
                                      (SEQ ID NO: 16)
5'-usGfsuga(Agn)gCfGfaaguGfcAfcacsusu-3', (SEQ ID NO: 18)
5'-usGfsuga(Agn)gcgaaguGfdCAfcacsusu-3', (SEQ ID NO: 20)
5'-us GfsudGa(Agn)gCfGfaaguGfcAfcacsusu-3', (SEQ ID NO: 23)
5'-usGfsudGadAgdCGfaaguGfcAfcacsusu-3',
```

-continued

```
                                      (SEQ ID NO: 24)
5'-usGfsuga(Agn)dGCfGfaaguGfcAfcacsusu-3', (SEQ ID NO: 25)
5'-usGfsudGadAgdCGfaaguGfcAfdCacsusu-3'
or (SEQ ID NO: 28)
5'-usGfsuga(Agn)gCfGfaaguGfdCAfcacsusu-3',
``` wherein a, c, g, and u are 2'-O-methyladenosine-3'-phosphate, 2'-O-methylcytidine-3'-phosphate, 2'-O-methylguanosine-3'-phosphate, and 2'-O-methyluridine-3'-phosphate, respectively;

Af, Cf, Gf, and Uf are 2'-fluoroadenosine-3'-phosphate, 2'-fluorocytidine-3'-phosphate, 2'-fluoroguanosine-3'-phosphate, and 2'-fluorouridine-3'-phosphate, respectively;

dA, dC, dG, and dT are 2'-deoxyadenosine-3'-phosphate, 2'-deoxycytidine-3'-phosphate, 2'-deoxyguanosine-3'-phosphate, and 2'-deoxythymidine-3'-phosphate, respectively;

(Agn) is adenosine-glycol nucleic acid (GNA); and s is a phosphorothioate linkage.

In some embodiments, the present disclosure provides a dsRNA agent, wherein the sense strand and the antisense strand consist of the modified nucleotide sequences as set forth in:

(a)
(SEQ ID NO: 16)
5'-usGfsuga(Agn)gCfGfaaguGfcAfcacsusu-3'
and (SEQ ID NO: 29)
5'-gsusguGfcAfCfUfucgcuucaca-3';

(b)
(SEQ ID NO: 18)
5'-usGfsuga(Agn)gcgaaguGfdCAfcacsusu-3'
and (SEQ ID NO: 29)
5'-gsusguGfcAfCfUfucgcuucaca-3';

(c)
(SEQ ID NO: 20)
5'-usGfsudGa(Agn)gCfGfaaguGfcAfcacsusu-3'
and (SEQ ID NO: 29)
5'-gsusguGfcAfCfUfucgcuucaca-3';

(d)
(SEQ ID NO: 23)
5'-usGfsudGadAgdCGfaaguGfcAfcacsusu-3'
and (SEQ ID NO: 29)
5'-gsusguGfcAfCfUfucgcuucaca-3';

(e)
(SEQ ID NO: 24)
5'-usGfsuga(Agn)dGCfGfaaguGfcAfcacsusu-3'
and (SEQ ID NO: 29)
5'-gsusguGfcAfCfUfucgcuucaca-3';

(f)
(SEQ ID NO: 25)
5'-usGfsudGadAgdCGfaaguGfcAfdCacsusu-3'
and (SEQ ID NO: 29)
5'-gsusguGfcAfCfUfucgcuucaca-3';
or (g)
(SEQ ID NO: 28)
5'-usGfsuga(Agn)gCfGfaaguGfdCAfcacsusu-3'
and (SEQ ID NO: 29)
5'-gsusguGfcAfCfUfucgcuucaca-3';

wherein a, c, g, and u are 2'-O-methyladenosine-3'-phosphate, 2'-O-methylcytidine-3'-phosphate, 2'-O-methylguanosine-3'-phosphate, and 2'-O-methyluridine-3'-phosphate, respectively;

Af, Cf, Gf, and Uf are 2'-fluoroadenosine-3'-phosphate, 2'-fluorocytidine-3'-phosphate, 2'-fluoroguanosine-3'-phosphate, and 2'-fluorouridine-3'-phosphate, respectively;

dA, dC, dG, and dT are 2'-deoxyadenosine-3'-phosphate, 2'-deoxycytidine-3'-phosphate, 2'-deoxyguanosine-3'-phosphate, and 2'-deoxythymidine-3'-phosphate, respectively;

(Agn) is adenosine-glycol nucleic acid (GNA);

s is a phosphorothioate linkage; and the 3' end of the sense strand is conjugated to an N-[tris(GalNAc-alkyl)-amidodecanoyl)]-4-hydroxyprolinol (L96) ligand.

In another aspect, the present disclosure also provides a cell containing a dsRNA agent as disclosed herein.

The present disclosure also provides a pharmaceutical composition comprising a dsRNA agent described herein and a pharmaceutical excipient.

The present disclosure also provides a method of inhibiting Hepatitis B virus (HBV) gene expression in a cell, the method comprising contacting the cell with a dsRNA agent or a pharmaceutical composition as disclosed herein, thereby inhibiting expression of the HBV gene in the cell. In some embodiments, the cell is within a subject. In some embodiments, the subject is a human. In some embodiments, the subject suffers from an HBV-associated disease. In some embodiments the cell is in vitro. In some embodiments, the HBV gene expression is inhibited by at least 80%, 90%, 95%, or 98%, or to below the level of detection of the assay method.

The present disclosure also provides a method of inhibiting replication of a Hepatitis B virus (HBV) in a cell, the method comprising contacting the cell with a dsRNA agent or a pharmaceutical composition as disclosed herein, thereby inhibiting replication of the HBV in the cell. In some embodiments, the cell is within a subject. In some embodiments, the subject is a human. In certain embodiments, the subject suffers from an HBV-associated disease. In some embodiments, the cell is in vitro. In certain embodiments, replication of HBV in the cell is inhibited by at least 80%, 90%, 95%, or 98%, or to below the level of detection of the assay method.

Also provided herein is a method of reducing the level of a Hepatitis B virus (HBV) antigen in a subject infected with HBV, comprising administering to the subject a therapeutically effective amount of a dsRNA agent or a pharmaceutical composition as disclosed herein, thereby reducing the level of the HBV antigen in the subject. In some embodiments, the HBV antigen is HBsAg. In some embodiments, the HBV antigen is HBeAg. In some embodiments, the HBV antigen is measured in serum from a subject. In some embodiments, the subject is HBeAg positive. In some embodiments, the subject is HBeAg negative. In some embodiments, the HBV antigen level is reduced in serum by at least 1 log 10, at least 2 log 10, at least 3 log 10, or at least 4 log 10; or to below the level of detection of the assay.

The present disclosure also provides a method of reducing the viral load of Hepatitis B virus (HBV) in a subject infected with HBV, comprising administering to the subject a therapeutically effective amount of a dsRNA agent or a pharmaceutical composition as disclosed herein, thereby reducing the viral load of HBV in the subject. In some embodiments, the HBV viral load is measured in serum from a subject. In some embodiments, the subject is HBeAg positive. In some embodiments, the subject is HBeAg negative. In some embodiments, the HBV viral load is reduced in serum by at least 1 log 10, at least 2 log 10, at least 3 log 10, or at least 4 log 10; or to below the level of detection of the assay.

Also provided herein is a method of treating a subject having a Hepatitis B virus (HBV) infection or an HBV-associated disorder, comprising administering to the subject a therapeutically effective amount of a dsRNA agent a pharmaceutical composition as disclosed herein, thereby treating the subject. In some embodiments, the subject is HBeAg positive. In some embodiments, the subject is HBeAg negative. In some embodiments, the HBV-associated disorder is chronic hepatitis and the subject is HBeAg positive. In some embodiments, the HBV-associated disorder is chronic hepatitis and the subject is HBeAg negative.

In some embodiments of the aforementioned methods, the dsRNA agent is administered to the subject at a dose of 0.01 mg/kg to 10 mg/kg, 0.5 mg/kg to 50 mg/kg, or 3 mg/kg to 10 mg/kg. In some embodiments of the methods, the dsRNA agent is administered to the subject at a dose of 3 mg/kg to 10 mg/kg. In some embodiments of the methods, the dsRNA agent is administered to the subject at a fixed dose of 50 mg to 200 mg.

In some embodiments of the aforementioned methods, the dsRNA agent is administered to the subject subcutaneously.

In some embodiments of the aforementioned methods, the dsRNA agent is administered to the subject in two or more doses.

In some embodiments of the aforementioned methods, the dsRNA agent is administered to the subject once per month, once every two months, or once every three months. In some embodiments of the methods, the dsRNA agent is administered to the subject no more than once per month.

In some embodiments of the aforementioned methods, the method further comprises administering to the subject an additional therapeutic agent, e.g., one or more additional therapeutic agents. An additional therapeutic agent can include, but is not limited to, an antiviral agent, a reverse transcriptase inhibitor, an immune stimulator, a therapeutic vaccine, a viral entry inhibitor, an oligonucleotide that inhibits the secretion or release of HbsAg, a capsid inhibitor, and a covalently closed circular (ccc) HBV DNA inhibitor, and a combination of any of the foregoing. In some embodiments, the additional therapeutic agent is a reverse transcriptase inhibitor.

In some embodiments, more than one additional therapeutic is administered, and the additional therapeutic agents are a reverse transcriptase inhibitor and an immune stimulator. A reverse transcriptase inhibitor can include, but is not limited to, Tenofovir disoproxil fumarate (TDF), Tenofovir alafenamide, Lamivudine, Adefovir dipivoxil, Entecavir (ETV), Telbivudine, and AGX-1009. An immune stimulator can include, but is not limited to, pegylated interferon alfa 2a (PEG-IFN-α2a), Interferon alfa-2b, a recombinant human interleukin-7, and a Toll-like receptor 7 (TLR7) agonist.

Also provided herein are compositions for practicing any of the methods disclosed herein. In some embodiments, the disclosure provides a dsRNA agent or a pharmaceutical composition as disclosed herein for use in the treatment of a Hepatitis B virus (HBV) infection in a subject. In some embodiments, the present disclosure provides a dsRNA agent or a pharmaceutical composition as disclosed herein for use in the treatment of a Hepatitis B virus (HBV)-associated disorder in a subject. In some embodiments, the HBV-associated disorder is chronic hepatitis and the subject is HBeAg positive. In some embodiments, the HBV-associated disorder is chronic hepatitis and the subject is HBeAg negative. In some embodiments, the subject is being or has been administered an additional therapeutic agent, e.g., an antiviral agent, a reverse transcriptase inhibitor, an immune stimulator, a therapeutic vaccine, a viral entry inhibitor, an oligonucleotide that inhibits the secretion or release of HbsAg, a capsid inhibitor, or a covalently closed circular (ccc) HBV DNA inhibitor, or a combination of any of the foregoing. In some embodiments, the additional therapeutic agent is a reverse transcriptase inhibitor, e.g., Tenofovir disoproxil fumarate (TDF), Tenofovir alafenamide, Lamivudine, Adefovir dipivoxil, Entecavir (ETV), Telbivudine, or AGX-1009. In some embodiments, the additional therapeutic agents being administered are a reverse transcriptase inhibitor (e.g., Tenofovir disoproxil fumarate (TDF), Tenofovir alafenamide, Lamivudine, Adefovir dipivoxil, Entecavir (ETV), Telbivudine, or AGX-1009) and an immune stimulator (e.g., pegylated interferon alfa 2a (PEG-IFN-α2a), Interferon alfa-2b, a recombinant human interleukin-7, or a Toll-like receptor 7 (TLR7) agonist).

The present disclosure provides for the use of a dsRNA agent or a pharmaceutical composition as disclosed herein, for practicing any of the aforementioned methods.

The present disclosure also provides for the use of a dsRNA agent as disclosed herein for the preparation or manufacture of a medicament for practicing any of the aforementioned methods.

The present disclosure also provides kits comprising a dsRNA agent or a pharmaceutical composition as disclosed herein, optionally with instructions for practicing a method described herein.

BRIEF DESCRIPTION OF THE DRAWINGS

FIG. 2A shows serum levels of HBsAg of HBV-AAV mice pre-dose (Days −24, −2, 0), or following a single dose of AD-81890 at 0.3, 1, or 3 mg/kg (Days 14, 21, 33, 47, 59, 74). Each point represents a mean of n=6-9 animals and the bars represent SD. FIG. 2B shows serum levels of HBsAg of HBV-AAV mice relative to pre-dose (Days −24, −2, 0), or following a single dose of AD-81890 at 0.3, 1, or 3 mg/kg (Days 14, 21, 33, 47, 59, 74). Each point represents a mean of n of 6-9 animals and the bars represent SD.

Figure 1:
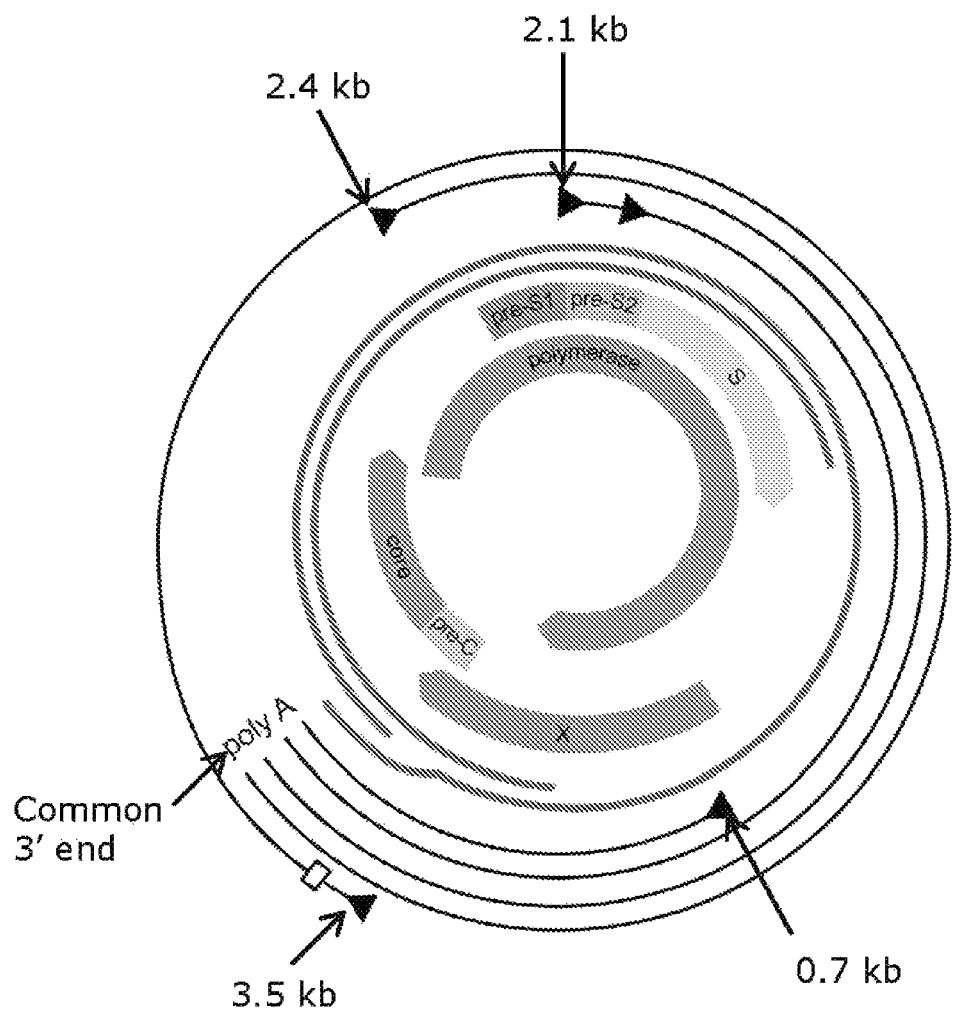
FIG. 1 schematically depicts the structure of the approximately 3.2 kb double stranded HBV genome. Replication of the HBV genome occurs through an RNA intermediate and produces 4 overlapping viral transcripts (an about 3.5 kb transcript, an about 2.4 kb transcript, an about 2.1 kb transcript, and an about 0.7 kb transcript) encoding seven viral proteins (pre-S1, pre-S2, S, P, X, pre-C, and C) translated across three reading frames.

Mice were dosed on Days 0, 21, 28, 35, and 42 with 12, 36, or 100 mg/kg of AD-66810, AD-81890, or PBS (control) by subcutaneous injection (n=4 per group). Blood was collected by retro-orbital bleed twice weekly and serum was prepared using routine methods.

DETAILED DESCRIPTION

The present disclosure provides dsRNA agent compositions that affect the RNA-induced silencing complex (RISC)-mediated cleavage of RNA transcripts of a Hepatitis B virus (HBV) gene. The gene may be within a cell, e.g., a cell within a subject, such as a human. The use of these dsRNA agents enables the targeted degradation of mRNAs of the corresponding gene (HBV gene) in mammals.

The dsRNA agents described herein have been designed to target regions in the HBV genome that are conserved across at least eight known genotypes of HBV. In addition, the dsRNA agents of the present disclosure have been designed to inhibit all steps of the HBV life cycle, e.g., replication, assembly, secretion of virus, and secretion of sub-viral antigens, by inhibiting expression of more than one HBV gene. In particular, since transcription of the HBV genome results in polycistronic, overlapping RNAs, in some embodiments a dsRNA agent targeting a single HBV gene results in significant inhibition of expression of most or all HBV transcripts. For example, because the HBV genome is transcribed into a single mRNA, a dsRNA agent of the present disclosure targeting the S gene will result in inhibition of not only S gene expression but also the expression of the "downstream" polymerase gene. Furthermore, the dsRNA agents of the present disclosure have been designed to inhibit HBV viral replication by targeting HBV structural genes, and the HBV X gene thereby permitting a subject's immune system to detect and respond to the presence of HBsAg to produce anti-HBV antibodies to clear an HBV infection. Without intending to be limited by theory, it is believed that a combination or sub-combination of the foregoing properties and the specific target sites or the specific modifications in these dsRNA agents confer to the dsRNA agents of the present disclosure improved efficacy, stability, safety, potency, and durability.

Using in vitro and in vivo assays, the present inventors have demonstrated that dsRNA agents targeting an HBV gene can potently mediate RNAi, resulting in significant inhibition of expression of more than one HBV gene. Thus, methods and compositions including these dsRNA agents are useful for treating a subject having an HBV infection or an HBV-associated disease, such as chronic hepatitis B (CHB).

Accordingly, the present disclosure also provides methods for treating a subject having a disorder that would benefit from inhibiting or reducing the expression of an HBV gene, e.g., an HBV-associated disease, such as chronic Hepatitis B virus infection (CHB), using dsRNA agent compositions that affect the RNA-induced silencing complex (RISC)-mediated cleavage of RNA transcripts of an HBV gene.

The dsRNA agents of the present disclosure include an RNA strand (the antisense strand) having a region of complementarity that is about 19-21 nucleotides in length, e.g., about 19 nucleotides in length that is substantially complementary to at least part of an mRNA transcript of an HBV gene of at least one HBV genotype. It is understood that there are multiple HBV genotypes such that a dsRNA agent of the present disclosure may vary in its degree of complementarity to different HBV genotypes.

In some embodiments, the sense and antisense strands form a duplex of 19-21 contiguous nucleotides.

The following detailed description discloses how to make and use compositions containing dsRNA agents to inhibit the expression of an HBV gene as well as compositions, uses, and methods for treating subjects having diseases and disorders that would benefit from inhibition or reduction of the expression of an HBV gene.

I. Definitions

In order that the present disclosure may be more readily understood, certain terms are first defined. In addition, it should be noted that whenever a value or range of values of a parameter are recited, it is intended that values and ranges intermediate to the recited values are also intended to be part of this feature.

Unless the context requires otherwise, throughout the present specification and claims, the word "comprise" and variations thereof, such as "comprises" and "comprising," are to be construed in an open, inclusive sense, that is, as "including, but not limited to". "Consisting of" shall mean excluding more than trace elements of other ingredients or substantial method steps disclosed herein. For example, a polynucleotide consists of a sequence of nucleotides when it does not include any additional nucleotides, but does not preclude the incorporation of a ligand, e.g., a targeting ligand, or modifications. The term "consisting essentially of" limits the scope of a claim to the specified materials or steps, or to those that do not materially affect the basic characteristics of a claimed invention. For example, a pharmaceutical composition consisting essentially of the elements as defined herein would not exclude trace contaminants from the isolation and purification method and pharmaceutically acceptable carriers, such as phosphate buffered saline, preservatives, and the like. Similarly, a polynucleotide consists essentially of a nucleotide sequence when the polynucleotide includes additional nucleotides that contribute to at most 20% of the length of the polynucleotide and do not substantially affect activity of the polynucleotide (e.g., alters the activity of the polynucleotide by no more than 50%). Embodiments defined by each of the transitional terms are within the scope of this invention.

The articles "a" and "an" are used herein to refer to one or to more than one (i.e., to at least one) of the grammatical object of the article. By way of example, "an element" means one element or more than one element, e.g., a plurality of elements.

The term "including" is used herein to mean, and is used interchangeably with, the phrase "including but not limited to."

The term "or" is used herein to mean, and is used interchangeably with, the term "and/or," unless context clearly indicates otherwise. For example, "sense strand or antisense strand" is understood as "sense strand or antisense strand or sense strand and antisense strand."

The term "about" is used herein to mean within the typical ranges of tolerances in the art. For example, "about" can be understood as within 2 standard deviations from the mean. When "about" is present before a series of numbers or a range, it is understood that "about" can modify each of the numbers in the series or range.

The term "at least" prior to a number or series of numbers is understood as each number in the series and all subsequent numbers or integers that could logically be included, as clear from context. For example, the number of nucleotides in a nucleic acid molecule must be an integer. For example, "at least 18 nucleotides of a 21 nucleotide nucleic acid molecule" means that 18, 19, 20, or 21 nucleotides have the indicated property. When at least is present before a series of numbers or a range, it is understood that "at least" can modify each of the numbers in the series or range.

As used herein, "no more than" or "less than" is understood as the value adjacent to the phrase and logical lower values or integers, as logical from context, to zero. For example, a duplex with an overhang of "no more than 2 nucleotides" has a 2, 1, or 0 nucleotide overhang. When "no more than" is present before a series of numbers or a range, it is understood that "no more than" can modify each of the numbers in the series or range.

As used herein, ranges include both the upper and lower limit.

In the event of a conflict between a sequence and its indicated site on a transcript or other sequence, the nucleotide sequence recited in the specification takes precedence.

Various embodiments of the present disclosure can be combined as determined appropriate by one of skill in the art.

As used herein, "Hepatitis B virus," used interchangeably with the term "HBV" refers to the well-known non-cytopathic, liver-tropic DNA virus belonging to the Hepadnaviridae family.

The HBV genome is partially double-stranded, circular DNA with overlapping reading frames (see, e.g., FIG. 1).

There are four transcripts (that may be referred to herein as "genes" or "open reading frames") based on size, encoded by the HBV genome. These contain open reading frames called C, X, P, and S. The core protein is coded for by gene C (HBcAg). Hepatitis B e antigen (HBeAg) is produced by proteolytic processing of the pre-core (pre-C) protein. The DNA polymerase is encoded by gene P. Gene S is the gene that codes for the surface antigens (HBsAg). The HBsAg gene is one long open reading frame that contains three in frame "start" (ATG) codons resulting in polypeptides of three different sizes called large, middle, and small S antigens, pre-S1+pre-S2+S, pre-S2+S, or S. Surface antigens in addition to decorating the envelope of HBV, are also part of subviral particles, which are produced at large excess as compared to virion particles, and play a role in immune tolerance and in sequestering anti-HBsAg antibodies, thereby allowing for infectious particles to escape immune detection. The function of the non-structural protein coded for by gene X is not fully understood, but it plays a role in transcriptional transactivation and replication and is associated with the development of liver cancer.

HBV is one of the few DNA viruses that utilize reverse transcriptase in the replication process, which involves multiple stages including entry, uncoating, and transport of the virus genome to the nucleus. Initially, replication of the HBV genome involves the generation of an RNA intermediate that is then reverse transcribed to produce the DNA viral genome.

Upon infection of a cell with HBV, the viral genomic relaxed circular DNA (rcDNA) is transported into the cell nucleus and converted into episomal covalently closed circular DNA (cccDNA), which serves as the transcription template for the viral mRNAs. After transcription and nuclear export, cytoplasmic viral pregenomic RNA (pgRNA) is assembled with HBV polymerase and capsid proteins to form the nucleocapsid, inside which polymerase-catalyzed reverse transcription yields minus-strand DNA, which is subsequently copied into plus-strand DNA to form the progeny rcDNA genome. The mature nucleocapsids are then either packaged with viral envelope proteins to egress as virion particles or shuttled to the nucleus to amplify the cccDNA reservoir through the intracellular cccDNA amplification pathway. cccDNA is an essential component of the HBV replication cycle and is responsible for the establishment of infection and viral persistence.

HBV infection results in the production of two different particles: 1) the infectious HBV virus itself (or Dane particle), which includes a viral capsid assembled from the HBcAg and is covered by an envelope consisting of a lipid membrane with HBV surface antigens, and 2) subviral particles (or SVPs) that contain the small and medium forms of the hepatitis B surface antigen HBsAg, which are non-infectious. For each viral particle produced, over 10,000 SVPs are released into the blood. As such, SVPs (and the HBsAg protein they carry) represent the overwhelming majority of viral protein in the blood. HBV infected cells also secrete a soluble proteolytic product of the pre-core protein called the HBV e-antigen (HBeAg).

Eight genotypes of HBV, designated A to H, have been determined, and two additional genotypes I and J have been proposed, each having a distinct geographical distribution. The virus is non-cytopathic, with virus-specific cellular immunity being the main determinant for the outcome of exposure to HBV-acute infection with resolution of liver diseases with 6 months, or chronic HBV infection that is frequently associated with progressive liver injury.

The term "HBV" includes any of the genotypes of HBV (A to J). The complete coding sequence of the reference sequence of the HBV genome may be found in for example, GenBank Accession Nos. GI:21326584 (SEQ ID NO:1) and GI:3582357 (SEQ ID NO:3). Antisense sequences are provided in SEQ ID NO:2 and SEQ ID NO:4, respectively. Amino acid sequences for the C, X, P, and S proteins can be found, for example at NCBI Accession numbers YP_009173857.1 (C protein) (SEQ ID NO:37); YP_009173867.1 and BAA32912.1 (X protein) (SEQ ID Nos: 36 and 40); YP_009173866.1 and BAA32913.1 (P protein) (SEQ ID Nos:32 and 38); and YP_009173869.1, YP_009173870.1, YP_009173871.1, and BAA32914.1 (S protein) (SEQ ID NOs: 33, 34, 35, 39). Protein and DNA sequences from HBV genotype D, strain ayw are provided in SEQ ID NOs: 36-37. Protein and DNA sequences from HBV genotype C are provided in SEQ ID NOs: 38-39. Additional examples of HBV protein and DNA sequences, or their reverse complements, are provided in SEQ ID Nos: 41-49.

Additional examples of HBV mRNA sequences are readily available using publicly available databases, e.g., GenBank, UniProt, and OMIM. The International Repository for Hepatitis B Virus Strain Data can be accessed at http://www.hpa-bioinformatics.org.uk/HepSEQ/main.php.

The term "HBV," as used herein, also refers to naturally occurring DNA sequence variations of the HBV genome, e.g., Genotypes A-J and variants thereof.

As used herein, "Hepatitis D virus," used interchangeably with the term "HDV" refers to the well-known noncytopathic, liver-tropic DNA virus belonging to the Hepadnaviridae family. See, e.g., Ciancio and Rizzetto, Nat. Rev. 11:68-71, 2014; Le Gal et al., Emerg. Infect. Dis. 12:1447-1450, 2006; and Abbas and Afzal, World J. Hep., 5:666-675, 2013, all of which are incorporated by reference. Unless otherwise indicated, HDV refers to all clades and variants of HDV.

HDV produces one protein, namely HDAg. It comes in two forms; a 27 kDa large-HDAg (also referred to as lHD, L-HDAg, and large HDV antigen), and a small-HDAg of 24 kDa (also referred to as sHD, S-HDAg, and small HDV antigen). The N-terminals of the two forms are identical; they differ by 19 amino acids in the C-terminal of the large HDAg. Both isoforms are produced from the same reading frame, which contains an UAG stop codon at codon 196 and normally produces only the small-HDAg. However, editing by cellular enzyme adenosine deaminase-1 changes the stop codon to UCG, allowing the large-HDAg to be produced. Despite having 90% identical sequences, these two proteins play diverging roles during the course of an infection. HDAg-S is produced in the early stages of an infection and enters the nucleus and supports viral replication. HDAg-L, in contrast, is produced during the later stages of an infection, acts as an inhibitor of viral replication, and is required for assembly of viral particles.

Additional examples of HDV mRNA sequences are readily available using publicly available databases, e.g., Gen-Bank, UniProt, and OMIM.

The term "HDV," as used herein, also refers to naturally occurring DNA sequence variations of the HDV genome.

As used herein, the term "nucelot(s)ide analog" or "reverse transcriptase inhibitor" is an inhibitor of DNA replication that is structurally similar to a nucleotide or nucleoside and specifically inhibits replication of the HBV cccDNA and does not significantly inhibit the replication of the host (e.g., human) DNA. Such inhibitors include Tenofovir disoproxil fumarate (TDF), Tenofovir alafenamide (TAF), Lamivudine, Adefovir dipivoxil, Entecavir (ETV), Telbivudine, AGX-1009, emtricitabine, clevudine, ritonavir, dipivoxil, lobucavir, famvir, FTC, N-Acetyl-Cysteine (NAC), PC1323, theradigm-HBV, thymosin-alpha, ganciclovir, besifovir (ANA-380/LB-80380), and tenofvir-exaliades (TLX/CMX157). In certain embodiments, the nucelot(s)ide analog is Entecavir (ETV). Nucleot(s)ide analogs are commercially available from a number of sources and are used in the methods provided herein according to their label indication (e.g., typically orally administered at a specific dose) or as determined by a skilled practitioner in the treatment of HBV.

As used herein, "target sequence" refers to a contiguous portion of the nucleotide sequence of an mRNA molecule formed during the transcription of an HBV gene, including mRNA that is a product of RNA processing of a primary transcription product. In some embodiments, the target portion of the sequence will be at least long enough to serve as a substrate for dsRNA agent-directed cleavage at or near that portion of the nucleotide sequence of an mRNA molecule formed during the transcription of an HBV gene.

The target sequence may be about 19 to 21 nucleotides in length, e.g., 19, 20, or 21 nucleotides in length.

As used herein, the term "strand comprising a sequence" refers to an oligonucleotide comprising a chain of nucleotides that is described by the sequence referred to using the standard nucleotide nomenclature.

"G," "C," "A," "T" and "U" each generally stand for a nucleotide that contains guanine, cytosine, adenine, thymidine, and uracil as a base, respectively. However, it will be understood that the term "ribonucleotide" or "nucleotide" can also refer to a modified nucleotide, as further detailed below, or a surrogate replacement moiety (see, e.g., Table 1). The skilled person is well aware that guanine, cytosine, adenine, and uracil can be replaced by other moieties without substantially altering the base pairing properties of an oligonucleotide comprising a nucleotide bearing such replacement moiety. For example, without limitation, a nucleotide comprising inosine as its base can base pair with nucleotides containing adenine, cytosine, or uracil. Hence, nucleotides containing uracil, guanine, or adenine can be replaced in the nucleotide sequences of dsRNA featured in the present disclosure by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods featured in the present disclosure.

The terms "dsRNA agent", "RNAi agent," "iRNA agent," "iRNA," and "RNA interference agent" as used interchangeably herein, refer to an agent that contains RNA as that term is defined herein, and that mediates the targeted cleavage of an RNA transcript via an RNA-induced silencing complex (RISC) pathway. A dsRNA agent directs the sequence-specific degradation of mRNA through a process known as RNA interference (RNAi). The dsRNA agent modulates, e.g., inhibits, the expression of an HBV gene (e.g., one or more HBV genes) in a cell, e.g., a cell within a subject, such as a mammalian subject.

An "dsRNA agent" for use in the compositions, uses, and methods disclosed herein is a double stranded RNA and is referred to herein as a "dsRNA agent," "double stranded RNA agent," "double stranded RNA (dsRNA) molecule," "dsRNA," "iRNA," "iRNA agent," "dsRNAi agent," "RNAi agent," or "siRNA." The term "dsRNA" refers to a complex of ribonucleic acid molecules, having a duplex structure comprising two anti-parallel and substantially complementary nucleic acid strands, referred to as having "sense" and "antisense" orientations with respect to a target RNA, i.e., an HBV gene. In some embodiments of the present disclosure, a dsRNA triggers the degradation of a target RNA, e.g., an mRNA, through a post-transcriptional gene-silencing mechanism referred to herein as RNA interference or RNAi.

In general, each strand of a dsRNA molecule may contain ribonucleotides, but as described in detail herein, each or both strands can also include one or more non-ribonucleotides, e.g., a deoxyribonucleotide or a modified nucleotide. In addition, as used in this specification, a "dsRNA agent" may include ribonucleotides with chemical modifications; a dsRNA agent may include substantial modifications at multiple nucleotides. As used herein, the term "modified nucleotide" refers to a nucleotide having, independently, a modified sugar moiety, a modified internucleotide linkage, or modified nucleobase. Thus, the term modified nucleotide encompasses substitutions, additions, or removal of, e.g., a functional group or atom, to internucleoside linkages, sugar moieties, or nucleobases. The modifications suitable for use in the agents of the present disclosure include all types of modifications disclosed herein or known in the art. Any such modifications, as used in a dsRNA agent-type molecule, are encompassed by "dsRNA agent" for the purposes of this specification and claims.

The term "inhibiting," as used herein, is used interchangeably with "reducing," "silencing," "downregulating", "suppressing", and other similar terms, and includes any level of inhibition. Preferably inhibiting includes a statistically significant or clinically significant inhibition.

The phrase "inhibiting expression of HBV" or "inhibiting expression of an HBV gene" as used herein, includes inhibition of expression of any HBV gene (e.g., an HBV gene expressed from HBV in an HBV viral infection, an HBV gene expressed from an expression construct in a cell) as well as variants or mutants of an HBV gene that encode an HBV protein. The terms include knockdown of any HBV transcript (e.g., 3.5 kb, 2.4 kb, 2.1 kb, or 0.7 kb transcript)

encoding one or more HBV viral protein (such as, e.g., preS1/2-S, preS, S, P, X, preC, and C), as well as variants or mutants of an HBV gene.

"Inhibiting expression of an HBV gene" includes any level of inhibition of an HBV gene or transcript, e.g., at least partial suppression of the expression of an HBV gene, e.g. HBV gene S, P, X, or C, or any combination thereof, e.g., S, P, and C. The expression of the HBV gene may be assessed based on the level, or the change in the level, of any variable associated with HBV gene expression, e.g., an HBV mRNA level or an HBV protein level, or HBV cccDNA level. This level may be assessed in an individual cell or in a group of cells, including, for example, a sample derived from a subject, e.g., levels may be monitored in serum. Inhibition may be assessed by a decrease in an absolute or relative level of one or more of these variables compared with a control level. The control level may be any type of control level that is utilized in the art, e.g., a pre-dose baseline level, or a level determined from a similar subject or population average from an appropriate control subject, cell, or sample that is untreated or treated with a control (e.g., buffer only control or inactive agent control).

In some embodiments of the methods of the present disclosure, expression of an HBV gene is inhibited by at least 80%, 85%, 90%, 95%, e.g., in a subject by at least 1 log 10, 2 log 10, 3 log 10, or 4 log 10, or to below the level of detection of the assay. In preferred embodiments, the inhibition of expression of an HBV gene in a subject results in a clinically relevant inhibition of the level of gene expression, e.g., sufficiently inhibited to permit an effective immune response against an HBV protein, either when administered alone or in combination with other agents to promote or potentiate an immune response.

In an in vitro cell-based assay or expression of a heterologous gene in an in vivo model, e.g., the mouse AAV-hHBV model provided herein, inhibition of total HBV expression by at least 90% is preferred, e.g., at least 1 log 10, 2 log 10, or 3 log 10. In treatment of a subject with an HBV infection, a decrease of at least 90% of the HBV gene or protein level, i.e., the difference in the HBV gene or protein level before and after treatment, is preferred. More than one dose may be required to achieve the desired level of inhibition.

Inhibition of the expression of an HBV gene may be manifested by a reduction of the amount of RNA expressed by a first cell or group of cells (such cells may be present, for example, in a sample derived from a subject) in which an HBV gene is transcribed and which has or have been treated (e.g., by contacting the cell or cells with an dsRNA agent of the present disclosure, or by administering an dsRNA agent of the present disclosure to a subject in which the cells are or were present) such that the expression of an HBV gene is inhibited, as compared to a second cell or group of cells substantially identical to the first cell or group of cells but which has not or have not been so treated (control cell(s)). In preferred embodiments, the inhibition is assessed by the rtPCR method provided in Example 2 of WO2016/077321 (which method is incorporated herein by reference), with in vitro assays being performed in an appropriately matched cell line with the duplex at a 10 nM concentration, and expressing the level of mRNA in treated cells as a percentage of the level of mRNA in control cells, using the following formula:

$$\frac{(mRNA \text{ in control cells}) - (mRNA \text{ in treated cells})}{(mRNA \text{ in control cells})} \cdot 100\%$$

Alternatively, inhibition of the expression of an HBV gene may be assessed in terms of a reduction of a parameter that is functionally linked to HBV gene expression. HBV gene silencing may be determined in any cell expressing an HBV gene, either constitutively or by genomic engineering, and by any assay known in the art.

Inhibition of the expression of an HBV protein may be manifested by a reduction in the level of an HBV protein that is expressed by a cell or group of cells (e.g., the level of protein expressed in a sample derived from a subject). As explained above, for the assessment of mRNA suppression, the inhibition of protein expression levels in a treated cell or group of cells may similarly be expressed as a percentage of the level of protein in a control cell or group of cells or in serum.

A control cell or group of cells that may be used to assess the inhibition of the expression of an HBV gene includes a cell or group of cells that has not yet been contacted with a dsRNA agent of the present disclosure. For example, the control cell or group of cells may be derived from an individual subject (e.g., a human or animal subject) prior to treatment of the subject with a dsRNA agent. In alternative embodiments, the level may be compared to an appropriate control sample, e.g., a known population control sample.

The level of HBV RNA that is expressed by a cell or group of cells, or the level of circulating HBV RNA, may be determined using any method known in the art for assessing mRNA expression, preferably using the rtPCR method provided in Example 2 of WO2016/077321. In some embodiments, the level of expression of an HBV gene (e.g., total HBV RNA, an HBV transcript, e.g., HBV 3.5 kb transcript) in a sample is determined by detecting a transcribed polynucleotide, or portion thereof, e.g., RNA of the HBV gene. RNA may be extracted from cells using RNA extraction techniques including, for example, using acid phenol/guanidine isothiocyanate extraction (RNAzol B; Biogenesis), RNeasy RNA preparation kits (Qiagen®) or PAXgene (Pre-Analytix, Switzerland). Typical assay formats utilizing ribonucleic acid hybridization include nuclear run-on assays, RT-PCR, RNase protection assays (Melton et al., *Nuc. Acids Res.* 12:7035), northern blotting, in situ hybridization, and microarray analysis. Circulating HBV mRNA may be detected using methods the described in WO 2012/177906, which methods are hereby incorporated herein by reference.

In some embodiments, the level of expression of an HBV gene is determined using a nucleic acid probe. The term "probe," as used herein, refers to any molecule that is capable of selectively binding to a specific HBV gene. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Isolated RNA can be used in hybridization or amplification assays that include, but are not limited to, northern analyses, polymerase chain reaction (PCR) analyses, and probe arrays. One method for the determination of mRNA levels involves contacting the isolated mRNA with a nucleic acid molecule (probe) that can hybridize to an HBV mRNA. In some embodiments, the mRNA is immobilized on a solid surface and contacted with a probe, for example by running the isolated mRNA on an agarose gel and transferring the mRNA from the gel to a membrane, such as nitrocellulose. In some other embodiments, the probe(s) are immobilized on a solid surface and the mRNA is contacted with the probe(s), for example, in an Affymetrix® gene chip array. A skilled artisan can readily adapt known mRNA detection methods for use in determining the level of an HBV mRNA.

An alternative method for determining the level of expression of an HBV gene in a sample involves the process of nucleic acid amplification or reverse transcriptase (to prepare cDNA) of for example mRNA in the sample, e.g., by RT-PCR (the experimental embodiment set forth in Mullis, 1987, U.S. Pat. No. 4,683,202), ligase chain reaction (Barany (1991) *Proc. Natl. Acad. Sci. USA* 88:189-193), self-sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), rolling circle replication (Lizardi et al., U.S. Pat. No. 5,854,033), or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the present disclosure, the level of expression of an HBV gene is determined by quantitative fluorogenic RT-PCR (i.e., the TaqMan™ System), e.g., using the method provided herein.

The expression levels of an HBV RNA may be monitored using a membrane blot (such as used in hybridization analysis such as northern, dot, and the like), or microwells, sample tubes, gels, beads, or fibers (or any solid support comprising bound nucleic acids). See U.S. Pat. Nos. 5,770,722, 5,874,219, 5,744,305, 5,677,195, and 5,445,934, which are incorporated herein by reference for teachings relevant to such methods. The determination of HBV expression level may also comprise using nucleic acid probes in solution.

In preferred embodiments, the level of RNA expression is assessed using real time PCR (qPCR). The use of these methods is described and exemplified in Example 2 of WO2016/077321.

The level of HBV protein expression may be determined using any method known in the art for the measurement of protein levels. Such methods include, for example, electrophoresis, capillary electrophoresis, high performance liquid chromatography (HPLC), thin layer chromatography (TLC), hyperdiffusion chromatography, fluid or gel precipitating reactions, absorption spectroscopy, a colorimetric assays, spectrophotometric assays, flow cytometry, immunodiffusion (single or double), immunoelectrophoresis, western blotting, radioimmunoassay (RIA), enzyme-linked immunosorbent assays (ELISAs), immunofluorescent assays, electrochemiluminescence assays, and the like.

dsRNA Agents

The duplex region may be of any length that permits specific degradation of a desired target RNA through a RISC pathway, and may range from about 19-21 base pairs in length, for example, about 19, 20, or 21 base pairs in length. Exemplary dsRNA agents provided herein include duplex lengths of 19-21 base pair.

Where the two substantially complementary strands of a dsRNA are comprised by separate RNA molecules, those molecules need not, but can be covalently connected. Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, a dsRNA agent may comprise one or more nucleotide overhangs.

As used herein, the term "nucleotide overhang" refers to at least one unpaired nucleotide that protrudes from the duplex structure of a double stranded dsRNA agent. For example, when a 3'-end of one strand of a dsRNA extends beyond the 5'-end of the other strand, or vice versa, there is a nucleotide overhang. A dsRNA can comprise an overhang of at least one nucleotide; alternatively the overhang can comprise two nucleotides. A nucleotide overhang can comprise or consist of a nucleotide/nucleoside analog, including a deoxynucleotide/nucleoside. The overhang(s) can be on the sense strand, the antisense strand, or any combination thereof. Furthermore, the nucleotide(s) of an overhang can be present on the 5'-end, 3'-end, or both ends of either an antisense or sense strand of a dsRNA. In a preferred embodiment, the nucleotide overhang is on the 3' end of the antisense strand.

"Blunt" or "blunt end" means that there are no unpaired nucleotides at that end of the double stranded dsRNA agent, i.e., no nucleotide overhang. A "blunt ended" dsRNA agent is a dsRNA that is double stranded over its entire length, i.e., no nucleotide overhang at either end of the molecule. In some embodiments, the dsRNA agents of the present disclosure include dsRNA agents with nucleotide overhangs at one end (i.e., agents with one overhang and one blunt end) or with nucleotide overhangs at both ends.

The term "antisense strand" or "guide strand" refers to the strand of a dsRNA agent, which includes a region that is substantially complementary to a target sequence, e.g., a HBV mRNA. As used herein, the term "region of complementarity" refers to the region on the antisense strand that is substantially complementary to a sequence, for example a target sequence, e.g., an HBV nucleotide sequence, as defined herein. Where the region of complementarity is not fully complementary to the target sequence, the mismatches can be in the internal or terminal regions of the molecule. Generally, the most tolerated mismatches are in the terminal regions, e.g., within 5, 4, 3, 2, or 1 nucleotides of the 5'- or 3'-terminus of the dsRNA agent. In some embodiments, a dsRNA agent of the present disclosure includes a nucleotide mismatch in the antisense strand. In some embodiments, a dsRNA agent of the present disclosure includes a nucleotide mismatch in the sense strand. In some embodiments, the nucleotide mismatch is, for example, within 5, 4, 3, 2, or 1 nucleotides from the 3'-terminus of the dsRNA agent. In some embodiments, the nucleotide mismatch is, for example, in the 3'-terminal nucleotide of the dsRNA agent.

The term "sense strand" or "passenger strand" as used herein, refers to the strand of a dsRNA agent that includes a region that is substantially complementary to a region of the antisense strand as that term is defined herein.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions can include: 400 mM NaCl, 40 mM PIPES pH 6.4, 1 mM EDTA, 50° C. or 70° C. for 12-16 hours followed by washing (see, e.g., "Molecular Cloning: A Laboratory Manual, Sambrook, et al. (1989) Cold Spring Harbor Laboratory Press). Other conditions, such as physiologically relevant conditions as can be encountered inside an organism, can apply. The skilled person will be able to determine the set of conditions most appropriate for a test of complementarity of two sequences in accordance with the ultimate application of the hybridized nucleotides.

Complementary sequences within a dsRNA agent, e.g., within a dsRNA agent as described herein, include base-pairing of the oligonucleotide or polynucleotide comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they can form one or more, but generally not more than 4, 3, or 2 mismatched base pairs upon hybridization for a duplex up to 21 base pairs, while retaining the ability to hybridize under the conditions most relevant to their ultimate application, e.g., inhibition of gene expression via a RISC pathway. However, where two oligonucleotides are designed to form, upon hybridization, one or more single stranded overhangs, such overhangs shall not be regarded as mismatches with regard to the determination of complementarity. For example, a dsRNA agent comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, can yet be referred to as "fully complementary" for the purposes described herein.

"Complementary" sequences, as used herein, can also include, or be formed entirely from, non-Watson-Crick base pairs or base pairs formed from non-natural and modified nucleotides, in so far as the above requirements with respect to their ability to hybridize are fulfilled. Such non-Watson-Crick base pairs include, but are not limited to, G:U Wobble or Hoogstein base pairing.

The terms "complementary," "fully complementary," and "substantially complementary" herein can be used with respect to the base matching between the sense strand and the antisense strand of a dsRNA, or between the antisense strand of a dsRNA agent and a target sequence, as will be understood from the context of their use. It is understood that multiple HBV genotypes are known. Therefore, a dsRNA agent designed to be fully complementary to one HBV genotype may not be fully complementary to all HBV genotypes. A dsRNA agent targeted to a specific site is effective at target knockdown across multiple genotypes without being fully complementary across all genotypes.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding an HBV gene). For example, a polynucleotide is complementary to at least a part of an HBV mRNA if the sequence is substantially complementary to a non-interrupted portion of an mRNA encoding an HBV gene.

Accordingly, in some embodiments, the antisense strand polynucleotides disclosed herein are fully complementary to the target HBV sequence. In some other embodiments, the antisense strand polynucleotides disclosed herein are substantially complementary to the target HBV sequence and comprise a contiguous nucleotide sequence that is at least 80% complementary over its entire length to the equivalent region of the nucleotide sequence of SEQ ID NO:1, or a fragment of SEQ ID NO:1, such as at least 80%, 85%, 90%, or 95% complementary.

In some embodiments, a dsRNA agent of the present disclosure includes a sense strand that is substantially complementary to an antisense polynucleotide which, in turn, is complementary to a target HBV sequence, and wherein the sense strand polynucleotide comprises a contiguous nucleotide sequence that is at least 80% complementary over its entire length to the equivalent region of the nucleotide sequence of SEQ ID NO:2, such as at least 85%, 90%, or 95% complementary.

In some embodiments, a dsRNA agent includes an antisense strand that is substantially complementary to the target HBV sequence and comprises a contiguous nucleotide sequence that is at least 80% complementary over its entire length to the equivalent region of the nucleotide sequence of any one of the sense nucleotide sequences in Table 2, or a fragment of any one of the sense nucleotide sequences in Table 2, such as at least 85%, 90%, or 95% complementary.

As described in detail herein, each or both strands can also include one or more non-ribonucleotides, e.g., a deoxyribonucleotide or a modified nucleotide. In addition, a dsRNA agent may include ribonucleotides with chemical modifications. Such modifications may include all types of modifications disclosed herein or known in the art. Any such modifications, as used in a dsRNA agent, may be encompassed by "dsRNA agent" for the purposes of this specification and claims.

In some embodiments, the majority of nucleotides of each strand are ribonucleotides, but as described in detail herein, each or both strands can also include one or more non-ribonucleotides, e.g., a deoxyribonucleotide or a modified nucleotide. In addition, a dsRNA agent may include ribonucleotides with chemical modifications. Such modifications may include all types of modifications disclosed herein or known in the art. Any such modifications, as used in a dsRNA agent, are encompassed by "dsRNA agent" and "dsRNA agent" for the purposes of this specification and claims.

The term "lower" in the context of the level of HBV gene expression or HBV protein production in a subject, or a disease marker or symptom refers to a statistically significant decrease in such level. The decrease can be, for example, at least 80%, 85%, 90%, or 95%, or below the level of detection for the detection method, or more towards or to a normal level (which may or may not be zero). In monitoring of HBV infection, a log 10 scale is typically used to describe the level of antigenemia (e.g., HBsAg level in serum) or viremia (HBV DNA level in serum). It is understood that 1 log 10 decrease is a 90% decrease (10% remaining), a 2 log 10 decrease is a 99% decrease (1% remaining), etc. In certain embodiments, a disease marker is lowered to below the level of detection. In certain embodiments, the methods include a clinically relevant inhibition of expression of HBV, e.g., as demonstrated by a clinically relevant outcome after treatment of a subject with an agent to reduce the expression of HBV. In some embodiments, at least partial suppression of the expression of an HBV gene, is assessed by a reduction of the amount of HBV mRNA, which can be isolated from or detected in a first cell or group of cells in which an HBV gene is transcribed and which has or have been treated such that the expression of an HBV gene is inhibited, as compared to a second cell or group of cells substantially identical to the first cell or group of cells but which has or have not been so treated (control cells).

In certain embodiments, "lower" or "reduce" is understood as lowering or reducing a level towards or to a normal level, i.e., normalizing a level. In certain embodiments, the expression of the target is normalized to a level accepted as within the range of normal for an individual without such disorder, e.g., the level of a disease marker, such as, ALT or AST, is decreased to a level accepted as within the range of normal for an individual without such disorder. When the disease associated level is elevated from the normal level, the change is calculated from the upper level of normal (ULN). When the disease associated level is decreased from the normal level, the change is calculated from the lower level of normal (LLN). The lowering is the percent difference in the change between the subject value and the normal value. For example, a normal AST level can be reported as 10 to 40 units per liter. If a subject with an AST level of 200 units per liter, i.e., 5 times the ULN, 160 units per liter above the upper level of normal prior to treatment has an AST level of 120 units per liter, i.e., 3 times the ULN, 80 units per liter above the upper level of normal after treatment, the elevated AST would be lowered towards normal by 50% (80/160).

As another example, a normal ALT level is typically considered to be 7 to 55 units per liter (U/L), making the upper level of normal 55 U/L. A subject with an ALT level of 100 U/L prior to treatment (45 U/L over the upper level of normal) and 75 U/L after treatment (decreased by 25 U/L), the subject's ALT is lowered towards a normal level by 55% (25/45×100%). As used herein, if a disease is associated with an elevated value for a symptom, "normal" is considered to be the upper level of normal. If a disease is associated with a decreased value for a symptom, "normal" is considered to be the lower level of normal.

The phrase "contacting a cell with a dsRNA agent," such as a dsRNA, as used herein, includes contacting a cell by any possible means. Contacting a cell with a dsRNA agent includes contacting a cell in vitro with the dsRNA agent or contacting a cell in vivo with the dsRNA agent. The contacting may be done directly or indirectly. Thus, for example, the dsRNA agent may be put into physical contact with the cell by the individual performing the method, or alternatively, the dsRNA agent may be put into a situation that will permit or cause it to subsequently come into contact with the cell.

Contacting a cell in vitro may be done, for example, by incubating the cell with the dsRNA agent. Contacting a cell in vivo may be done, for example, by injecting the dsRNA agent into or near the tissue where the cell is located, or by injecting the dsRNA agent into another area, e.g., the bloodstream or the subcutaneous space, such that the agent will subsequently reach the tissue where the cell to be contacted is located. For example, the dsRNA agent may contain or be coupled to a ligand, e.g., GalNAc$_3$, that directs the dsRNA agent to a site of interest, e.g., the liver. Combinations of in vitro and in vivo methods of contacting are also possible. For example, a cell may also be contacted in vitro with a dsRNA agent and subsequently transplanted into a subject.

In some embodiments, contacting a cell with a dsRNA agent includes "introducing" or "delivering the dsRNA agent into the cell" by facilitating or effecting uptake or absorption into the cell. Absorption or uptake of a dsRNA agent can occur through unaided diffusive or active cellular processes, or by auxiliary agents or devices. Introducing a dsRNA agent into a cell may be in vitro or in vivo. For example, for in vivo introduction, dsRNA agent can be injected into a tissue site or administered systemically. In vitro introduction into a cell includes methods known in the art such as electroporation and lipofection. Further approaches are described herein below or are known in the art.

As used herein, a "subject" is an animal, such as a mammal, including any mammal that can be infected with HBV, e.g., a primate (such as a human, a non-human primate, e.g., a monkey, or a chimpanzee), or an animal that is considered an acceptable clinical model of HBV infection, HBV-AAV mouse model (see, e.g., Yang et al. (2014) Cell and Mol Immunol 11:71) or the HBV 1.3×fs transgenic mouse model (Guidotti et al. (1995) J. Virol. 69:6158). In some embodiments, the subject has a hepatitis B virus (HBV) infection. In some embodiments, the subject has both a hepatitis B virus (HBV) infection and a hepatitis D virus (HDV) infection. In some embodiments, the subject is a human, such as a human being having an HBV infection, especially a chronic hepatitis B virus (HBV) infection.

As used herein, the terms "treating" or "treatment" refer to a beneficial or desired result including, but not limited to, alleviation or amelioration of one or more signs or symptoms associated with unwanted HBV gene expression or HBV replication, e.g., the presence of serum or liver HBV cccDNA; the presence of serum HBV DNA; the presence of serum or liver HBV antigen, e.g., HBsAg or HBeAg; elevated ALT; elevated AST (normal range is typically considered about 10 to 34 U/L); the absence or low level of anti-HBV antibodies, a liver injury; cirrhosis; delta hepatitis, acute hepatitis B; acute fulminant hepatitis B; chronic hepatitis B; liver fibrosis; end-stage liver disease; hepatocellular carcinoma; serum sickness-like syndrome; anorexia; nausea; vomiting, low-grade fever; myalgia; fatigability; disordered gustatory acuity and smell sensations (aversion to food and cigarettes); right upper quadrant and epigastric pain (intermittent, mild to moderate); hepatic encephalopathy; somnolence; disturbances in sleep pattern; mental confusion; coma; ascites; gastrointestinal bleeding; coagulopathy; jaundice; hepatomegaly (mildly enlarged, soft liver); splenomegaly; palmar erythema; spider nevi; muscle wasting; spider angiomas; vasculitis; variceal bleeding; peripheral edema; gynecomastia; testicular atrophy; abdominal collateral veins (caput medusa); ALT levels higher than AST levels; elevated gamma-glutamyl transpeptidase (GGT) (normal range is typically considered about 8 to 65 U/L) and alkaline phosphatase (ALP) levels (normal range is typically considered about 44 to 147 IU/L (international units per liter), not more than 3 times the ULN); slightly low albumin levels; elevated serum iron levels; leukopenia (i.e., granulocytopenia); lymphocytosis; increased erythrocyte sedimentation rate (ESR); shortened red blood cell survival; hemolysis; thrombocytopenia; a prolongation of the international normalized ratio (INR); presence of serum or liver HBsAg, HBeAg, or Hepatitis B core antibody (anti-HBc) immunoglobulin M (IgM); presence of hepatitis B surface antibody (anti-HBs), hepatitis B e antibody (anti-HBe), or HBV DNA; increased bilirubin levels; hyperglobulinemia; the presence of tissue-nonspecific antibodies, such as anti-smooth muscle antibodies (ASMAs) or antinuclear antibodies (ANAs) (10-20%); the presence of tissue-specific antibodies, such as antibodies against the thyroid gland (10-20%); elevated levels of rheumatoid factor (RF); low platelet and white blood cell counts; lobular, with degenerative and regenerative hepatocellular changes, and accompanying inflammation; and predominantly centrilobular necrosis, whether detectable or undetectable. The likelihood of developing liver fibrosis, is reduced, for example, when an individual having one or more risk factors for liver fibrosis, e.g., chronic hepatitis B infection, either fails to develop liver fibrosis or develops liver fibrosis with less severity relative to a population having the same risk factors and not receiving treatment as described herein. The failure to develop a disease, disorder, or condition, or the reduction in the development of a sign or symptom associated with such a disease, disorder, or condition (e.g., by a clinically relevant amount), or the exhibition of delayed signs or symptoms delayed (e.g., by days, weeks, months, or years) is considered effective prevention. "Treatment" can also mean prolonging survival as compared to expected survival in the absence of treatment. Prevention may require the administration of more than one dose.

In preferred embodiments, treatment of HBV infection results in a "functional cure" of hepatitis B. As used herein, functional cure is understood as clearance of circulating HBsAg and is preferably accompanied by conversion to a status in which HBsAg antibodies become detectable using a clinically relevant assay. For example, detectable antibodies can include a signal higher than 10 mIU/ml as measured by Chemiluminescent Microparticle Immunoassay (CMIA) or any other immunoassay called anti-HBs seroconversion. Functional cure does not require clearance of all replicative forms of HBV (e.g., cccDNA from the liver). Anti-HBs seroconversion occurs spontaneously in about 0.2-1% of chronically infected patients per year. However, even after anti-HBs seroconversion, low level persistence of HBV is observed for decades indicating that a functional rather than a complete cure occurs. Without being bound to mechanism, it is proposed that the immune system is able to keep HBV in check. A functional cure permits discontinuation of any treatment for the HBV infection. However, it is understood that a "functional cure" for HBV infection may not be sufficient to prevent or treat diseases or conditions that result from HBV infection, e.g., liver fibrosis, HCC, cirrhosis.

As used herein, the term "Hepatitis B virus-associated disease" or "HBV-associated disease," is a disease or disorder that is caused by, or associated with HBV infection or replication. The term "HBV-associated disease" includes a disease, disorder, or condition that would benefit from reduction in HBV gene expression or replication. Non-limiting examples of HBV-associated diseases include, for example, hepatitis D virus infection, delta hepatitis, acute hepatitis B; acute fulminant hepatitis B; chronic hepatitis B; liver fibrosis; end-stage liver disease; and hepatocellular carcinoma.

In some embodiments, an HBV-associated disease is hepatitis D virus infection. Hepatitis D virus or hepatitis delta virus (HDV) is a human pathogen. However, the virus is defective and depends on obligatory helper functions provided by hepatitis B virus (HBV) for transmission; indeed, HDV requires an associated or pre-existing HBV infection to become infectious and thrive, in particular, the viral envelope containing the surface antigen of hepatitis B. HDV can lead to severe acute and chronic forms of liver disease in association with HBV. Hepatitis D infection or delta hepatitis is highly endemic to several African countries, the Amazonian region, and the Middle East, while its prevalence is low in industrialized countries, except in the Mediterranean.

Transmission of HDV can occur either via simultaneous infection with HBV (coinfection) or superimposed on chronic hepatitis B or hepatitis B carrier state (superinfection). Both superinfection and coinfection with HDV results in more severe complications compared to infection with HBV alone. These complications include a greater likelihood of experiencing liver failure in acute infections and a rapid progression to liver cirrhosis, with an increased chance of developing liver cancer in chronic infections. In combination with hepatitis B virus, hepatitis D has the highest fatality rate of all the hepatitis infections, at 20%.

In some embodiments, an HBV-associated disease is acute hepatitis B. Acute hepatitis B includes inflammation of the liver that lasts less than six months. Typical symptoms of acute hepatitis B are fatigue, anorexia, nausea, and vomiting. Very high aminotransferase values (>1000 U/L) and hyperbilirubinemia are often observed. Severe cases of acute hepatitis B may progress rapidly to acute liver failure, marked by poor hepatic synthetic function. This is often defined as a prothrombin time (PT) of 16 seconds or an international normalized ratio (INR) of 1.5 in the absence of previous liver disease. Acute hepatitis B may evolve into chronic hepatitis B.

In some embodiments, an HBV-associated disease is chronic hepatitis. Chronic hepatitis B (CHB) includes inflammation of the liver that lasts more than six months. Subjects having CHB are HBsAg positive and have either high viremia (≥104 HBV-DNA copies/ml blood) or low viremia (<103 HBV-DNA copies/ml blood). In some embodiments, subjects have been infected with HBV for at least five years. In some embodiments, subjects have been infected with HBV for at least ten years. In some embodiments, subjects became infected with HBV at birth. Subjects having chronic hepatitis B disease can be immune tolerant or have an inactive chronic infection without any evidence of active disease, and they are also asymptomatic. Patients with chronic active hepatitis, especially during the replicative state, may have symptoms similar to those of acute hepatitis. Subjects having chronic hepatitis B disease may have an active chronic infection accompanied by necroinflammatory liver disease, have increased hepatocyte turn-over in the absence of detectable necroinflammation, or have an inactive chronic infection without any evidence of active disease, and they are also asymptomatic. The persistence of HBV infection in CHB subjects is the result of cccHBV DNA. In some embodiments, a subject having CHB is HBeAg positive. In another embodiment, a subject having CHB is HBeAg negative. Subjects having CHB have a level of serum HBV DNA of less than 105 and a persistent elevation in transaminases, for examples ALT, AST, and gamma-glutamyl transferase. A subject having CHB may have a liver biopsy score of less than 4 (e.g., a necroinflammatory score).

In some embodiments, an HBV-associated disease is acute fulminant hepatitis B. A subject having acute fulminant hepatitis B has symptoms of acute hepatitis and the additional symptoms of confusion or coma (due to the liver's failure to detoxify chemicals) and bruising or bleeding (due to a lack of blood clotting factors).

Subjects having an HBV infection, e.g., CHB, may develop liver fibrosis. Accordingly, in some embodiments, an HBV-associated disease is liver fibrosis. Liver fibrosis, or cirrhosis, is defined histologically as a diffuse hepatic process characterized by fibrosis (excess fibrous connective tissue) and the conversion of normal liver architecture into structurally abnormal nodules.

Subjects having an HBV infection, e.g., CHB, may develop end-stage liver disease. Accordingly, in some embodiments, an HBV-associated disease is end-stage liver disease. For example, liver fibrosis may progress to a point where the body may no longer be able to compensate for, e.g., reduced liver function, as a result of liver fibrosis (i.e., decompensated liver), and result in, e.g., mental and neurological symptoms and liver failure.

Subjects having an HBV infection, e.g., CHB, may develop hepatocellular carcinoma (HCC), also referred to as malignant hepatoma. Accordingly, in some embodiments, an HBV-associated disease is HCC. HCC commonly develops in subjects having CHB and may be fibrolamellar, pseudoglandular (adenoid), pleomorphic (giant cell), or clear cell.

An "HDV-associated disorder" or a Hepatitis D-virus-associated disorder" is a disease or disorder associated with expression of an HDV. Exemplary HDV-associated disorders include hepatitis B virus infection, acute hepatitis B, acute hepatitis D; acute fulminant hepatitis D; chronic hepatitis D; liver fibrosis; end-stage liver disease; and hepatocellular carcinoma.

"Therapeutically effective amount," as used herein, is intended to include the amount of an dsRNA agent that, when administered to a patient for treating a subject having an HBV infection or HBV-associated disease, is sufficient to effect treatment of the disease (e.g., by diminishing or maintaining the existing disease or one or more symptoms of disease). The "therapeutically effective amount" may vary depending on the dsRNA agent, how the agent is administered, the disease and its severity, and the history, age, weight, family history, genetic makeup, stage of pathological processes mediated by HBV gene expression, the types of preceding or concomitant treatments, if any, and other individual characteristics of the patient to be treated. A therapeutically effective amount may require the administration of more than one dose.

A "therapeutically-effective amount" also includes an amount of a dsRNA agent that produces some desired effect at a reasonable benefit/risk ratio applicable to any treatment. dsRNA agents employed in the methods of the present disclosure may be administered in a sufficient amount to produce a reasonable benefit/risk ratio applicable to such treatment.

The term "sample," as used herein, includes a collection of similar fluids, cells, or tissues isolated from a subject, as well as fluids, cells, or tissues present within a subject. Examples of biological fluids include blood, serum, and serosal fluids, plasma, lymph, urine, saliva, and the like. Tissue samples may include samples from tissues, organs, or localized regions. For example, samples may be derived from particular organs, parts of organs, or fluids or cells within those organs. In certain embodiments, samples may be derived from the liver (e.g., whole liver or certain segments of liver or certain types of cells in the liver, such as, e.g., hepatocytes). In preferred embodiments, a "sample derived from a subject" refers to blood, or plasma or serum obtained from blood drawn from the subject. In further embodiments, a "sample derived from a subject" refers to liver tissue (or subcomponents thereof) or blood tissue (or subcomponents thereof, e.g., serum) derived from the subject.

II. dsRNA Agents

The present disclosure provides dsRNA agents that inhibit the expression of one or more HBV genes. In some embodiments, the dsRNA agent includes double stranded ribonucleic acid (dsRNA) molecules for inhibiting the expression of an HBV gene in a cell, such as a cell within a subject, e.g., a mammal, such as a human having an HBV-associated disease, e.g., chronic hepatitis B. The dsRNA agents include an antisense strand having a region of complementarity that is complementary to at least a part of an mRNA formed in the expression of an HBV gene. The region of complementarity is about 19-21 nucleotides in length. Upon contact with a cell expressing the HBV gene, the dsRNA agent inhibits the expression of the HBV gene by at least 80% as assayed by, for example, a PCR or branched DNA (bDNA)-based method, or by a protein-based method, such as by immunofluorescence analysis, using, for example, western blotting or flowcytometric techniques. In preferred embodiments, percent inhibition is determined using the real time PCR method provided in Example 2 using a cell line provided therein with the dsRNA agent used at a 10 nM concentration in the transfection.

A dsRNA includes two RNA strands that are complementary and hybridize to form a duplex structure under conditions in which the dsRNA will be used. One strand of a dsRNA (the antisense strand) includes a region of complementarity that is substantially complementary, and generally fully complementary, to a target sequence. However, due to sequence variations among HBV genotypes, the dsRNA may be fully complementary to some, but not all, HBV genotypes. The target sequence can be derived from the sequence of an mRNA formed during the expression of an HBV gene. The other strand (the sense strand) includes a region that is complementary to the antisense strand, such that the two strands hybridize and form a duplex structure when combined under suitable conditions. As described elsewhere herein and as known in the art, the complementary sequences of a dsRNA can also be contained as self-complementary regions of a single nucleic acid molecule, as opposed to being on separate oligonucleotides.

Generally, the duplex structure is 19-21 base pairs in length, e.g., 19, 20, or 21 base pairs in length.

Similarly, the region of complementarity to the target sequence is 19-23 nucleotides in length, e.g., 19-23, 19-22, 19-21, 19-20, 20-23, 20-22, 20-21, 21-22, 19, 20, 21, 22, or 23 nucleotides in length. In some embodiments, the region of complementarity is 21 nucleotides in length. As the ordinarily skilled person will also recognize, the region of an RNA targeted for cleavage will most often be part of a larger RNA molecule, often an mRNA molecule. Where relevant, a "part" of an mRNA target is a contiguous sequence of an mRNA target of sufficient length to allow it to be a substrate for RNAi-directed cleavage (i.e., cleavage through a RISC pathway).

One of skill in the art will also recognize that the duplex region is a primary functional portion of a dsRNA, e.g., a duplex region of about 19-21 base pairs, e.g., 19-21, 19-20, 20-21, 19, 20, or 21 base pairs. In some embodiments, the duplex region is 19 base pairs.

A dsRNA as described herein can further include one or more single-stranded nucleotide overhangs, e.g., 1 or 2 nucleotides. A nucleotide overhang can comprise or consist of a nucleotide/nucleoside analog, including a deoxynucleotide/nucleoside. The overhang(s) can be on the sense strand, the antisense strand, or any combination thereof. Furthermore, the nucleotide(s) of an overhang can be present on the 5'-end, 3'-end, or both ends of one or both of an antisense or sense strand of a dsRNA. In some embodiments, the dsRNA includes a 2-nucleotide overhang on the 3' end of the antisense strand.

A dsRNA can be synthesized by standard methods known in the art as further discussed below, e.g., by use of an automated DNA synthesizer, such as are commercially available from, for example, Biosearch, Applied Biosystems™, Inc. Methods for synthesis of dsRNAs for use in pharmaceutical compositions are also known in the art.

dsRNA agent compounds of the present disclosure may be prepared using a two-step procedure. First, the individual strands of the double stranded RNA molecule are prepared separately. Then, the component strands are annealed. The individual strands of the dsRNA agent compound can be prepared using solution-phase or solid-phase organic synthesis or both. Organic synthesis offers the advantage that the oligonucleotide strands comprising unnatural or modified nucleotides can be easily prepared. Single-stranded oligonucleotides of the present disclosure can be prepared using solution-phase or solid-phase organic synthesis or both.

In some embodiments, a dsRNA agent of the present disclosure includes at least two nucleotide sequences, a sense strand sequence and an antisense strand sequence. The sense strand may comprise a nucleotide sequence selected from the group consisting of any one of the sense strand nucleotide sequences of any one of the duplexes in Table 2. The antisense strand may comprise a nucleotide sequence selected from the group consisting of any one of the antisense strand nucleotide sequences of any one of the duplexes in Table 2. In some embodiments, the dsRNA agent is not AD-66810.

In some embodiments, a dsRNA agent of the disclosure comprises, consists essentially of, or consists of a sense strand and an antisense strand, as set forth in Table 2.

III. Modified dsRNA Agents

In certain embodiments, the RNA of the dsRNA agent of the present disclosure is un-modified, and does not comprise, e.g., chemical modifications or conjugations known in the art and described herein. In other embodiments, the RNA of a dsRNA agent of the present disclosure is chemically modified to enhance stability or other beneficial characteristics. In some embodiments of the present disclosure, substantially all of the nucleotides of a dsRNA agent of the present disclosure are modified. In some embodiments of the present disclosure, all of the nucleotides of a dsRNA agent or substantially all of the nucleotides of a dsRNA agent are modified, i.e., not more than 5, 4, 3, 2, or 1 unmodified nucleotides are present in a strand of the dsRNA agent.

The nucleic acids featured in the present disclosure can be synthesized or modified by methods well established in the art, such as those described in "Current protocols in nucleic acid chemistry," Beaucage, S. L. et al. (Edrs.), John Wiley & Sons, Inc., New York, N.Y., USA, which methods are hereby incorporated herein by reference. Modifications include, for example, end modifications, e.g., 5'-end modifications (phosphorylation, conjugation, inverted linkages) or 3'-end modifications (conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2-position or 4'-position) or replacement of the sugar; or backbone modifications, including modification or replacement of the phosphodiester linkages. Specific examples of dsRNA agent compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments, a modified dsRNA agent will have a phosphorus atom in its internucleoside backbone.

Modified RNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5'-linked analogs of these, and those having inverted polarity wherein the adjacent pairs of nucleoside units are linked 3'-5' to 5'-3' or 2'-5' to 5'-2'. Various salts, mixed salts, and free acid forms are also included.

Representative U.S. patents that teach the preparation of the above phosphorus-containing linkages include, but are not limited to, U.S. Pat. Nos. 3,687,808; 4,469,863; 4,476, 301; 5,023,243; 5,177,195; 5,188,897; 5,264,423; 5,276, 019; 5,278,302; 5,286,717; 5,321,131; 5,399,676; 5,405, 939; 5,453,496; 5,455,233; 5,466,677; 5,476,925; 5,519, 126; 5,536,821; 5,541,316; 5,550,111; 5,563,253; 5,571, 799; 5,587,361; 5,625,050; 6,028,188; 6,124,445; 6,160, 109; 6,169,170; 6,172,209; 6,239,265; 6,277,603; 6,326, 199; 6,346,614; 6,444,423; 6,531,590; 6,534,639; 6,608, 035; 6,683,167; 6,858,715; 6,867,294; 6,878,805; 7,015, 315; 7,041,816; 7,273,933; 7,321,029; and U.S. Pat. RE39464, each of which are hereby incorporated herein by reference for teachings relevant to such methods of preparation.

Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S, and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and 5,677,439, each of which is hereby incorporated herein by reference for teachings relevant to such methods.

Suitable RNA mimetics are contemplated for use in dsRNA agents provided herein, in which both the sugar and the internucleoside linkage, i.e., the backbone, of the nucleotide units are replaced with novel groups. The base units are maintained for hybridization with an appropriate nucleic acid target compound. One such oligomeric compound in which an RNA mimetic that has been shown to have excellent hybridization properties is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative US patents that teach the preparation of PNA compounds include, but are not limited to, U.S. Pat. Nos. 5,539,082; 5,714,331; and 5,719,262, each of which is hereby incorporated herein by reference for teachings relevant to such methods. Additional PNA compounds suitable for use in the dsRNA agents of the present disclosure are described in, for example, in Nielsen et al., Science, 1991, 254, 1497-1500.

Some embodiments featured in the present disclosure include RNAs with phosphorothioate backbones and oligonucleosides with heteroatom backbones, and in particular —$CH_2$—NH—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$—[wherein the native phosphodiester backbone is represented as —O—P—O—$CH_2$—] of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506.

Modified RNAs can also contain one or more substituted sugar moieties. The dsRNA agents, featured herein can include one of the following at the 2'-position: OH; F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Exemplary suitable modifications include O[($CH_2$)$_n$O]$_m$$CH_3$, O($CH_2$)$_n$OCH$_3$, O($CH_2$)$_n$NH$_2$, O($CH_2$)$_n$CH$_3$, O($CH_2$)$_n$ONH$_2$, and O($CH_2$)$_n$ON[($CH_2$)$_n$CH$_3$)]$_2$, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of a dsRNA agent, or a group for improving the pharmacodynamic properties of a dsRNA agent, and other substituents having similar properties. In some embodiments, the modification includes a 2'-methoxyethoxy (2'-O—CH$_2$CH$_2$OCH$_3$, also known as 2'-O-(2-methoxyethyl) or 2'-MOE) (Martin et al., Helv. Chim. Acta, 1995, 78:486-504), i.e., an alkoxy-alkoxy group. Another exemplary modification is 2'-dimethylaminooxyethoxy, i.e., a O(CH$_2$)$_2$ON(CH$_3$)$_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH$_2$—O—CH$_2$—N(CH$_2$)$_2$. Further exemplary modifications include: 5'-Me-2'-F nucleotides, 5'-Me-2'-OMe nucleotides, 5'-Me-2'-deoxynucleotides, (both R and S isomers in these three families); 2'-alkoxyalkyl; and 2'-NMA (N-methylacetamide).

Other modifications include 2'-methoxy (2'-OCH$_3$), 2'-aminopropoxy (2'-OCH$_2$CH$_2$CH$_2$NH$_2$) and 2'-fluoro (2'-F). Similar modifications can also be made at other positions on the RNA of a dsRNA agent, particularly the 3' position of the sugar on the 3' terminal nucleotide or in 2'-5' linked dsRNAs and the 5' position of 5' terminal nucleotide. dsRNA agents can also have sugar mimetics such as cyclobutyl moieties in place of the pentofuranosyl sugar. Representative US patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920; certain of which are commonly owned with the instant application. The contents of each of the foregoing patent publications are hereby incorporated herein by reference for teachings related to such methods.

A dsRNA agent can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C), and uracil (U). Modified nucleobases include other synthetic and natural nucleobases such as deoxy-thymine (dT), 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine, and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the present disclosure. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. Nos. 3,687,808, 4,845,205; 5,130, 30; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, each of which is hereby incorporated herein by reference for teachings relevant to such methods.

In some embodiments, the RNA of a dsRNA agent can also be modified to include one or more bicyclic sugar moieties. A "bicyclic sugar" is a furanosyl ring modified by the bridging of two atoms. A "bicyclic nucleoside" ("BNA") is a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring. Thus, in some embodiments, an agent of the present disclosure may include one or more locked nucleic acids (LNA). A locked nucleic acid is a nucleotide having a modified ribose moiety in which the ribose moiety comprises an extra bridge connecting the 2' and 4' carbons. In other words, an LNA is a nucleotide comprising a bicyclic sugar moiety comprising a 4'-CH$_2$—O-2' bridge. This structure effectively "locks" the ribose in the 3'-endo structural conformation. The addition of locked nucleic acids to dsRNA agents has been shown to increase dsRNA agent stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12):3185-3193). Examples of bicyclic nucleosides for use in the polynucleotides of the present disclosure include without limitation nucleosides comprising a bridge between the 4' and the 2' ribosyl ring atoms. In certain embodiments, the antisense polynucleotide agents of the present disclosure include one or more bicyclic nucleosides comprising a 4' to 2' bridge. Examples of such 4' to 2' bridged bicyclic nucleosides, include but are not limited to, 4'-(CH$_2$)—O-2' (LNA); 4'-(CH$_2$)—S-2'; 4'-(CH$_2$)$_2$—O-2' (ENA); 4'-CH(CH$_3$)—O-2' (also referred to as "constrained ethyl" or "cEt") and 4'-CH(CH$_2$OCH$_3$)—O-2' (and analogs thereof; see, e.g., U.S. Pat. No. 7,399,845); 4'-C(CH$_3$)(CH$_3$)—O-2' (and analogs thereof; see, e.g., U.S. Pat. No. 8,278,283); 4'-CH$_2$—N(OCH$_3$)-2' (and analogs thereof; see, e.g., U.S. Pat. No. 8,278,425); 4'-CH$_2$—O—N(CH$_3$)-2' (see, e.g., U.S. Patent Publication No. 2004/0171570); 4'-CH$_2$—N(R)—O-2', wherein R is H, C$_1$-C$_{12}$ alkyl, or a protecting group (see, e.g., U.S. Pat. No. 7,427,672); 4'-CH$_2$—C(H)(CH$_3$)-2' (see, e.g., Chattopadhyaya et al., *J. Org. Chem.*, 2009, 74, 118-134); and 4'-CH$_2$—C(=CH$_2$)-2' (and analogs thereof; see, e.g., U.S. Pat. No. 8,278,426). The contents of each of the foregoing relevant to modified nucleic acids are hereby incorporated herein by reference.

Additional representative U.S. patents and U.S. patent Publications that teach the preparation of locked nucleic acid nucleotides include, but are not limited to, the following: U.S. Pat. Nos. 6,268,490; 6,525,191; 6,670,461; 6,770,748; 6,794,499; 6,998,484; 7,053,207; 7,034,133; 7,084,125; 7,399,845; 7,427,672; 7,569,686; 7,741,457; 8,022,193; 8,030,467; 8,278,425; 8,278,426; 8,278,283; US 2008/0039618; and US 2009/0012281, which are hereby incorporated herein by reference for teachings relevant to such methods.

Any of the foregoing bicyclic nucleosides can be prepared having one or more stereochemical sugar configurations including for example α-L-ribofuranose and β-D-ribofuranose (see WO99/14226).

The RNA of a dsRNA agent can also be modified to include one or more constrained ethyl nucleotides. As used herein, a "constrained ethyl nucleotide" or "cEt" is a locked nucleic acid comprising a bicyclic sugar moiety comprising a 4'-CH(CH$_3$)-0-2' bridge. In some embodiments, a constrained ethyl nucleotide is in the S conformation referred to herein as "S-cEt."

A dsRNA agent of the present disclosure may also include one or more "conformationally restricted nucleotides" ("CRN"). CRN are nucleotide analogs with a linker connecting the C2' and C4' carbons of ribose or the C3 and C5' carbons of ribose. CRN lock the ribose ring into a stable conformation and increase the hybridization affinity to mRNA. The linker is of sufficient length to place the oxygen in an optimal position for stability and affinity resulting in less ribose ring puckering.

Representative publications that teach the preparation of certain of the above noted CRN include, but are not limited to, U.S. Patent Publication No. 2013/0190383; and PCT publication WO2013/036868, which are hereby incorporated herein by reference for teachings relevant to such methods.

In some embodiments, a dsRNA agent of the present disclosure comprises one or more monomers that are UNA (unlocked nucleic acid) nucleotides. UNA is unlocked acyclic nucleic acid, wherein any of the bonds of the sugar has been removed, forming an unlocked "sugar" residue. In one example, UNA also encompasses monomer with bonds between C1'-C4' have been removed (i.e., the covalent carbon-oxygen-carbon bond between the C1' and C4' carbons). In another example, the C2'-C3' bond (i.e., the covalent carbon-carbon bond between the C2' and C3' carbons) of the sugar has been removed (see *Nuc. Acids Symp. Series*, 52, 133-134 (2008) and Fluiter et al., *Mol. Biosyst.*, 2009, 10, 1039, which are hereby incorporated by reference for teachings relevant to unlocked nucleic acid nucleotides).

Representative U.S. publications that teach the preparation of UNA include, but are not limited to, U.S. Pat. No. 8,314,227; and U.S. Patent Publication Nos. 2013/0096289; 2013/0011922; and 2011/0313020, which are hereby incorporated herein by reference for teachings relevant to such methods.

Potentially stabilizing modifications to the ends of RNA molecules can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-O-deoxythymidine (ether), N-(aminocaproyl)-4-hydroxyprolinol (Hyp-C6-amino), 2-docosanoyl-uridine-3'-phosphate, inverted base dT(idT) and others. Disclosure of this modification can be found in PCT Publication No. WO2011/005861.

In certain embodiments, the dsRNA agent is modified to include one or more adenosine-glycol nucleic acid ("GNA"). The term "GNA" refers to glycol nucleic acid which is a polymer similar to DNA or RNA but differing in the composition of its "backbone" in that is composed of repeating glycerol units linked by phosphodiester bonds:

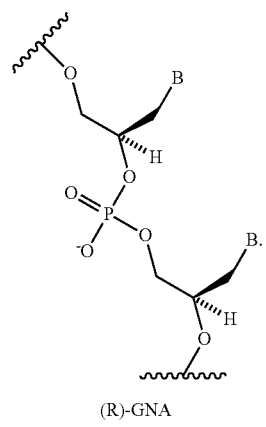

(R)-GNA

A description of adenosine-GNA can be found, for example, in Zhang, et al. (JACS 127(12):4174-75 (2005)).

Other modifications of the nucleotides of an dsRNA agent as disclosed herein include a 5' phosphate or 5' phosphate mimic, e.g., a 5'-terminal phosphate or phosphate mimic on the antisense strand of an dsRNA agent. Suitable phosphate mimics are disclosed in, for example U.S. Patent Publication No. 2012/0157511, which are hereby incorporated herein by reference for teachings relevant to such modifications.

Additional modified dsRNA agents targeting HBV are provided, for example, in WO2016/077321, which is incorporated herein by reference for teachings relevant to modifications.

In some embodiments, a dsRNA agent comprises, consists essentially of, or consists of a modified sense strand and a modified antisense strand, as set forth in Table 2.

IV. dsRNA Agents Conjugated to Ligands

The dsRNA agents of the present disclosure may be conjugated to a ligand. A ligand may alter the distribution, targeting or lifetime of a dsRNA agent into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand. Preferred ligands will not take part in duplex pairing in a duplexed nucleic acid.

Ligand-conjugated oligonucleotides of the present disclosure may be synthesized by the use of an oligonucleotide that bears a pendant reactive functionality, such as that derived from the attachment of a linking molecule onto the oligonucleotide (described below). This reactive oligonucleotide may be reacted directly with commercially available ligands, ligands that are synthesized bearing any of a variety of protecting groups, or ligands that have a linking moiety attached thereto.

In the ligand-conjugated oligonucleotides and ligand-molecule bearing sequence-specific linked nucleosides of the present disclosure, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. In some embodiments, the oligonucleotides or linked nucleosides of the present disclosure are synthesized by an automated synthesizer using phosphoramidites derived from ligand-nucleoside conjugates in addition to the standard phosphoramidites and non-standard phosphoramidites that are commercially available and routinely used in oligonucleotide synthesis.

Representative U.S. patents that teach the preparation of RNA conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941; 6,294,664; 6,320,017; 6,576,752; 6,783,931; 6,900,297; 7,037,646; 8,106,022, which are hereby incorporated herein by reference for teachings relevant to such methods of preparation.

A. Carbohydrate Conjugates

In preferred embodiments of the compositions and methods disclosed herein, a dsRNA agent oligonucleotide further comprises a carbohydrate. Carbohydrate-conjugated dsRNA agent are advantageous for the in vivo delivery of nucleic acids, as well as compositions suitable for in vivo therapeutic use, as described herein. As used herein, "carbohydrate" refers to a compound that is either a carbohydrate per se made up of one or more monosaccharide units having at least 6 carbon atoms (which can be linear, branched, or cyclic) with an oxygen, nitrogen or sulfur atom bonded to each carbon atom; or a compound having as a part thereof a carbohydrate moiety made up of one or more monosaccharide units each having at least six carbon atoms (which can be linear, branched or cyclic), with an oxygen, nitrogen or sulfur atom bonded to each carbon atom. Representative carbohydrates include the sugars (mono-, di-, tri-, and oligosaccharides containing from about 4, 5, 6, 7, 8, or 9 monosaccharide units), and polysaccharides such as starches, glycogen, cellulose, and polysaccharide gums. Specific monosaccharides include C5 and above (e.g., C5, C6, C7, or C8) sugars; di- and trisaccharides include sugars having two or three monosaccharide units (e.g., C5, C6, C7, or C8).

In some embodiments, a carbohydrate conjugate for use in the compositions and methods of the present disclosure is a monosaccharide. In some embodiments, a carbohydrate conjugate for use in the compositions and methods of the present disclosure is selected from the group consisting of:

Formula I

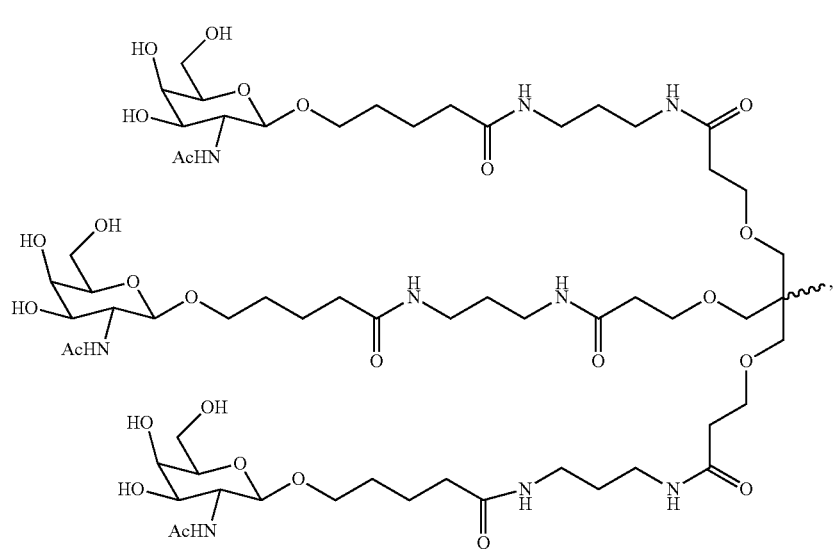

-continued
Formula II
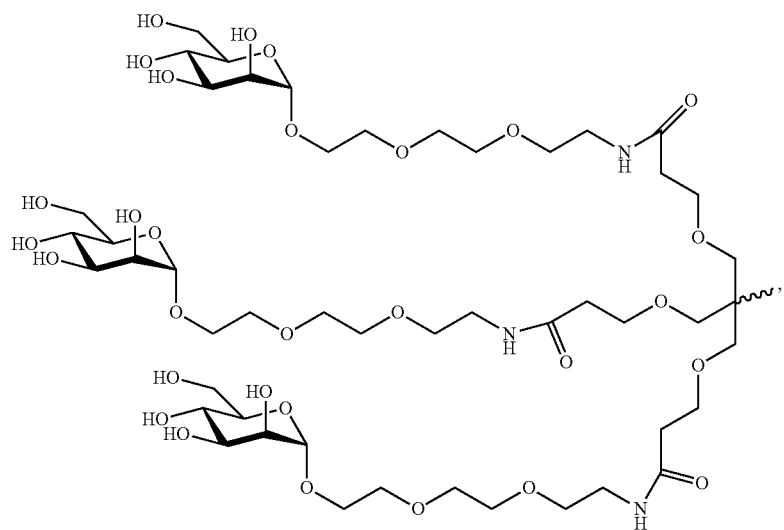
Formula III
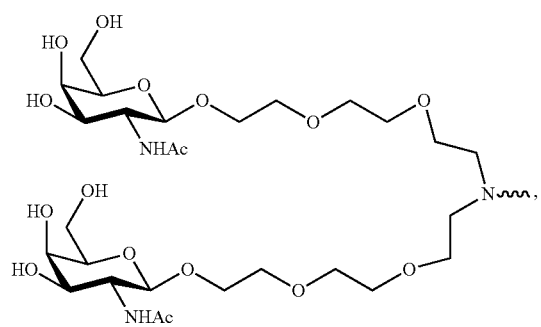
Formula IV
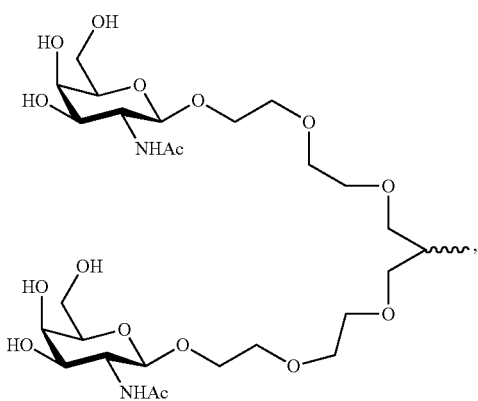
Formula V
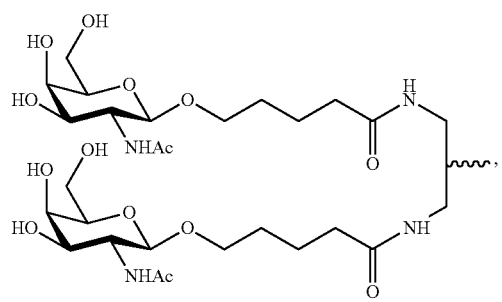
Formula VI
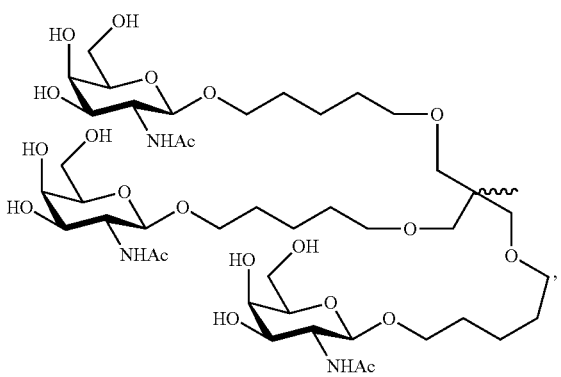
Formula VII
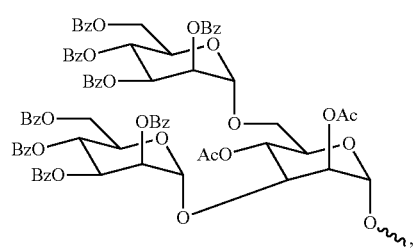

-continued
Formula VIII
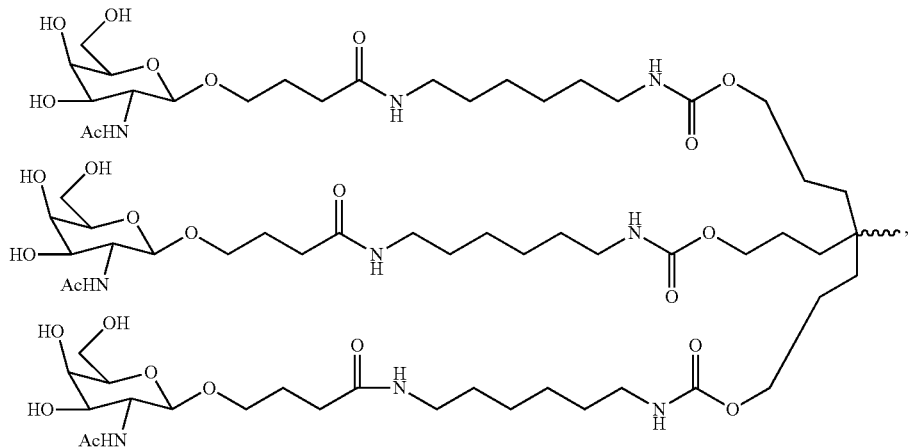
Formula IX
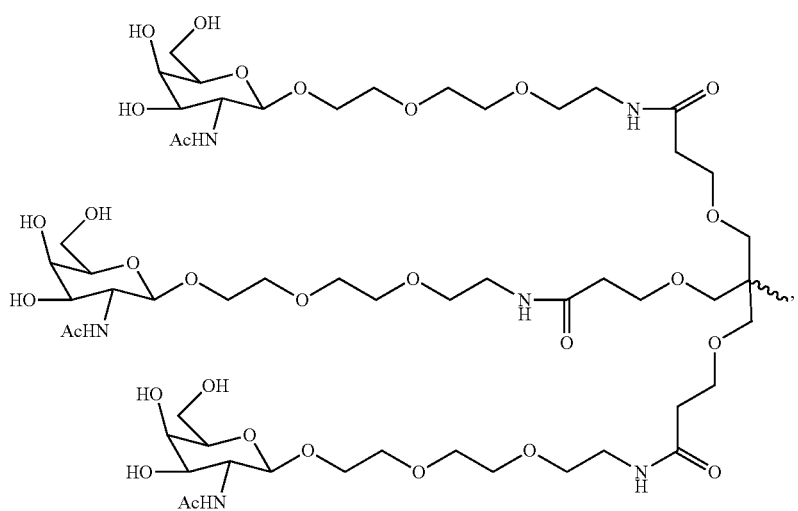
Formula X
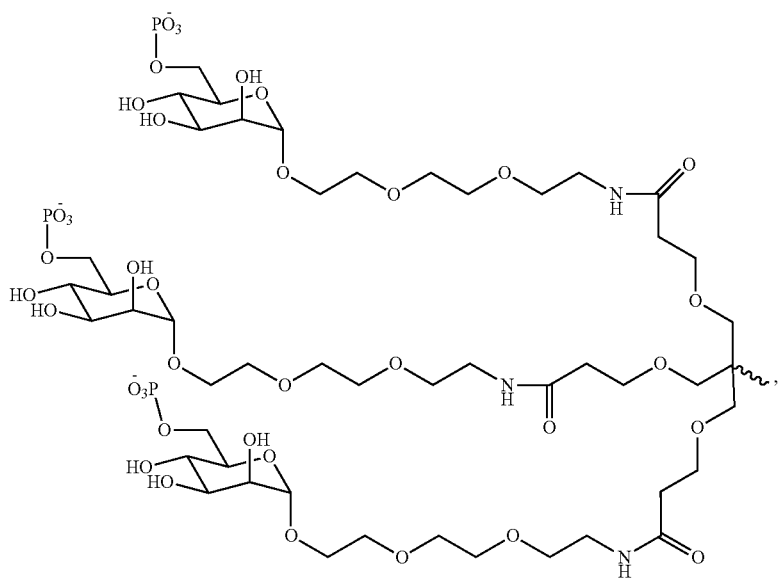

-continued
Formula XI
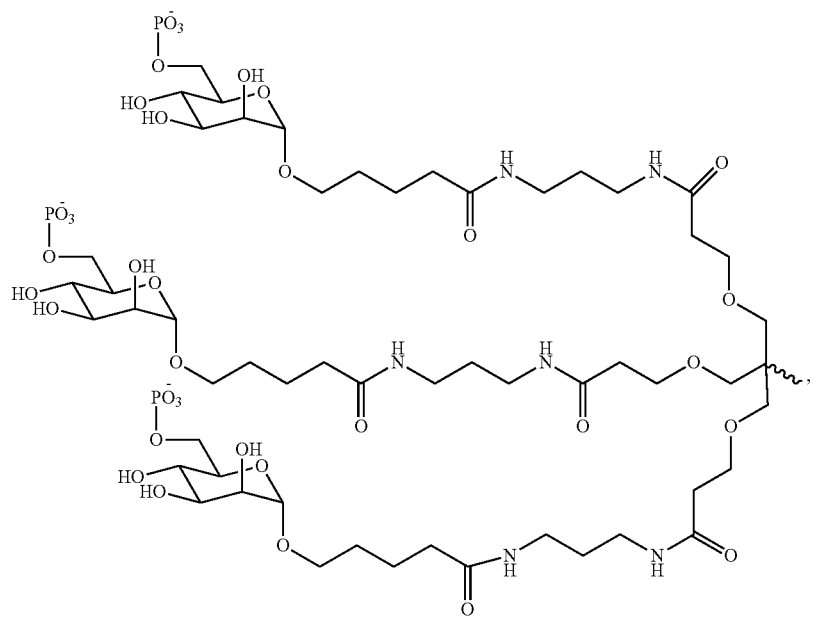
Formula XII
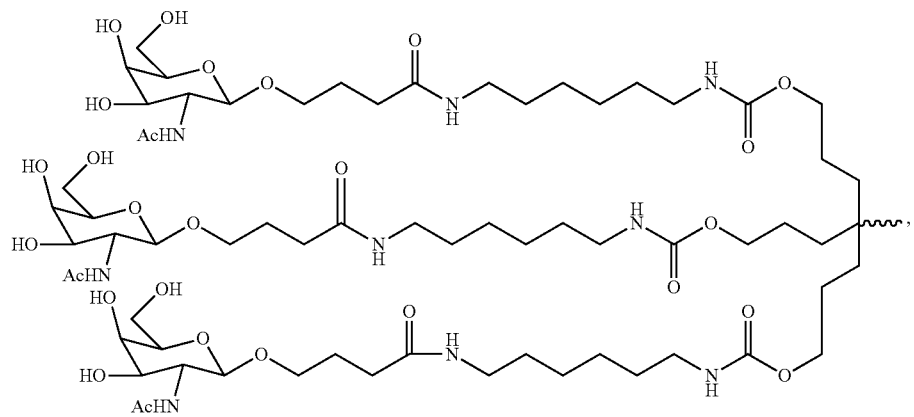
Formula XIII
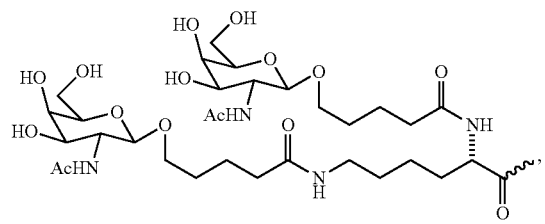
Formula XIV
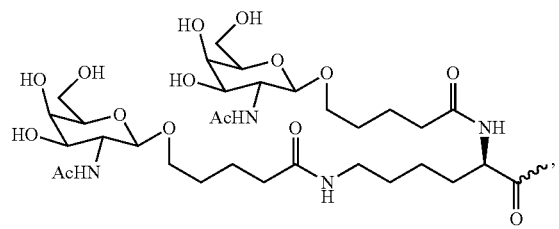
Formula XV
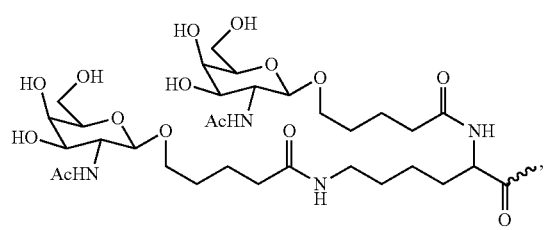
Formula XVI
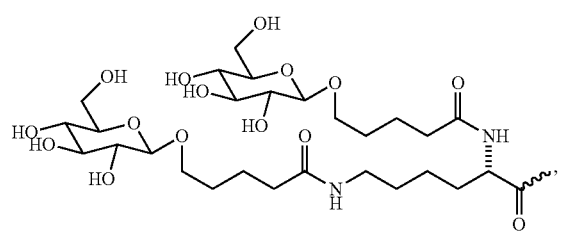

Formula XVII
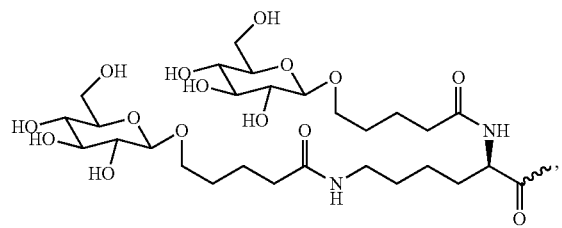
Formula XVIII
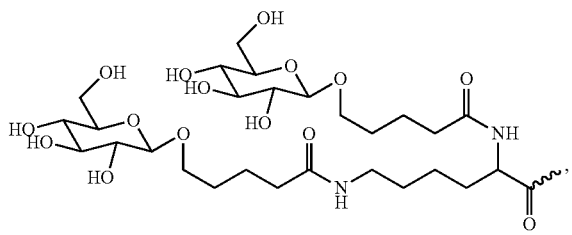
Formula XIX
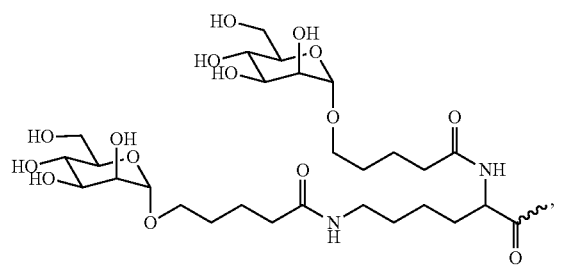
Formula XX
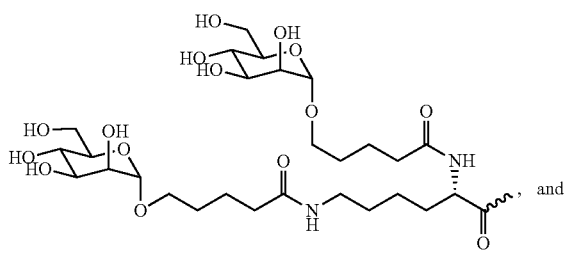, and
Formula XXI
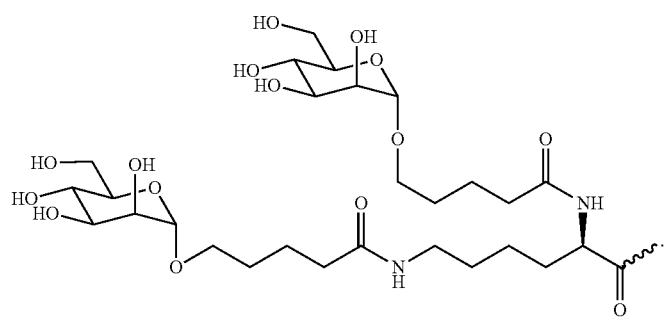
In some embodiments, the monosaccharide is an N-acetylgalactosamine (GalNAc). In some embodiments, the carbohydrate comprises multiple N-acetylgalactosamine units, such as
Formula I
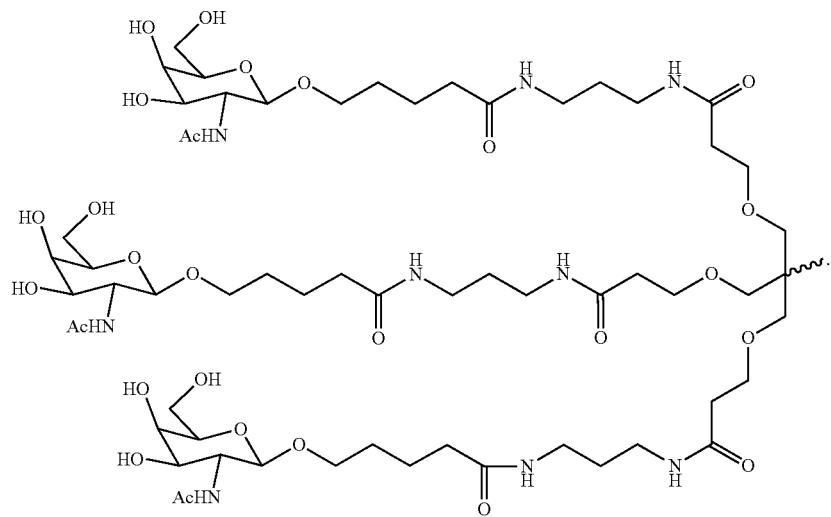

Another representative carbohydrate conjugate that may be used in the embodiments described herein includes, but is not limited to, Formula XXII

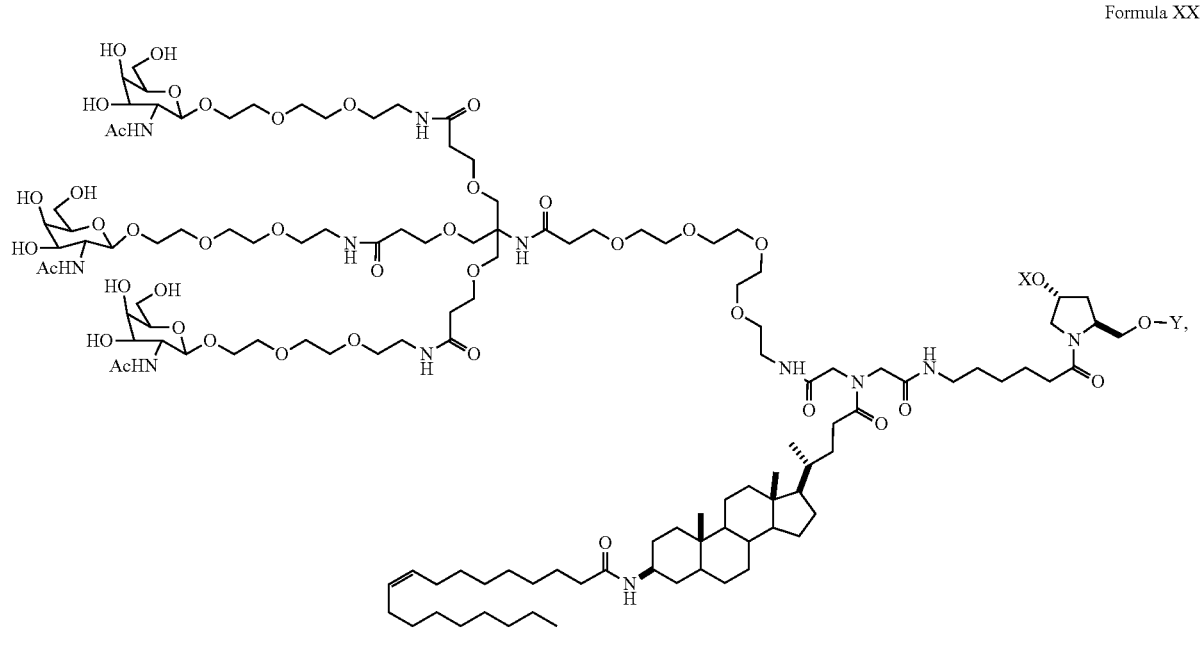

wherein when one of X or Y is an oligonucleotide, the other is a hydrogen.

In some embodiments of the present disclosure, the GalNAc or GalNAc derivative is attached to a dsRNA agent of the present disclosure via a monovalent linker. In some embodiments, the GalNAc or GalNAc derivative is attached to a dsRNA agent of the present disclosure via a bivalent linker. In some embodiments of the present disclosure, the GalNAc or GalNAc derivative is attached to a dsRNA agent of the present disclosure via a trivalent linker. In some embodiments, the carbohydrate ligand comprises three N-acetylgalactosamine units attached via a trivalent linker ("GalNAc$_3$").

In some embodiments, the double stranded dsRNA agent comprises one GalNAc or GalNAc derivative attached to the dsRNA agent. In some embodiments, the double stranded dsRNA agent comprises a plurality of (e.g., 2, 3, 4, 5, or 6) GalNAc or GalNAc derivatives, each independently attached to a plurality of nucleotides of the double stranded dsRNA agent through a plurality of monovalent linkers.

Additional carbohydrate conjugates suitable for use in the present disclosure include those described in PCT Publication Nos. WO2014/179620 and WO2014/179627, which are incorporated herein by reference for teachings relevant to such conjugates.

Non-limiting examples of dsRNA agent carbohydrate conjugates with linkers that may be used in the compositions and methods of disclosed herein include, but are not limited to, Formula XXIII

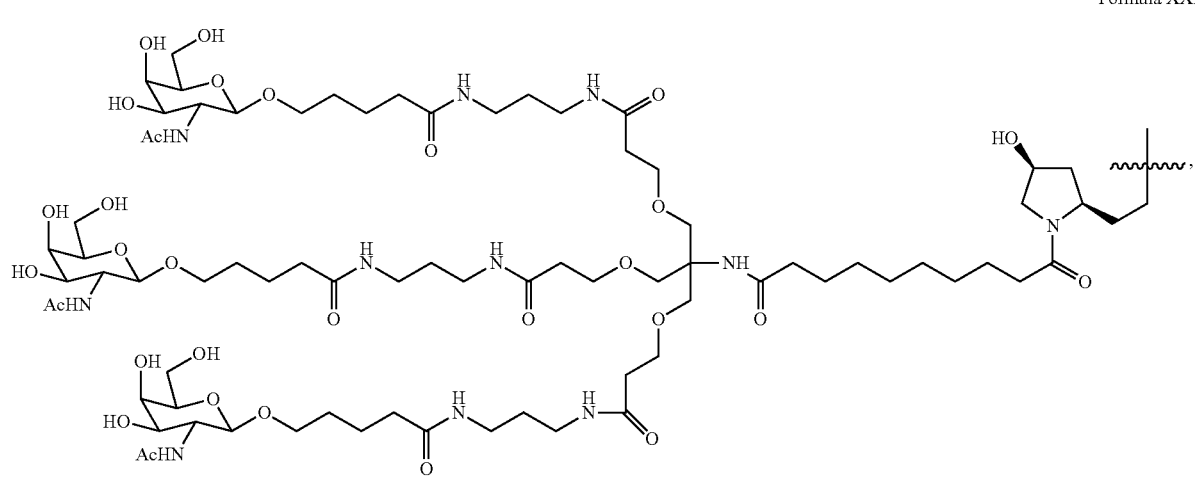

Formula XXIV
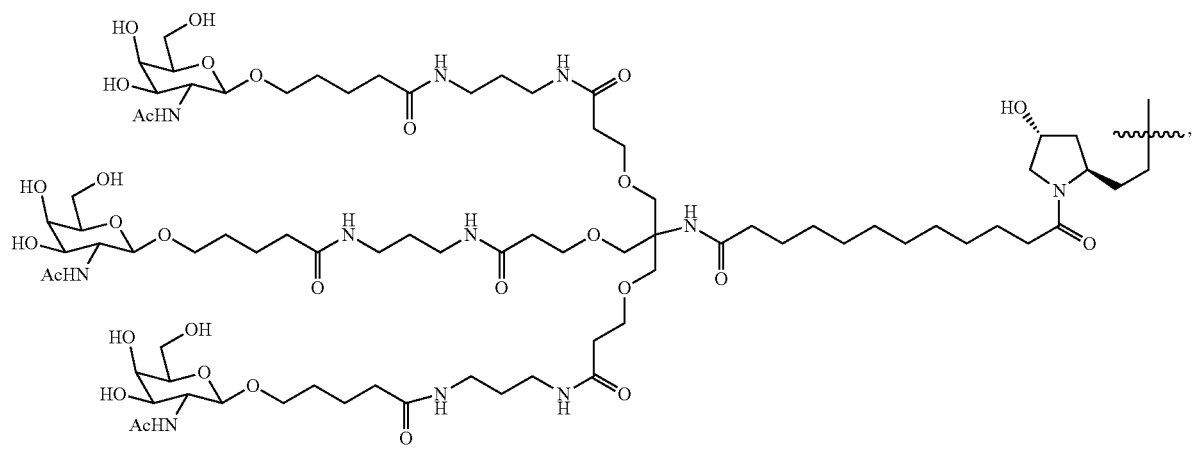
Formula XXV
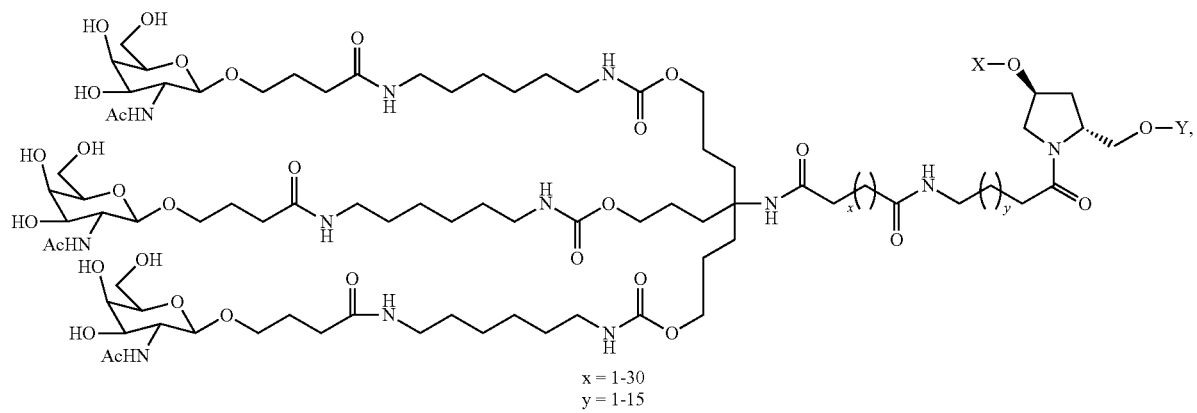
x = 1-30
y = 1-15
Formula XXVI
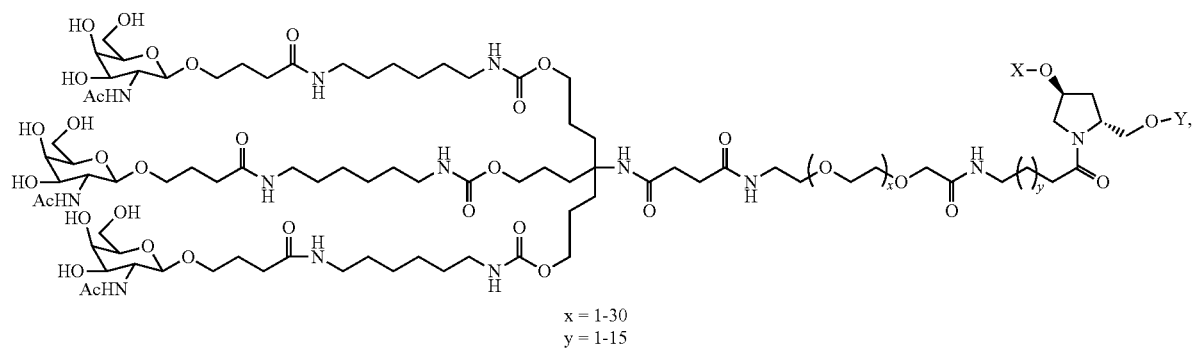
x = 1-30
y = 1-15
Formula XXVII
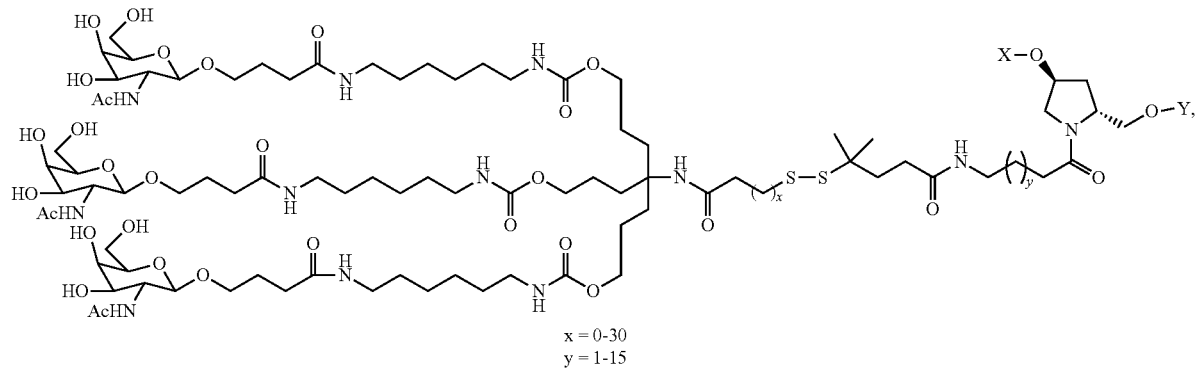
x = 0-30
y = 1-15

Formula XXVIII
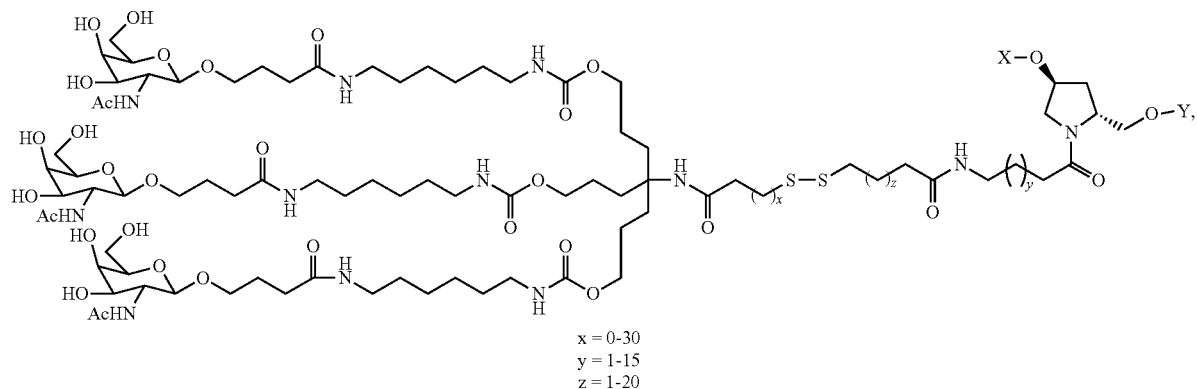
x = 0-30
y = 1-15
z = 1-20
Formula XXIX
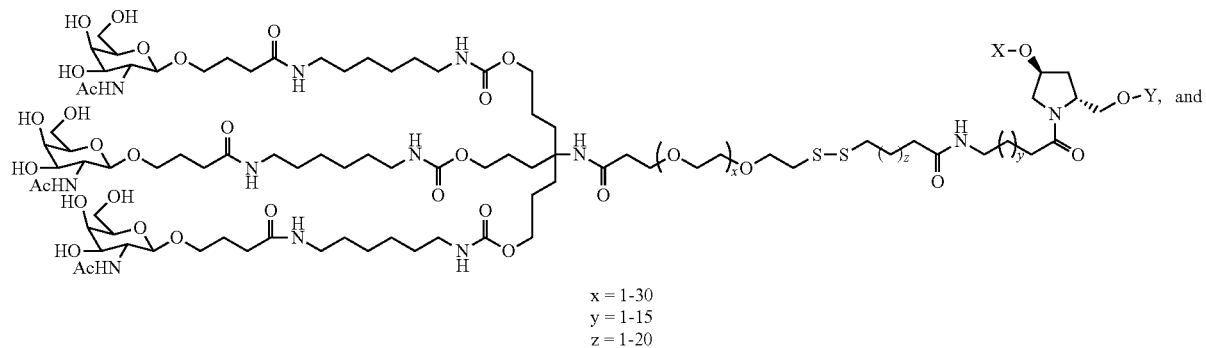
x = 1-30
y = 1-15
z = 1-20
Formula XXX
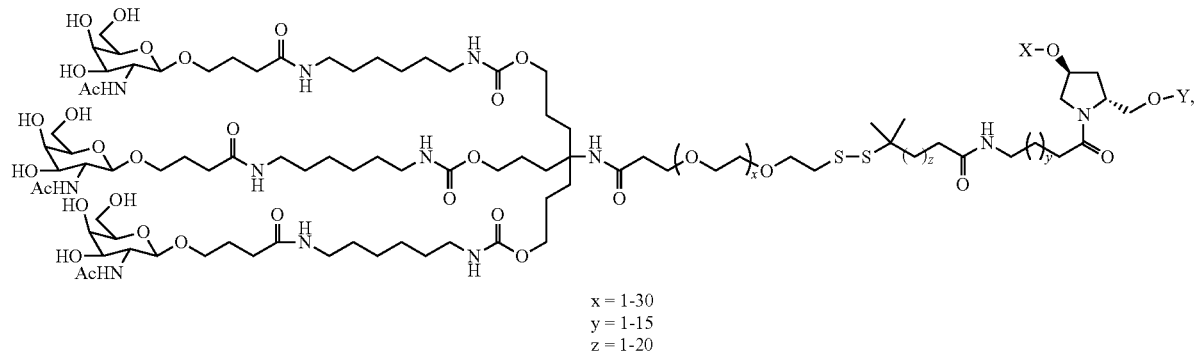
x = 1-30
y = 1-15
z = 1-20 wherein when one of X or Y is an oligonucleotide, the other is a hydrogen.

In some embodiments of the compositions and methods disclosed herein, a ligand is one or more "GalNAc" (N-acetylgalactosamine) derivatives attached through a bivalent or trivalent branched linker.

In some embodiments, a dsRNA agent as disclosed herein is conjugated to a bivalent or trivalent branched linker selected from the group of structures shown in any of formulae (XXXI)-(XXXIV):

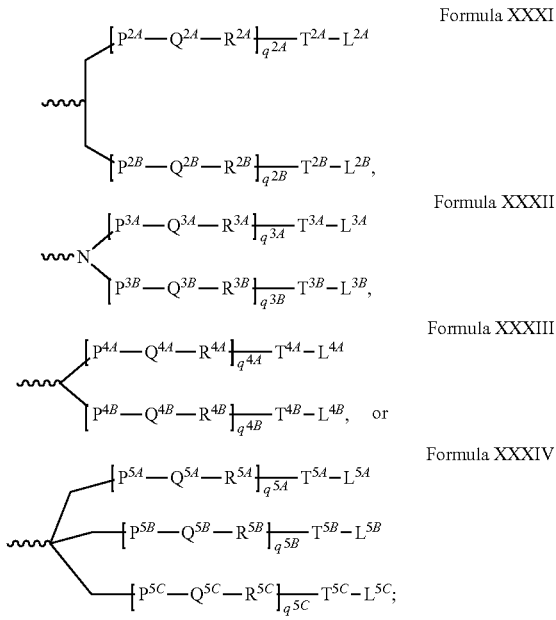

Formula XXXI

Formula XXXII

Formula XXXIII

Formula XXXIV wherein:
q2A, q2B, q3A, q3B, q4A, q4B, q5A, q5B and q5C represent independently for each occurrence 0-20 and wherein the repeating unit can be the same or different;
$P^{2A}$, $P^{2B}$, $P^{3A}$, $P^{3B}$, $P^{4A}$, $P^{4B}$, $P^{5A}$, $P^{5B}$, $P^{5C}$, $T^{2A}$, $T^{2B}$, $T^{3A}$, $T^{3B}$, $T^{4A}$, $T^{4B}$, $T^{4A}$, $T^{5B}$, $T^{5C}$ are each independently for each occurrence absent, CO, NH, O, S, OC(O), NHC(O), $CH_2$, $CH_2NH$ or $CH_2O$;
$Q^{2A}$, $Q^{2B}$, $Q^{3A}$, $Q^{3B}$, $Q^{4A}$, $Q^{4B}$, $Q^{5A}$, $Q^{5B}$, $Q^{5C}$ are independently for each occurrence absent, alkylene, substituted alkylene wherein one or more methylenes can be interrupted or terminated by one or more of O, S, S(O), $SO_2$, $N(R^N)$, C(R')=C(R''), C≡C or C(O);
$R^{2A}$, $R^{2B}$, $R^{3A}$, $R^{3B}$, $R^{4A}$, $R^{4B}$, $R^{5A}$, $R^{5B}$, $R^{5C}$ are each independently for each occurrence absent, NH, O, S, $CH_2$, C(O)O, C(O)NH, $NHCH(R^a)C(O)$, —C(O)—CH($R^a$)—NH—, CO, CH=N—O,

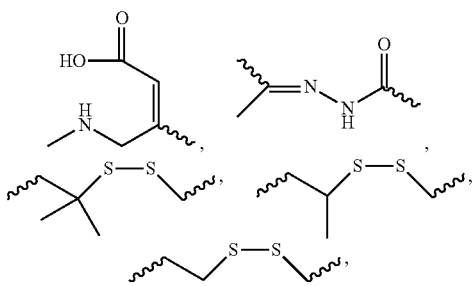

or heterocyclyl;
$L^{2A}$, $L^{2B}$, $L^{3A}$, $L^{3B}$, $L^{4A}$, $L^{4B}$, $L^{5A}$, $L^{5B}$ and $L^{5C}$ represent the ligand; i.e., each independently for each occurrence a monosaccharide (such as GalNAc), disaccharide, trisaccharide, tetrasaccharide, oligosaccharide, or polysaccharide; and $R^a$ is H or amino acid side chain. Trivalent conjugating GalNAc derivatives are particularly useful for use with dsRNA agents for inhibiting the expression of a target gene, such as those of formula (XXXIV):

wherein $L^{5A}$, $L^{5B}$ and $L^{5C}$ represent a monosaccharide, such as GalNAc derivative.

Examples of suitable bivalent and trivalent branched linker groups conjugating GalNAc derivatives include, but are not limited to, the structures recited above as formulas I, VI, X, IX, and XII.

B. Linkers

In some embodiments, the conjugate or ligand described herein can be attached to a dsRNA agent oligonucleotide with various linkers that can be cleavable or non-cleavable.

The term "linker" or "linking group" means an organic moiety that connects two parts of a compound, e.g., covalently attaches two parts of a compound. Linkers typically comprise a direct bond or an atom such as oxygen or sulfur, a unit such as NR8, C(O), C(O)NH, SO, $SO_2$, $SO_2NH$ or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhererroaryl, which one or more methylenes can be interrupted or terminated by O, S, S(O), $SO_2$, N(R8), C(O), substituted or unsubstituted aryl, substituted or unsubstituted heteroaryl, substituted or unsubstituted heterocyclic; where R8 is hydrogen, acyl, aliphatic or substituted aliphatic. In some embodiments, the linker is about 1-24, 2-24, 3-24, 4-24, 5-24, 6-24, 6-18, 7-18, 8-18, 7-17, 8-17, 6-16, 7-16, or 8-16 atoms.

A cleavable linking group is one which is sufficiently stable outside the cell, but which upon entry into a target cell is cleaved to release the two parts the linker is holding together. In some embodiments, the cleavable linking group is cleaved at least about 10 times, 20, times, 30 times, 40 times, 50 times, 60 times, 70 times, 80 times, 90 times, or more, or at least about 100 times faster in a target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential, or the presence of degradative molecules. Generally, cleavage agents are more prevalent or found at higher levels or activities inside cells than in serum or blood. Examples of such degradative agents include: redox agents, which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; and enzymes that can hydrolyze or degrade an acid cleavable linking group by acting as a general acid, peptidases (which can be substrate specific), and phosphatases.

A cleavable linking group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing a cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, a liver-targeting ligand can be linked to a cationic lipid through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus, one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It can be useful to make initial evaluations in cell-free or culture conditions and to confirm by further evaluations in whole animals. In preferred embodiments, useful candidate compounds are cleaved at least about 2, 4, 10, 20, 30, 40, 50, 60, 70, 80, 90, or 100 times faster in the cell (or under in vitro conditions selected to mimic intracellular conditions) as compared to blood or serum (or under in vitro conditions selected to mimic extracellular conditions).

i. Redox Cleavable Linking Groups

In some embodiments, a cleavable linking group is a redox cleavable linking group that is cleaved upon reduction or oxidation. An example of reductively cleavable linking group is a disulphide linking group (—S—S—). To determine if a candidate cleavable linking group is a suitable "reductively cleavable linking group," or for example is suitable for use with a particular dsRNA agent moiety and particular targeting agent one can look to methods described herein. For example, a candidate can be evaluated by incubation with dithiothreitol (DTT), or other reducing agent using reagents know in the art, which mimic the rate of cleavage that would be observed in a cell, e.g., a target cell. The candidates can also be evaluated under conditions which are selected to mimic blood or serum conditions. In some embodiments, candidate compounds are cleaved by at most about 10% in the blood. In some embodiments, useful candidate compounds are degraded at least about 2, 4, 10, 20, 30, 40, 50, 60, 70, 80, 90, or about 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

ii. Phosphate-Based Cleavable Linking Groups

In some embodiments, a cleavable linker comprises a phosphate-based cleavable linking group. A phosphate-based cleavable linking group is cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. In some embodiments, the phosphate-based linking group is —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O, —S—P(S)(H)—O—, —S—P(O)(H)—S—, or —O—P(S)(H)—S—. In some embodiments, the phosphate-based linking group is —O—P(O)(OH)—O—. These candidates can be evaluated using methods analogous to those described above.

iii. Acid Cleavable Linking Groups

In some embodiments, a cleavable linker comprises an acid cleavable linking group. An acid cleavable linking group is a linking group that is cleaved under acidic conditions. In some embodiments, acid cleavable linking groups are cleaved in an acidic environment with a pH of about 6.5 or lower (e.g., about 6.0, 5.75, 5.5, 5.25, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, C(O)O, or —OC(O). In some embodiments, the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

iv. Ester-Based Linking Groups

In some embodiments, a cleavable linker comprises an ester-based cleavable linking group. An ester-based cleavable linking group is cleaved by enzymes such as esterases and amidases in cells. Examples of ester-based cleavable linking groups include but are not limited to esters of alkylene, alkenylene, and alkynylene groups. Ester cleavable linking groups have the general formula —C(O)O—, or —OC(O)—. These candidates can be evaluated using methods analogous to those described above.

v. Peptide-Based Cleaving Groups

In some embodiments, a cleavable linker comprises a peptide-based cleavable linking group. A peptide-based cleavable linking group is cleaved by enzymes such as peptidases and proteases in cells. Peptide-based cleavable linking groups are peptide bonds formed between amino acids to yield oligopeptides (e.g., dipeptides, tripeptides, etc.) and polypeptides. Peptide-based cleavable groups do not include the amide group (—C(O)NH—). The amide group can be formed between any alkylene, alkenylene, or alkynelene. A peptide bond is a special type of amide bond formed between amino acids to yield peptides and proteins. The peptide-based cleavage group is generally limited to the peptide bond (i.e., the amide bond) formed between amino acids yielding peptides and proteins and does not include the entire amide functional group. Peptide-based cleavable linking groups have the general formula —NHCHRAC(O)NHCHRBC(O)—, where RA and RB are the R groups of the two adjacent amino acids. These candidates can be evaluated using methods analogous to those described above.

V. Delivery of a dsRNA Agent

The delivery of a dsRNA agent of the present disclosure to a cell, e.g., a cell within a subject, such as a human subject, can be achieved in a number of different ways. For example, delivery may be performed by contacting a cell with a dsRNA agent of the present disclosure either in vitro or in vivo. In vivo delivery may also be performed directly by administering a composition comprising a dsRNA agent, to a subject. Alternatively, in vivo delivery may be performed indirectly by administering one or more vectors that encode and direct the expression of the dsRNA agent. These alternatives are discussed further below.

In general, any method of delivering a nucleic acid molecule (in vitro or in vivo) can be adapted for use with a dsRNA agent of the present disclosure (see, e.g., Akhtar S. and Julian R L. (1992) Trends Cell. Biol. 2(5):139-144 and WO94/02595, which are incorporated herein by reference for teachings relevant to such methods of delivery). For in vivo delivery, factors to consider in order to deliver a dsRNA agent molecule include, for example, biological stability of the delivered molecule, prevention of nonspecific effects, and accumulation of the delivered molecule in the target tissue.

For administering a dsRNA agent systemically for the treatment of a disease, the RNA can be modified or alternatively delivered using a drug delivery system; both methods act to prevent the rapid degradation of the dsRNA by endo- and exo-nucleases in vivo. Modification of the RNA or the pharmaceutical carrier or pharmaceutical excipient can also permit targeting of the dsRNA agent composition to the target tissue and avoid undesirable off-target effects. dsRNA agent molecules can be modified by chemical conjugation, e.g., a carbohydrate conjugate as described above.

VI. Pharmaceutical Compositions

The present disclosure also includes pharmaceutical compositions and formulations that include the dsRNA agents of the present disclosure. In some embodiments, provided herein are pharmaceutical compositions containing a dsRNA agent, as described herein, and a pharmaceutically acceptable carrier. The pharmaceutical compositions containing the dsRNA agent are useful for treating a disease or disorder associated with the expression or activity of an HBV gene. Such pharmaceutical compositions are formulated based on the mode of delivery. One example is compositions that are formulated for systemic administration via parenteral delivery, e.g., by subcutaneous (SC), intramuscular (IM), or intravenous (IV) delivery. In certain embodiments, the present disclosure provides compositions that are formulated for organ-specific (e.g., hepatic) intra-arterial, intratumoral, intradermal, intravitreal injection, ocular topical, ophthalmic (eye drops), nebulization, ocular topical or other topical routes, suppository, or oral administration. In preferred embodiments, compositions are administered subcutaneously.

The pharmaceutical compositions of the present disclosure may be administered in dosages sufficient to inhibit expression of an HBV gene. In some embodiments, a dsRNA agent will be administered at a dose of about 0.5 mg/kg to 50 mg/kg, or 0.3 mg/kg to 20 mg/kg, or 3 mg/kg to 10 mg/kg per dose, or preferably 3 mg/kg to 10 mg/kg per dose. For example, the dsRNA can be administered at about 0.5 mg/kg, 1 mg/kg, 1.5 mg/kg, 2 mg/kg, 3 mg/kg, 10 mg/kg, 20 mg/kg, 30 mg/kg, 40 mg/kg, or 50 mg/kg per single dose. In some embodiments, a dsRNA agent is administered at a dose of 50 mg to 900 mg.

Compositions can also be prepared and packaged for a fixed dose to a subject independent of weight. Exemplary dosage levels can be calculated by multiplying the per kilogram body weight by the body weight for the average subject. For example, the average adult human is typically considered to be about 70 kg.

A repeat-dose regimen may include administration of a therapeutic amount of dsRNA agent on a regular basis, such as once a month, once every other month, or once every third month. In preferred embodiments, the dsRNA agent is administered no more frequently than once per month. After an initial treatment regimen, the treatments can be administered on a less frequent basis.

The pharmaceutical composition can be administered for an indefinite period of time, e.g., in a subject with one or more signs or symptoms of HBV infection, e.g., detectable HBV antigen or HBV DNA including HBV cccDNA. In some embodiments, treatment with the dsRNA agent is performed for a discrete or defined period of time and provides a functional cure.

The skilled artisan will appreciate that certain factors can influence the dosage and timing required to effectively treat a subject, including but not limited to the severity of the disease or disorder, previous treatments, the general health or age of the subject, and other diseases present. Moreover, treatment of a subject with a therapeutically effective amount of a composition can include a single treatment or a series of treatments. Estimates of effective dosages and in vivo half-lives for the individual dsRNA agents encompassed by the present disclosure can be made using conventional methodologies or on the basis of in vivo testing using an appropriate animal model, as described elsewhere herein.

A. Excipients

A "pharmaceutical carrier" or "pharmaceutical excipient" is a pharmaceutically acceptable solvent, suspending agent, or any other pharmacologically inert vehicle for delivering one or more nucleic acids to an animal. Such agents are well known in the art.

B. Other Components

The compositions of the present disclosure can additionally contain other adjunct components conventionally found in pharmaceutical compositions, at their art-established usage levels. Thus, for example, the compositions can contain additional, compatible, pharmaceutically-active materials such as, for example, antipruritics, astringents, local anesthetics, or anti-inflammatory agents, or can contain additional materials useful in physically formulating various dosage forms of the compositions of the present disclosure, such as preservatives, antioxidants, and stabilizers. However, such materials, when added, should not unduly interfere with the biological activities of the components of the compositions of the present disclosure. The formulations can be sterilized and, if desired, mixed with auxiliary agents, e.g., preservatives, stabilizers, wetting agents, emulsifiers, salts for influencing osmotic pressure, or buffers, and the like, which do not deleteriously interact with the nucleic acid(s) of the formulation.

In some embodiments, pharmaceutical compositions featured in the present disclosure include (a) one or more dsRNA agent compounds and (b) one or more agents that function by a non-RNAi mechanism and that are useful in treating a disorder HBV associated disorder. Examples of such agents include, but are not limited to, an anti-inflammatory agent, anti-steatosis agent, anti-viral, and anti-fibrosis agent.

In addition, other substances commonly used to protect the liver, such as silymarin, can also be used in conjunction with the dsRNA agents described herein. Other agents useful for treating liver diseases include telbivudine, entecavir, and protease inhibitors such as telaprevir and other disclosed, for example, in US2005/0148548, US2004/0167116, US2003/0144217, and US2004/0127488.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. In some embodiments, compounds that exhibit high therapeutic indices are preferred.

The data obtained from cell culture assays and animal studies can be used in formulating a range of dosage for use in humans. The dosage of compositions featured herein in the present disclosure lies generally within a range of circulating concentrations that include the ED50 with little or no toxicity. The dosage can vary within this range depending upon the dosage form employed and the route of administration utilized. For any compound used in the methods featured in the present disclosure, the therapeutically effective dose can be estimated initially from cell culture assays. A dose can be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

In addition to their administration, as discussed above, the dsRNA agents featured herein can be administered in combination with other known agents effective in treatment of HBV infection. In any event, the administering physician can adjust the amount and timing of dsRNA agent administration on the basis of results observed using standard measures of efficacy known in the art or described herein.

VII. Methods

The present disclosure also provides methods of inhibiting expression of HBV in a cell. The methods include contacting a cell with a dsRNA agent, e.g., a double stranded dsRNA agent, in an amount effective to inhibit expression of HBV in the cell, thereby inhibiting expression of HBV in the cell.

Contacting of a cell with a dsRNA agent, e.g., a double stranded dsRNA agent, may be done in vitro or in vivo. Contacting a cell in vivo with the dsRNA agent includes contacting a cell or group of cells within a subject, e.g., a human subject, with the dsRNA agent. Combinations of in vitro and in vivo methods of contacting a cell are also possible. Contacting a cell may be direct or indirect, as discussed above. Furthermore, contacting a cell may be accomplished via a targeting ligand, including any ligand described herein or known in the art. In preferred embodiments, the targeting ligand is a carbohydrate moiety, e.g., a GalNAc$_3$ ligand, or any other ligand that directs the dsRNA agent to a site of interest.

In some embodiments of the methods of the present disclosure, the dsRNA agent is administered to a subject such that the dsRNA agent is delivered to a specific site within the subject. The inhibition of expression of an HBV gene may be assessed using measurements of the level or change in the level of HBV mRNA or HBV protein in a sample derived from fluid or tissue from the specific site within the subject. In preferred embodiments, the site is selected from liver and blood. The site may also be a subsection or subgroup of cells or fluid prepared from any one of the aforementioned sites.

In some embodiments, the methods disclosed herein are useful for treating a subject having an HBV infection, e.g., a subject that would benefit from reduction in HBV gene expression or HBV replication. In one aspect, the present disclosure provides methods of reducing the level of Hepatitis B virus cccDNA in a subject infected with HBV. In another aspect, the present disclosure provides methods of reducing the level of HBV antigen, e.g., HBsAg or HBeAg, in a subject infected with HBV. In another aspect, the present disclosure provides methods of reducing the viral load of HBV in a subject infected with HBV. The present disclosure also provides methods of reducing the level of alanine aminotransferase (ALT) or aspartate aminotransferase (AST) in a subject infected with HBV (although a transient elevation of ALT or AST can be associated with viral clearance). In one aspect, the present disclosure provides methods for increasing the level of anti-HBV antibodies in a subject infected with HBV. In another aspect, the present disclosure provides methods of treating a subject having an HBV infection. In one aspect, the present disclosure provides methods of treating a subject having an HBV-associated disease, e.g., hepatitis D virus infection, delta hepatitis, acute hepatitis B; acute fulminant hepatitis B; chronic hepatitis B; liver fibrosis; end-stage liver disease; or hepatocellular carcinoma. Furthermore, as HDV infection depends on obligatory helper functions provided by HBV for transmission, and subjects having an HBV infection may also have an HDV infection, in some embodiments the methods for treatment described herein are also useful for treating a subject having an HDV infection or an HDV-associated disorder, such as hepatitis B virus infection, chronic hepatitis B infection (CHB), chronic Hepatitis B infection (CHB), cirrhosis, liver failure, and hepatocellular carcinoma (HCC). In some embodiments, the treatment methods (and uses) of the present disclosure include administering to the subject, e.g., a human, a therapeutically effective amount of a dsRNA agent of the present disclosure targeting an HBV gene or a pharmaceutical composition comprising a dsRNA agent of the present disclosure targeting an HBV gene.

In one aspect, the present disclosure provides methods of preventing at least one symptom in a subject having an HBV infection, e.g., presence of serum or liver HBV cccDNA; the presence of serum HBV DNA; the presence of serum or liver HBV antigen, e.g., HBsAg or HBeAg; elevated ALT; elevated AST; the absence or low level of anti-HBV antibodies; a liver injury; cirrhosis; delta hepatitis, acute hepatitis B; acute fulminant hepatitis B; chronic hepatitis B; liver fibrosis; end-stage liver disease; hepatocellular carcinoma; serum sickness-like syndrome; anorexia; nausea; vomiting; low-grade fever; myalgia; fatigability; disordered gustatory acuity and smell sensations (aversion to food and cigarettes); right upper quadrant and epigastric pain (intermittent, mild to moderate); hepatic encephalopathy; somnolence; disturbances in sleep pattern; mental confusion; coma; ascites; gastrointestinal bleeding; coagulopathy; jaundice; hepatomegaly (mildly enlarged, soft liver); splenomegaly; palmar erythema; spider nevi; muscle wasting; spider angiomas; vasculitis; variceal bleeding; peripheral edema; gynecomastia; testicular atrophy; abdominal collateral veins (caput medusa); ALT levels higher than AST levels; elevated gamma-glutamyl transpeptidase (GGT) and alkaline phosphatase (ALP) levels, not more than 3 times the ULN); slightly low albumin levels; elevated serum iron levels; leukopenia (i.e., granulocytopenia); lymphocytosis; increased erythrocyte sedimentation rate (ESR); shortened red blood cell survival; hemolysis; thrombocytopenia; a prolongation of the international normalized ratio (INR); presence of serum or liver HBsAg, HBeAg, Hepatitis B core antibody (anti-HBc) immunoglobulin M (IgM); hepatitis B surface antibody (anti-HBs), or hepatitis B e antibody (anti-HBe), or HBV DNA; increased bilirubin levels; hyperglobulinemia; the presence of tissue-nonspecific antibodies, such as anti-smooth muscle antibodies (ASMAs) or antinuclear antibodies (ANAs) (10-20%); the presence of tissue-specific antibodies, such as antibodies against the thyroid gland (10-20%); elevated levels of rheumatoid factor (RF); low platelet and white blood cell counts; lobular, with degenerative and regenerative hepatocellular changes, and accompanying inflammation; or predominantly centrilobular necrosis, whether detectable or undetectable. The methods include administering to the subject a therapeutically effective amount of the dsRNA agent, e.g., dsRNA, or pharmaceutical compositions comprising the dsRNA agent, thereby preventing at least one symptom in the subject having a disorder that would benefit from reduction in HBV gene expression, such as a subject having an HBV infection or a subject having both an HBV and an HDV infection.

In another aspect, the present disclosure provides uses of a therapeutically effective amount of a dsRNA agent of the present disclosure for treating a subject, e.g., a subject that would benefit from a reduction or inhibition of HBV gene expression, such as a subject having an HBV infection or a subject having both an HBV and an HDV infection.

In a further aspect, the present disclosure provides uses of a dsRNA agent, e.g., a dsRNA, of the present disclosure targeting an HBV gene or pharmaceutical composition comprising a dsRNA agent targeting an HBV gene in the manufacture of a medicament for treating a subject, e.g., a subject that would benefit from a reduction of HBV gene expression or HBV replication, such as a subject having an HBV infection or a subject having both an HBV and an HDV infection, and a subject having a disorder that would benefit from reduction in HBV gene expression, e.g., a HBV-associated disease.

In another aspect, the present disclosure provides uses of a dsRNA agent as described herein, for preventing at least one symptom in a subject suffering from a disorder that would benefit from a reduction or inhibition of HBV gene expression or HBV replication.

In a further aspect, the present disclosure provides uses of a dsRNA agent as described herein in the manufacture of a medicament for preventing at least one symptom in a subject suffering from a disorder that would benefit from a reduction or inhibition of HBV gene expression or HBV replication, such as a HBV-associated disease.

In some embodiments, an dsRNA agent targeting HBV is administered to a subject having an HBV infection or both and HBV and an HDV infection, or an HBV-associated disease such that the expression of one or more HBV genes, HBV ccc DNA levels, HBV antigen levels, HBV viral load levels, ALT, or AST, e.g., in a cell, tissue, blood or other tissue or fluid of the subject are reduced by, or normalized by, at least 80%, 85%, 90%, 95%, 98% or more towards normal when the dsRNA agent is administered to the subject.

The methods and uses of the present disclosure include, in some embodiments, administering a composition described herein such that expression of the target HBV gene is decreased, such as for about 1 month. In some embodiments, expression of the target HBV gene is decreased for an extended duration, e.g., at least two months, three months, or longer. In some embodiments, the methods and uses of the present disclosure include administering a composition described herein result in a functional cure.

Administration of the dsRNA according to the methods and uses described herein may result in a reduction of the severity, signs, symptoms, or markers of such diseases or disorders in a patient with an HBV infection or both and HBV and an HDV infection, or HBV-associated disease. By "reduction" in this context is meant a clinically significant decrease in such level. The reduction can be, for example, at least 80%, 85%, 90%, 95%, or 98%, or to below the level of detection.

In some embodiments, the efficacy of the methods of the present disclosure can be monitored by detecting or monitoring a reduction in a symptom of an HBV-associated disease. These symptoms may be assessed in vitro or in vivo using any method known in the art.

Efficacy of treatment of disease can be assessed, for example by measuring disease progression, disease remission, symptom severity, reduction in pain, quality of life, dose of a medication required to sustain a treatment effect, level of a disease marker, or any other measurable parameter appropriate for a given disease being treated. It is well within the ability of one skilled in the art to monitor efficacy of treatment by measuring any one of such parameters, or any combination of parameters. For example, efficacy of treatment of CHB may be assessed, for example, by periodic monitoring of viral load and transaminase levels. Comparison of the later readings with the initial readings provides a physician an indication of whether the treatment is effective. It is well within the ability of one skilled in the art to monitor efficacy of treatment by measuring any one of such parameters, or any combination of parameters. In connection with the administration of a dsRNA agent targeting HBV or pharmaceutical composition thereof, "effective against" an HBV-associated disease indicates that administration in a clinically appropriate manner results in a beneficial effect for at least a statistically significant fraction of patients, such as improvement of symptoms, a cure, a reduction in disease, extension of life, improvement in quality of life, or other effect generally recognized as positive by medical doctors familiar with treating HBV infection or an HBV-associated disease and the related causes.

A treatment effect is evident when there is a clinically significant improvement in one or more parameters of disease status, or by a failure to worsen or to develop symptoms where they would otherwise be anticipated. As an example, a favorable change of at least 50% in a measurable parameter of disease, and preferably at least 70% or more can be indicative of effective treatment. Efficacy for a given dsRNA agent drug or formulation of that drug can also be judged using an experimental animal model for the given disease as known in the art. When using an experimental animal model, efficacy of treatment is evidenced when a statistically significant reduction in a sign or symptom is observed.

Administration of the dsRNA agent can reduce the presence of serum or liver HBV cccDNA, the presence of serum or liver HBV antigen, e.g., HBsAg or HBeAg; or normalize ALT levels, or AST levels, e.g., in a cell, tissue, blood, urine, or other compartment of the patient by at least 70%, 75%, 80%, 85%, 90%, or 95%, or to below the level of detection of the assay, towards or to the upper level of normal for a laboratory value.

Administration of the dsRNA agent can make detectable or increase the presence of serum or liver anti-HBV antibodies, e.g., anti-HBsAg antibodies, e.g., in a cell, tissue, blood, or other compartment of the patient by at least 80%, 85%, 90%, 95%, or more; or to make antibodies detectable when none were detectable prior to treatment.

Owing to the inhibitory effects on HBV expression, in some embodiments, a composition according to the present disclosure or a pharmaceutical composition prepared therefrom can enhance the quality of life.

Subjects that would benefit from a reduction or inhibition of HBV gene expression are those having an HBV infection or an HBV-associated disease or disorder as described herein.

Treatment of a subject that would benefit from a reduction or inhibition of HBV gene expression includes therapeutic and prophylactic treatment.

The present disclosure further provides methods and uses of a dsRNA agent or a pharmaceutical composition thereof for treating a subject that would benefit from reduction or inhibition of HBV gene expression, e.g., a subject having a HBV-associated disease, in combination with other pharmaceuticals or other therapeutic methods, e.g., with known pharmaceuticals or known therapeutic methods, such as, for example, those which are currently employed for treating these disorders.

For example, in some embodiments, a dsRNA agent targeting one or more HBV genes is administered in combination with, e.g., an agent useful in treating an HBV-associated disease as described herein. For example, additional therapeutics and therapeutic methods suitable for treating a subject that would benefit from reduction in HBV expression, e.g., a subject having a HBV-associated disease, include a dsRNA agent targeting a different portion of the HBV genome, an antiviral agent, a nucleotide analog, a nucleoside analog, a reverse transcriptase inhibitor (e.g., Tenofovir disoproxil fumarate (TDF), Tenofovir alafenamide, Lamivudine, Adefovir dipivoxil, Entecavir (ETV), Telbivudine, AGX-1009, emtricitabine, clevudine, ritonavir, dipivoxil, lobucavir, famvir, FTC, N-Acetyl-Cysteine (NAC), PC1323, theradigm-HBV, thymosin-alpha, and ganciclovir), an immune stimulator (e.g., pegylated interferon alfa 2a (PEG-IFN-u2a), Interferon alfa-2b, a recombinant human interleukin-7, and a Toll-like receptor 7 (TLR7) agonist), a therapeutic vaccine (e.g., GS-4774, DV-601, and TG1050), a viral entry inhibitor (e.g., Myrcludex), an oligonucleotide that inhibits the secretion or release of HbsAg (e.g., REP 9AC), a capsid inhibitor (e.g., Bay41-4109 and NVR-1221), a cccDNA inhibitor (e.g., IHVR-25), or other therapeutic agents or procedures, e.g., liver transplant or chemotherapy, for treating a HBV-associated disease, or a combination of any of the foregoing.

A subject administered a dsRNA agent of the present disclosure may further be administered with one or more other therapeutics that function by a non-RNAi mechanism and that are useful in treating an HBV infection. Exemplary therapeutics that may be used in a combination therapy of the present disclosure include immune modulators, which stimulate the immune system by, for example, enhancing T-cell helper activity, maturation of B lymphocytes, inhibiting T-cell suppressors, and enhancing HLA type I expression. Suitable immune modulators include interferons, which have a variety of properties that include antiviral, immunomodulatory, and antiproliferative effects.

For example, the current treatment for chronic hepatitis B is interferon therapy, which is administered to subjects who have a documented HBV infection for at least six months, elevated liver enzymes (AST and ALT), and an actively dividing virus in their blood (HBeAg, or HBV DNA positive tests). Interferon-α therapy produces a long-term, sustained remission of the disease in about 35% of those with chronic hepatitis B, with normalization of liver enzymes and loss of the three markers for an active infection (HBeAg, HBV DNA, and HBsAg). Subjects with an acute HBV infection, end stage cirrhosis, or other major medical problems are typically not treated with interferon.

In addition, interferon therapy for patients with HBV-related cirrhosis decreases significantly the hepatocellular carcinoma (HCC) rate, particularly in patients with a larger amount of serum HBV DNA. In patients with HBeAg-positive compensated cirrhosis, virological, and biochemical remission following interferon therapy is associated with improved survival. In patients with chronic HBV infection, the clearance of HBeAg after treatment with interferon-α is associated with improved clinical outcomes. The standard duration of therapy is considered 16 weeks. Patients who exhibit a low level of viral replication at the end of the standard regimen benefit most from prolonged treatment.

In some embodiments, the methods of the present disclosure include administering to a subject having an HBV infection or HBV-associate disease a reverse transcriptase inhibitor. In some embodiments, the methods of the present disclosure include administering to a subject having an HBV infection or HBV-associate disease a reverse transcriptase inhibitor and an immune stimulator.

The dsRNA agent and an additional therapeutic agent or treatment may be administered at the same time or in the same combination, e.g., parenterally, or the additional therapeutic agent can be administered as part of a separate composition or at separate times or by another method known in the art or described herein.

The present disclosure also provides methods of using a dsRNA agent or a composition containing a dsRNA agent as described herein to reduce or inhibit HBV expression in a cell. In yet other aspects, use of a dsRNA agent or a composition comprising a dsRNA agent as described herein for the manufacture of a medicament for reducing or inhibiting HBV gene expression in a cell are provided. In still other aspects, the present disclosure provides a dsRNA agent or a composition comprising a dsRNA agent disclosed herein for use in reducing or inhibiting HBV replication in a cell. In yet other aspects, use of a dsRNA agent or a composition comprising a dsRNA agent disclosed herein for the manufacture of a medicament for reducing or inhibiting HBV replication in a cell are provided. The methods and uses include contacting the cell with a dsRNA agent, as disclosed herein and maintaining the cell for a time sufficient to obtain degradation of the mRNA transcript of an HBV gene, thereby inhibiting expression of the HBV gene or inhibiting HBV replication in the cell.

In the aforementioned methods and uses, the cell may be contacted in vitro or in vivo, i.e., the cell may be within a subject.

A cell suitable for treatment using the methods of as disclosed herein may be any cell that expresses an HBV gene, e.g., a cell infected with HBV, a cell comprising an expression vector comprising an HBV genome or portion of an HBV gene, or a transgenic mouse expressing an HBV gene. A cell suitable for use in the methods and uses as disclosed herein may be a mammalian cell, e.g., a primate cell (such as a human cell or a non-human primate cell, e.g., a monkey cell or a chimpanzee cell) or a non-primate cell (such as a mouse cell, a rat cell, or other mammalian cell). In certain embodiments, the cell is a cell that can be infected by HBV. In certain embodiments, the cell is a human cell, e.g., a human liver cell.

HBV gene expression may be inhibited in the cell by at least 80%, 85%, 90%, or 95%, or more, e.g., to below the level of detection of the assay.

HBV replication may be inhibited in the cell by at least 80%, 85%, 90%, or 95%, or more, e.g., to below the level of detection of the assay.

The in vivo methods and uses as disclosed herein may include administering to a subject a composition containing a dsRNA agent, where the dsRNA agent includes a nucleotide sequence that is complementary to at least a part of an RNA transcript of the HBV gene of the mammal to be treated. When the organism to be treated is a human, the composition can be administered by any means known in the art including, but not limited to subcutaneous, intravenous, or intramuscular administration. In some embodiments, the compositions are administered by subcutaneous injection. In some embodiments, the dsRNA agent is formulated to administer the entire dose as a single injection. In some embodiments, the present disclosure provides compositions that are formulated for organ-specific (e.g., hepatic) intraarterial, intratumoral, intradermal, intravitreal injection, ocular topical, ophthalmic (eye drops), nebulization, ocular topical or other topical routes, suppository, or oral administration.

In one aspect, the present disclosure also provides methods for inhibiting the expression of an HBV gene in a mammal, e.g., a human. The present disclosure also provides a composition comprising a dsRNA agent that targets an HBV gene in a cell of a mammal for use in inhibiting expression of the HBV gene in the mammal. In another aspect, the present disclosure provides use of a dsRNA agent that targets an HBV gene in a cell of a mammal in the manufacture of a medicament for inhibiting expression of the HBV gene in the mammal.

The methods and uses include administering to the mammal, e.g., a human, a composition comprising a dsRNA agent that targets an HBV gene in a cell of the mammal and maintaining the mammal for a time sufficient to obtain degradation of the mRNA transcript of the HBV gene, thereby inhibiting expression of the HBV gene in the mammal.

In certain embodiments, reduction in gene expression can be assessed in a peripheral blood sample of the dsRNA agent-administered subject by any methods known it the art, e.g., qRT-PCR, described herein. Reduction in protein production can be assessed by any methods known it the art and by methods, e.g., ELISA or western blotting, described herein. Clinically acceptable methods for determining gene and protein expression levels are used as appropriate. In certain embodiments, a puncture liver biopsy sample serves as the tissue material for monitoring the reduction in HBV gene or protein expression. In some other embodiments, a blood sample serves as the tissue material for monitoring the reduction in HBV gene or protein expression.

In some embodiments, verification of RISC medicated cleavage of target in vivo following administration of dsRNA agent is done by performing 5'-RACE or modifications of the protocol as known in the art (Lasham A et al., (2010) *Nucleic Acid Res.*, 38 (3) p-e19) (Zimmermann et al. (2006) Nature 441: 111-4).

The invention is further illustrated by the following examples, which should not be construed as limiting.

EXAMPLES

Example 1 dsRNA Agent Synthesis

Source of Reagents

Where the source of a reagent is not specifically given herein, such reagent can be obtained from any supplier of reagents for molecular biology at a quality/purity standard for application in molecular biology.

dsRNA Agent Design

As described in WO/2016/077321, the selection of dsRNA designs targeting HBV was driven by two primary factors: a) potency, and b) the desire to employ agents with near-perfect matches and with greater than 90% fractional coverage of the large number of public HBV sequences of all known genotypes (A through H). The coordinates for the RNA agent selection were determined relative to the NCBI HBV reference genome sequence NC_003977.1 (GenBank Accession No. GI:21326584 (SEQ ID NO:1)). A first set of RNA agents containing structure-activity modifications, including various 2'-O-methyl and 2'-fluoro substitution patterns, centered on two adjacent regions of the HBV genome coding for surface antigen (HbSAg) and the HBV polymerase, was designed, synthesized, and screened in vitro. A second set of agents targeting additional regions in the HBV genome, in particular positions 1581-1599 of SEQ ID NO:1, the region that codes for HbSAg, polymerase, and the X gene, was also designed, synthesized, and screened in vitro. Selected sequences were subjected to further chemical modification and testing. These duplex designs are provided in WO2016/077321 (the entire contents of which are incorporated herein by reference); a detailed list of unmodified HBV sense and antisense strand nucleotide sequences is provided in Tables 3, 6, 12, 22, and 25 in WO2016/077321, and a detailed list of modified HBV sense and antisense strand nucleotide sequences is provided in Tables 4, 7, 13, 23, and 26 in WO2016/077321. Results from the screening assays performed with those agents are also provided therein.

Those studies identified the duplex AD-66810 having an antisense strand with the modified nucleotide sequence 5'-usGfsugaAfgCfGfaaguGfcAfcacsusu-3' (SEQ ID NO:13) and a sense strand with the modified nucleotide sequence 5'-gsusguGfcAfCfJfucgcuucaca-3' (SEQ ID NO:29) wherein a, c, g, and u are 2'-O-methyladenosine-3'-phosphate, 2'-O-methylcytidine-3'-phosphate, 2'-O-methylguanosine-3'-phosphate, and 2'-O-methyluridine-3'-phosphate, respectively; Af, Cf, Gf, and Uf are 2'-fluoroadenosine-3'-phosphate, 2'-fluorocytidine-3'-phosphate, 2'-fluoroguanosine-3'-phosphate, and 2'-fluorouridine-3'-phosphate, respectively; and s is a phosphorothioate linkage; and wherein an N-acetylgalactosamine moiety N-[tris(GalNAc-alkyl)-amidodecanoyl)]-4-hydroxyprolinol (also known as (Hyp-(GalNAc-alkyl)$_3$) or referred to herein as L96) is covalently linked to the 3' end of the sense strand.

A further study provided herein was performed to identify potent and specific dsRNA agent molecules based on the previously identified sequence AD-66810, targeting the X transcript of human hepatitis B virus (HBV; U95551). To achieve this objective, a series of chemically modified dsRNA agents were designed, synthesized, and tested for activity in vitro using a Dual-Luc reporter based assay and the HepG2.2.15 cell line. All compounds were conjugated to a triantennary N-acetylgalactosamine (GalNAc) ligand (L96) covalently linked to the 3' end of the sense strand.

dsRNA Agent Synthesis

HBV sense and antisense strand sequences were synthesized at 1 µmol scale on a Mermade 192 synthesizer (BioAutomation) using solid support mediated phosphoramidite chemistry. The solid support was controlled pore glass (500 A) loaded with custom GalNAc ligand or universal solid support (AM biochemical). Ancillary synthesis reagents, 2'-F and 2'-O-Methyl RNA, and deoxy phosphoramidites were obtained from Thermo-Fisher™ (Milwaukee, Wis.) and Hongene (China). 2'F 2'-O-Methyl, GNA (glycol nucleic acids), 5'-phosphate, and abasic modifications were introduced employing the corresponding phosphoramidites. Synthesis of 3' GalNAc conjugated single strands was performed on a GalNAc modified CPG support. Custom CPG universal solid support was used for the synthesis of antisense single strands. Coupling time for all phosphoramidites (100 mM in acetonitrile) was 5 minutes employing 5-Ethylthio-1H-tetrazole (ETT) as activator (0.6 M in acetonitrile). Phosphorothioate linkages were generated using a 50 mM solution of 3-((Dimethylamino-methylidene)amino)-3H-1,2,4-dithiazole-3-thione (DDTT, obtained from Chemgenes (Wilmington, Mass., USA)) in anhydrous acetonitrile/pyridine (1:1 v/v). Oxidation time was 3 minutes. All sequences were synthesized with final removal of the DMT group ("DMT off").

Upon completion of the solid phase synthesis, oligoribonucleotides were cleaved from the solid support and deprotected in sealed 96 deep well plates using 200 µL Aqueous Methylamine reagents at 60° C. for 20 minutes. At the end of cleavage and deprotection step, the synthesis plate was allowed to come to room temperature and was precipitated by addition of 1 mL of acetontile: ethanol mixture (9:1). The plates were cooled at −80° C. for 2 hours, supernatant decanted carefully with the aid of a multi-channel pipette. The oligonucleotide pellet was re-suspended in 20 mM NaOAc buffer and was desalted using a 5 mL HiTrap™ size exclusion column (GE Healthcare™) on an AKTA Purifier System equipped with an A905 autosampler and a Frac 950 fraction collector. Desalted samples were collected in 96-well plates. Samples from each sequence were analyzed by LC-MS to confirm the identity, UV (260 nm) for quantification, and a selected set of samples by IEX chromatography to determine purity.

Annealing of HBV single strands was performed on a Tecan liquid handling robot. Equimolar mixture of sense and antisense single strands were combined and annealed in 96-well plates. After combining the complementary single strands, the 96-well plate was sealed tightly and heated in an oven at 100° C. for 10 minutes and allowed to come slowly to room temperature over a period 2-3 hours. The concentration of each duplex was normalized to 10 µM in 1×PBS.

Abbreviations for modified nucleotide monomers disclosed herein are shown in Table 1. Table 2 shows AD-66810 and the HBV dsRNA agents synthesized using the above methods.

TABLE 1

Abbreviations of nucleotide monomers used in modified nucleic acid sequence representation. It will be understood that, unless otherwise indicated, these monomers, when present in an oligonucleotide, are mutually linked by 5'-3'-phosphodiester bonds.

| Abbreviation | Nucleotide(s) |
| --- | --- |
| A | adenosine-3'-phosphate |
| Af | 2'-fluoroadenosine-3'-phosphate |
| Afs | 2'-fluoroadenosine-3'-phosphorothioate |
| As | adenosine-3'-phosphorothioate |
| C | cytidine-3'-phosphate |
| Cf | 2'-fluorocytidine-3'-phosphate |
| Cfs | 2'-fluorocytidine-3'-phosphorothioate |
| Cs | cytidine-3'-phosphorothioate |
| G | guanosine-3'-phosphate |
| Gf | 2'-fluoroguanosine-3'-phosphate |
| Gfs | 2'-fluoroguanosine-3'-phosphorothioate |
| Gs | guanosine-3'-phosphorothioate |
| T | 5'-methyluridine-3'-phosphate |
| Tf | 2'-fluoro-5-methyluridine-3'-phosphate |
| Tfs | 2'-fluoro-5-methyluridine-3'-phosphorothioate |
| Ts | 5-methyluridine-3'-phosphorothioate |
| U | uridine-3'-phosphate |
| Uf | 2'-fluorouridine-3'-phosphate |
| Ufs | 2'-fluorouridine-3'-phosphorothioate |
| Us | uridine-3'-phosphorothioate |
| a | 2'-O-methyladenosine-3'-phosphate |
| as | 2'-O-methyladenosine-3'-phosphorothioate |
| c | 2'-O-methylcytidine-3'-phosphate |
| cs | 2'-O-methylcytidine-3'-phosphorothioate |
| g | 2'-O-methylguanosine-3'-phosphate |
| gs | 2'-O-methylguanosine-3'-phosphorothioate |
| t | 2'-O-methyl-5-methyluridine-3'-phosphate |
| ts | 2'-O-methyl-5-methyluridine-3'-phosphorothioate |
| u | 2'-O-methyluridine-3'-phosphate |
| us | 2'-O-methyluridine-3'-phosphorothioate |
| s | phosphorothioate linkage |
| L96 | N-[tris(GalNAc-alkyl)-amidodecanoyl)]-4-hydroxyprolinol (or "Hyp-(GalNAc-alkyl)3") |
| (Agn) | adenosine-glycol nucleic acid (GNA) |
| (Asn) | adenosine-serinol-nucleic acid (SNA) |
| (Gsn) | guanosine-serinol-nucleic acid (SNA) |
| dA | 2'-deoxyadenosine-3'-phosphate |
| dAs | 2'-deoxyadenosine-3'-phosphorothioate |
| dC | 2'-deoxycytidine-3'-phosphate |
| dCs | 2'-deoxycytidine-3'-phosphorothioate |
| dG | 2'-deoxyguanosine-3'-phosphate |
| dGs | 2'-deoxyguanosine-3'-phosphorothioate |
| dT | 2'-deoxythymidine-3'-phosphate |
| dTs | 2'-deoxythymidine-3'-phosphorothioate |
| dU | 2'-deoxyuridine |
| dUs | 2'-deoxyuridine-3'-phosphorothioate |

TABLE 2

Modified nucleotide sequences of GalNAc-conjugated HBV dsRNA agent

| DuplexID | Sense Sequence (5' to 3') | SEQ ID | Antisense Sequence (5' to 3') | SEQ ID |
|---|---|---|---|---|
| AD-66810 | gsusguGfcAfCfUfucgcuucacaL96 | 10 | usGfsugaAfgCfGfaaguGfcAfcacsusu | 13 |
| AD-192282 | gsusguGfcAfCfUfucgcuucacaL96 | 10 | usGfsuga(Agn)gCfGfaaguGfcAfdCacsusu | 14 |
| AD-192289 | gsusgugcdAcdTucgcuucacaL96 | 11 | usdGsuga(Asn)gcgaadGudGcacacsusu | 15 |
| AD-81890 | gsusguGfcAfCfUfucgcuucacaL96 | 10 | usGfsuga(Agn)gCfGfaaguGfcAfcacsusu | 16 |
| AD-81892 | gsusguGfcAfCfUfucgcuucacaL96 | 10 | usGfsuga(Agn)gcgaaguGfcAfcacsusu | 17 |
| AD-192290 | gsusgugcadCdTucgcuucacaL96 | 12 | usdGsuga(Asn)gcgaadGudGcacacsusu | 15 |
| AD-192283 | gsusguGfcAfCfUfucgcuucacaL96 | 10 | usGfsuga(Agn)gcgaaguGfdCAfcacsusu | 18 |
| AD-192291 | gsusgugcdAcdTucgcuucacaL96 | 11 | usdGsugaa(Gsn)cgaadGudGcacacsusu | 19 |
| AD-192277 | gsusguGfcAfCfUfucgcuucacaL96 | 10 | usGfsudGa(Agn)gCfGfaaguGfcAfcacsusu | 20 |
| AD-192284 | gsusguGfcAfCfUfucgcuucacaL96 | 10 | usGfsuga(Agn)gcgaaguGfcAfdCacsusu | 21 |
| AD-192292 | gsusgugcadCdTucgcuucacaL96 | 12 | usdGsugaa(Gsn)cgaadGudGcacacsusu | 19 |
| AD-192285 | gsusgugcdAcdTucgcuucacaL96 | 11 | usdGsuga(Agn)gcgaadGudGcacacsusu | 22 |
| AD-192293 | gsusguGfcAfCfUfucgcuucacaL96 | 10 | usGfsudGadAgdCGfaaguGfcAfcacsusu | 23 |
| AD-192279 | gsusguGfcAfCfUfucgcuucacaL96 | 10 | usGfsuga(Agn)dGCfGfaaguGfcAfcacsusu | 24 |
| AD-192286 | gsusgugcadCdTucgcuucacaL96 | 12 | usdGsuga(Agn)gcgaadGudGcacacsusu | 22 |
| AD-192294 | gsusguGfcAfCfUfucgcuucacaL96 | 10 | usGfsudGadAgdCGfaaguGfcAfdCacsusu | 25 |
| AD-192280 | gsusguGfcAfCfUfucgcuucacaL96 | 10 | usGfsuga(Agn)gdCGfaaguGfcAfcacsusu | 26 |
| AD-192287 | gsusgugcdAcdTucgcuucacaL96 | 11 | usdGsuga(Agn)gcgaadGudGcdAcacsusu | 27 |
| AD-192281 | gsusguGfcAfCfUfucgcuucacaL96 | 10 | usGfsuga(Agn)gCfGfaaguGfdCAfcacsusu | 28 |
| AD-192288 | gsusgugcadCdTucgcuucacaL96 | 12 | usdGsuga(Agn)gcgaadGudGcdAcacsusu | 27 |

Example 2

In Vitro Screening of dsRNA Agent Duplexes

Dual-Glo® Luciferase Assay:

Cos7 cells (ATCC®, Manassas, Va.) were grown to near confluence at 37° C. in an atmosphere of 5% C02 in DMEM (ATCC) supplemented with 1000 FBS, before being released from the plate by trypsinization. Transfection of Cos7 cells with double stranded agents and psiCHECK2-HBV (an expression vector comprising a nucleotide sequence encoding a portion of a consensus wild-type HBV sequence; SEQ ID NO:5), or double stranded agents and psiCHECK2 vectors expressing the nucleotide sequence of HBV genotype A, C, E, or F (SEQ ID NOs:6, 7, 8, or 9, respectively), were carried out by adding 5 μl of RNA duplexes and 5 μl of psiCHECK2-HBV (or psiCHECK2-HBV genotype A, C, E, or F) plasmid per well along with 5 μl of Opti-MEM® plus 0.1 μl of Lipofectamine™ RNAiMax per well (Invitrogen™, Carlsbad Calif. cat #13778-150) and then incubated at room temperature for 15 minutes. The mixture was then added to the cells, which were re-suspended in 35 μl of fresh complete media. The transfected cells were incubated at 37° C. in an atmosphere of 5% $CO_2$.

Forty-eight hours after the dsRNA agents and psiCHECK2 plasmid were transfected; Firefly (transfection control) and Rinella (fused to HBV target sequence) luciferase were measured. First, media was removed from cells. Then Firefly luciferase activity was measured by adding 20 μl of Dual-Glo® Luciferase Reagent equal to the culture medium volume to each well and mix. The mixture was incubated at room temperature for 30 minutes before luminescence (500 nm) was measured on a Spectramax® (Molecular Devices) to detect the Firefly luciferase signal. *Renilla* luciferase activity was measured by adding 20 μl of room temperature of Dual-Glo® Stop & Glo® Reagent was added to each well and the plates were incubated for 10-15 minutes before luminescence was again measured to determine the *Renilla* luciferase signal. The Dual-Glo® Stop & Glo® Reagent, quenches the firefly luciferase signal and sustained luminescence for the *Renilla* luciferase reaction. dsRNA agent activity was determined by normalizing the *Renilla* (HBV) signal to the Firefly (control) signal within each well. The magnitude of dsRNA agent activity was then assessed relative to cells that were transfected with the same vector but were not treated with dsRNA agent or were treated with a non-targeting dsRNA agent. All transfections were done at n=2 or greater.

The results of these assays using the agents listed in Table 2 are provided in Table 3.

HepG2.2.15 and PLC In Vitro Screening:

HepG2.2.15 and PLC (human hepatoma cells; ATCC® CRL-8024) cells were grown to near confluence at 37° C. in an atmosphere of 5% $CO_2$ in DMEM or EMEM medium (ATCC) supplemented, respectively, with 10% FBS (ATCC) before being released from the plate by trypsinization. Reverse transfection was carried out by adding 5 μl of dsRNA agent duplexes per well into a 96-well plate along with 14.8 μl of Opti-MEM® plus 0.241 of Lipofectamine™ RNAiMax per well (Invitrogen™, Carlsbad Calif. cat #13778-150) and incubated at room temperature for 15 minutes. Eighty micro liters of complete growth media without antibiotic containing $2\times10^4$ HepG2.2.15 or PLC cells were then added. Cells were incubated for 24, 48, and 72 hours prior to RNA purification.

The results of these assays using the agents listed in Table 2 are provided in Table 4.

Total RNA Isolation Using MagMAX-96 Total RNA Isolation Kit (Applied Biosystem, Forer City Calif., Part #: AM1830):

Cells were harvested and lysed in 140 μl of Lysis/Binding Solution then mixed for 1 minute at 850 rpm using an Eppendorf™ Thermomixer (the mixing speed was the same throughout the process). Twenty microliters of magnetic beads and Lysis/Binding Enhancer mixture were added into cell-lysate and mixed for 5 minutes. Magnetic beads were captured using magnetic stand and the supernatant was removed without disturbing the beads. After removing supernatant, magnetic beads were washed with Wash Solution 1 (isopropanol added) and mixed for 1 minute. Beads were captured again and supernatant removed. Beads were then washed with 150 μl Wash Solution 2 (Ethanol added), captured and supernatant was removed. Fifty μl of DNase mixture (MagMax turbo DNase Buffer and Turbo DNase) was then added to the beads and they were mixed for 10 to 15 minutes. After mixing, 100 μl of RNA Rebinding Solution was added and mixed for 3 minutes. Supernatant was removed and magnetic beads were washed again with 150 μl Wash Solution 2 and mixed for 1 minute and supernatant was removed completely. The magnetic beads were mixed for 2 minutes to dry before RNA was eluted with 50 μl of water.

cDNA Synthesis Using ABI High Capacity cDNA Reverse Transcription Kit (Applied Biosystems, Foster City, Calif. Cat #4368813):

A master mix of 2 μl 10× Buffer, 0.8 μl 25×dNTPs, 2 μl Random primers, 1 μl Reverse Transcriptase, 1 μl RNase inhibitor and 3.2 μl of $H_2O$ per reaction was added into 10 μl total RNA. cDNA was generated using a Bio-Rad® C-1000 or S-1000 thermal cycler (Hercules, Calif.) through the following steps: 25° C. 10 min, 37° C. 120 min, 85° C. 5 sec, 4° C. hold.

Real Time PCR:

Two μl of cDNA were added to a master mix containing 0.5 μl of human GAPDH TaqMan Probe (Applied Biosystems Cat #4319413E), 1 μl SORF2 specific TaqMan® probe and 5 μl Lightcycler 480 probe master mix (Roche Cat #04887301001) per well in a 384 well plates (Roche cat #04887301001). Real time PCR was done in a LightCycler480 Real Time PCR system (Roche) using the DDCt (RQ) assay. To calculate relative fold change, real time data were analyzed using the DDCt method and normalized to assays performed with cells transfected with AD-1955, or mock transfected cells.

To calculate relative fold change, real time data were analyzed using the DDCt method and normalized to assays performed with cells transfected with a non-targeting control dsRNA agent.

Example 3

Transfection of GalNAc Conjugated HBV-Targeting dsRNA Agents in Dual-Luc System

Silencing of HBV mRNA following transfection with each of the conjugated dsRNA agents is shown in Table 3. Each dsRNA agent was tested by transfection in Cos7 cells at dsRNA agent concentrations of 50 nM, 10 nM, and 0.1 nM. Based on the screening results, 7 out of the 20 dsRNA agents demonstrated comparable potency to the AD-66810 parent.

TABLE 3

Screening Results using Dual-Luc assay of Conjugated HBV dsRNA agents Transfected at 50 nM, 10 nM, or 1 nM

| | Mean ± SD HBV dsRNA agent Message Remaining (%)[a] | | |
|---|---|---|---|
| Duplex ID | 50 nM | 10 nM | 0.1 nM |
| AD-66810 | 43.18 ± 5.33 | 43.83 ± 3.07 | 108.98 ± 13.64 |
| AD-192282 | 51.82 ± 2.45 | 58.09 ± 12.10 | 121.63 ± 7.49 |
| AD-192289 | 71.82 ± 12.28 | 84.84 ± 6.00 | 115.35 ± 16.01 |
| AD-81890 | 47.09 ± 3.36 | 53.70 ± 7.58 | 112.10 ± 15.95 |
| AD-81892 | 62.70 ± 1.42 | 55.04 ± 6.21 | 107.79 ± 14.23 |
| AD-192290 | 78.23 ± 5.63 | 77.77 ± 6.00 | 98.24 ± 4.13 |
| AD-192283 | 54.62 ± 3.97 | 46.70 ± 9.86 | 113.80 ± 21.17 |
| AD-192291 | 73.97 ± 6.80 | 64.32 ± 5.52 | 111.71 ± 10.18 |
| AD-192277 | 43.08 ± 1.58 | 34.82 ± 4.23 | 103.32 ± 12.95 |
| AD-192284 | 70.20 ± 5.87 | 54.10 ± 3.08 | 119.01 ± 12.73 |
| AD-192292 | 70.91 ± 13.89 | 65.99 ± 3.57 | 102.58 ± 8.12 |
| AD-192285 | 86.15 ± 7.45 | 91.39 ± 8.92 | 116.62 ± 8.93 |
| AD-192293 | 48.05 ± 0.45 | 46.38 ± 6.26 | 120.84 ± 10.62 |
| AD-192279 | 51.29 ± 6.93 | 38.35 ± 2.50 | 114.22 ± 10.41 |
| AD-192286 | 89.16 ± 12.87 | 88.74 ± 4.44 | 118.16 ± 12.97 |
| AD-192294 | 54.36 ± 5.03 | 41.89 ± 5.61 | 114.19 ± 11.55 |
| AD-192280 | 49.20 ± 7.13 | 57.22 ± 14.47 | 116.35 ± 6.87 |
| AD-192287 | 81.73 ± 14.38 | 84.10 ± 10.24 | 127.11 ± 12.61 |
| AD-192281 | 38.74 ± 4.01 | 38.45 ± 4.54 | 120.99 ± 7.00 |
| AD-192288 | 85.37 ± 9.30 | 86.14 ± 5.32 | 118.09 ± 9.30 |

Abbreviations: ID = identification; SD = standard deviation
[a]Fraction of remaining relative HBV expression (versus control transfected cells) 48 hours after transfection of screening set of HBV dsRNA agents.

Example 4

Transfection of GalNAc Conjugated HBV-Targeting dsRNA Agents in HepG2.2.15 Cells Silencing of HBV mRNA (PORF1 and SORF2 mRNA as determined using forward and reverse primers and a TaqMan probe) in HepG2.2.15 cells following transfection with each of the conjugated dsRNA agents is shown in Table 4. Overall, more robust silencing of PORF1 and SORF2 viral transcripts was observed in HepG2.2.15 cells compared to the silencing observed in the Dual-Luc overexpression system, with 10 dsRNA agents having had comparable potency to the parent molecule AD-66810 parent. Similar dsRNA agent activity was observed for against PORF1 and SORF2 mRNAs, which was expected since dsRNA agent target sites are present in both transcripts.

TABLE 4

Screening Results using HepG2.2.15 of Conjugated HBV dsRNA agents Transfected at 50 nM, 10 nM, or 1 nM

| DuplexID | % Remain PORF1 (10 nM)[a] | SD | % Remain PORF1 (0.1 nM)[a] | SD | % Remain SORF2 (10 nM)[a] | SD | % Remain SORF2 (0.1 nM)[a] | SD |
|---|---|---|---|---|---|---|---|---|
| AD-66810 | 22.9 | 0.2 | 114.3 | 22.4 | 22.2 | 0.3 | 110.0 | 19.3 |
| AD-192282 | 29.7 | 2.2 | 84.9 | 1.2 | 28.5 | 1.3 | 79.9 | 1.6 |
| AD-192289 | 71.1 | 13.7 | 83.8 | 9.9 | 72.7 | 16.2 | 92.1 | 10.8 |
| AD-81890 | 34.2 | 7.1 | 85.5 | 19.6 | 33.7 | 9.1 | 93.4 | 26.6 |
| AD-81892 | 32.9 | 0.1 | 82.2 | 8.5 | 28.1 | 2.6 | 79.9 | 9.0 |
| AD-192290 | 72.9 | 19.3 | 86.0 | 7.6 | 63.3 | 9.2 | 92.9 | 12.7 |
| AD-192283 | 38.7 | 18.5 | 82.0 | 18.7 | 31.0 | 14.5 | 80.2 | 12.9 |
| AD-192291 | 62.9 | 16.1 | 80.2 | 17.6 | 54.0 | 13.3 | 86.2 | 20.1 |
| AD-192277 | 33.9 | 15.4 | 74.2 | 17.4 | 29.0 | 11.9 | 76.9 | 15.7 |
| AD-192284 | 33.4 | 8.5 | 82.4 | 6.5 | 25.9 | 8.2 | 78.6 | 2.7 |
| AD-192292 | 52.2 | 5.3 | 80.1 | 0.9 | 47.1 | 6.2 | 84.4 | 7.8 |
| AD-192285 | 85.5 | 1.0 | 85.8 | 10.6 | 73.1 | 8.5 | 84.8 | 2.9 |
| AD-192293 | 26.9 | 1.8 | 79.1 | 21.9 | 24.0 | 1.7 | 79.7 | 16.3 |
| AD-192279 | 27.2 | 4.5 | 81.0 | 11.1 | 22.7 | 4.7 | 77.8 | 13.7 |
| AD-192286 | 91.6 | 2.5 | 92.4 | 5.8 | 80.3 | 4.7 | 93.1 | 4.6 |
| AD-192294 | 25.7 | 2.1 | 78.2 | 4.3 | 23.1 | 1.5 | 78.6 | 10.8 |
| AD-192280 | 39.7 | 11.8 | 83.9 | 20.8 | 30.1 | 8.6 | 83.0 | 8.9 |
| AD-192287 | 66.1 | 1.2 | 81.1 | 7.5 | 59.3 | 6.3 | 80.9 | 7.5 |
| AD-192281 | 28.1 | 8.0 | 79.6 | 11.3 | 23.2 | 5.2 | 78.9 | 4.6 |
| AD-192288 | 73.1 | 0.2 | 95.4 | 14.5 | 62.5 | 7.6 | 104.4 | 13.3 |

Abbreviations: SD = standard deviation
[a]Fraction of remaining relative HBV expression (versus control transfected cells) 24 hours after transfection of screening set of HBV dsRNA agents.

Based on the above studies, duplex AD-81890 was selected for further analysis.

Example 5

Evaluation of AD-81890 Pharmacology in an Adeno-Associated HBV Mouse Model Following a Single Subcutaneous Injection Pharmacology of AD-81890 was assayed in an adeno-associated HBV (HBV-AAV) mouse model. AAV8-HBV (SignaGen Laboratories) was diluted in 1×PBS to a final concentration of $2 \times 10^{12}$ GC/mL. Male C57BL/6 mice 6-8 weeks of age were injected intravenously via lateral tail vein with $2 \times 10^{11}$ GC/mouse in a fixed volume of 100 µL.

AD-81890 was diluted with sterile 1×PBS and administered with a variable volume of 10 µl/g. Animals received a single SC dose of AD-81890 at 0.3, 1, or 3 mg/kg, and blood was collected at Day −24, −2, 0, 14, 21, 33, 47, 59, and 74 post dose via retroorbital sinus as described in Table 5.

TABLE 5

AD-81890 Single Dose AAV-HBV Study Design

| Group | Compound | Dose on Day 0 (mg/kg) | No. of Animals | Serum Collection Time Points |
|---|---|---|---|---|
| 1 | PBS | 0 | 9 | Days −24, −2, 0, 14, 21, 33, 47, 59, 74 |
| 2 | AD-81890 | 0.3 | 9[a] | |
| 3 | | 1 | 9 | |
| 4 | | 3 | 9 | |

Abbreviations: No. = number; PBS = phosphate buffered saline
[a]n = 8 animals on Day 47; n = 6 on Day 59; n = 5 on Day 72, animals euthanized due to fight wounds After collection, blood was allowed to clot for 30 minutes and was then spun in a microcentrifuge for 10 min at 13,000 rpm and 4° C. Serum was aspirated and stored at −20° C.

Hepatitis B Virus surface antigen protein levels were evaluated via ELISA (BioTang, Waltham, Mass.). The US Biologics (Memphis, Tenn.) HBsAg protein was used to generate the standard curve. Serum samples were diluted at 1×PBS (Gibco, Gaithersburg, Md.) at 1:2000 or 1:500 and evaluated using the ELISA protocol with minor modifications. Briefly, 50 µL/well of diluted serum or standard were loaded into the plate and incubated for 1 h at 37° C. After this incubation, 50 µL/well enzyme conjugate was added to each well, and the plate was incubated at 37° C. for 30 min. The plate was washed with 3 times 300 µL/well 1× wash buffer, then blotted until all liquid was removed from the wells, 100 µL/well substrate was added, and plates were incubated at 37° C. for 30 min. Finally, an additional 100 µL/well of stop solution was added and absorbance was measured at a wavelength of 450 nm. In any instance where calculated HBsAg level fell below the lower limit of quantitation (LLOQ) of the assay, values were recorded as the LLOQ (i.e., 313 ng/mL).

Figure 2A:
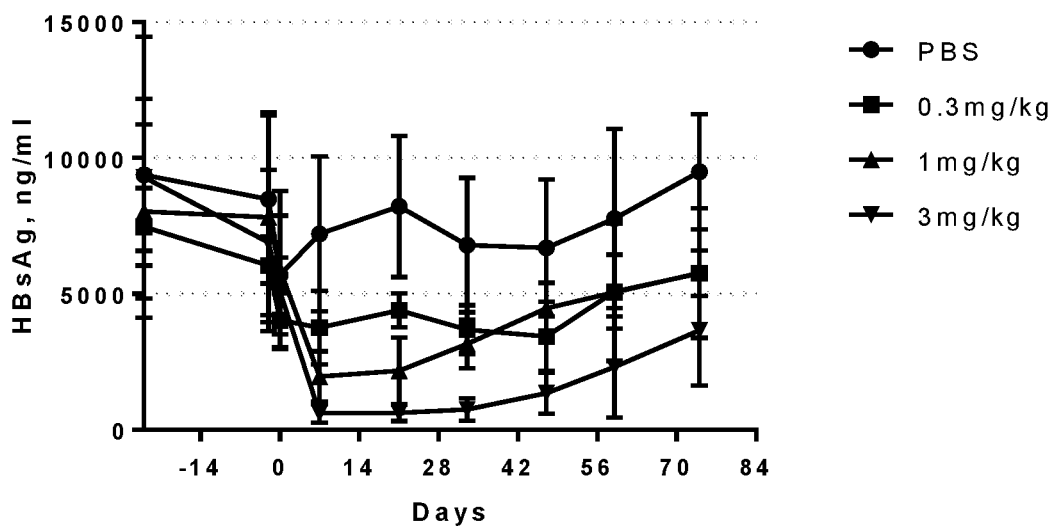
FIGS. 2A-2B show the (A) serum HBsAg concentrations (ng/mL) and (B) serum HBsAg levels relative to pre-dose in the AAV-HBV mouse model.
Figure 2B:
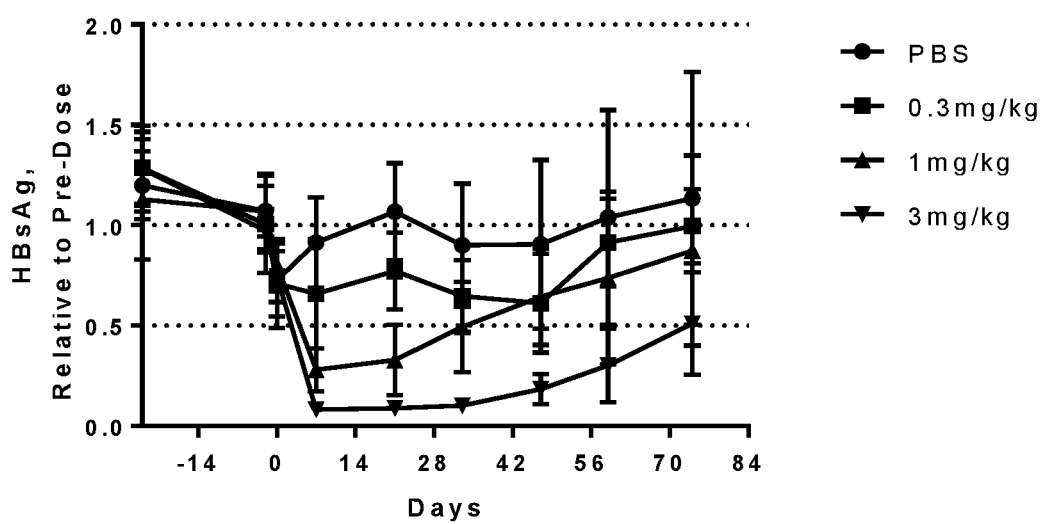

Mean±SD serum HBsAg concentrations in HBV-AAV mice following a single subcutaneous (SC) dose of AD-81890 are shown in FIG. 2A. Mean±SD serum HBsAg levels in HBV-AAV mice relative to baseline are shown in FIG. 2B. A single SC injection of AD-81890 at 0.3, 1, or 3 mg/kg led to potent and sustained reduction of serum HBsAg concentrations in HBV-AAV mice, with a maximum reduction of 92% observed on Day 7 in the highest (3 mg/kg) AD-81890 dose group. The maximum level of reduction was maintained in the highest dose group through Day 33 after which HBsAg levels began returning towards baseline (FIG. 2B). Intermediate reductions in serum HBsAg concentrations were observed in the 0.3 mg/kg and 1 mg/kg AD081890 dose groups with a maximum reduction on Day 7 of 23% and 72%, respectively. HBsAg levels in both the 0.3 mg/kg and 1 mg/kg AD-81890 dose groups returned to baseline levels by study completion (Day 74).

Example 6

Evaluation of AD-81890 Pharmacology in an Adeno-Associated HBV Mouse Model Following Multiple Subcutaneous Injections Pharmacology of AD-81890 was assayed in an adeno-associated HBV (HBV-AAV) mouse model. AAV8-HBV (SignaGen Laboratories) was diluted in 1×PBS to a final concentration of 2×1012 GC/mL. Male C57BL/6 mice 6-8 weeks of age were injected intravenously via lateral tail vein with 2×1011 GC/mouse in a fixed volume of 100 µL.

Each AD-66810 and AD-81890 were diluted with sterile 1×DPBS and administered with a variable volume of 10 ul/g. Animals received AD-66810 at 1 mg/kg given Q2W×6, or a single dose of AD-81890 at 9 mg/kg, or multiple doses of AD-81890 at 1 or 3 mg/kg given Q2W×6 or QM×3. Serum was collected from animals at multiple timepoints as described in Table 6. Blood was collected via retroorbital sinus as described in Table 6.

TABLE 6

AD-81890 Multiple Dose AAV-HBV Study Design

| Group | Compound | Dose on Day 0 (mg/kg) | Regimen | N= | Serum Collections |
|---|---|---|---|---|---|
| 1 | PBS | 0 | Q2W×6 | 6 | Day −55, −27, −13, 0, 14, 28, 42, 56, 70, 84, 98, 111, 126 |
| 2 | AD-66810 | 1 | Q2W×6 | 6 | |
| 3 | AD-81890 | 1 | Q2W×6 | 6 | |
| 4 | | | QM×3 | 6 | |
| 5 | | 3 | Q2W×6 | 6 | |
| 6 | | | QM×3 | 6 | |
| 7 | | 9 | QM×1 | 6 | |

Figure 3:
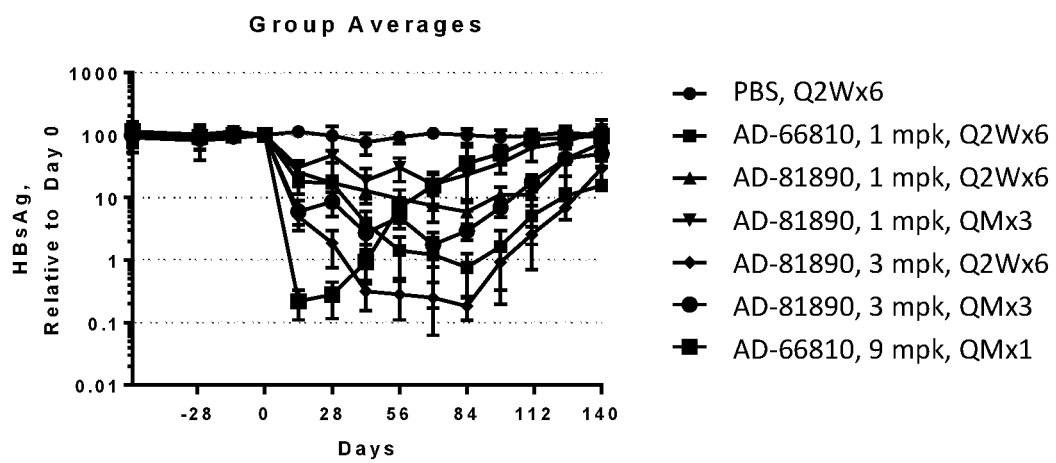
FIG. 3 shows the serum HBsAg levels relative to pre-dose in the AAV-HBV mouse model on Days −55, −27, −13, 0, 14, 28, 42, 56, 84, 112, and 140. Dosing regimens included control (PBS) Q2W×6; AD-66810 (1 mg/kg; Q2W×6); AD-81890 (1 mg/kg; Q2W×6); AD-81890 (1 mg/kg; QM×3); AD-81890 (3 mg/kg; Q2W×6); AD-81890 (3 mg/kg; QM×3); and AD-81890 (9 mg/kg; QM×1). The first dose was administered at Day 0. Each point represents a mean of n of 4-6 animals and the bars represent SD.

Blood samples were processed and ELISA assays were performed as described in the prior example. Results are shown in Table 7 below. Results with standard deviations are shown in FIG. 3.

TABLE 7

AD-81890 Multiple Dose AAV-HBV Results Expressed as Average Log-fold Change

| dsRNA agent | mg/kg | Regimen | Days |  |  |  |  |  |  |  |  |  |  |  |  |
|---|---|---|---|---|---|---|---|---|---|---|---|---|---|---|---|
| | | | −55 | −27 | −13 | 0 | 14 | 28 | 42 | 56 | 70 | 84 | 98 | 111 | 125 | 140 |
| PBS | — | Q2W×6 | −0.04 | −0.09 | −0.05 | 0.00 | 0.06 | −0.01 | −0.11 | −0.03 | 0.03 | 0.00 | −0.03 | −0.01 | 0.04 | 0.00 |
| AD-66810 | 1 | Q2W×6 | 0.02 | −0.05 | 0.00 | 0.00 | −0.74 | −0.77 | −1.41 | −1.84 | −1.91 | −2.12 | −1.78 | −1.29 | −0.97 | −0.81 |
| AD-81890 | 1 | Q2W×6 | 0.02 | −0.04 | 0.06 | 0.00 | −0.59 | −0.76 | −0.89 | −1.02 | −1.13 | −1.23 | −0.95 | −0.95 | −0.39 | −0.13 |
| | 1 | QM×3 | 0.06 | 0.01 | 0.06 | 0.00 | −0.51 | −0.32 | −0.73 | −0.51 | −0.79 | −0.63 | −0.45 | −0.20 | −0.11 | 0.09 |
| | 3 | Q2W×6 | 0.03 | −0.04 | 0.02 | 0.00 | −1.30 | −1.73 | −2.49 | −2.57 | −2.61 | −2.77 | −2.03 | −1.59 | −1.16 | −0.53 |
| | 3 | QM×3 | −0.02 | 0.00 | 0.03 | 0.00 | −1.30 | −1.06 | −1.56 | −1.32 | −1.75 | −1.53 | −1.15 | −0.75 | −0.38 | −0.30 |
| | 9 | QM×1 | 0.06 | −0.03 | 0.00 | 0.00 | −2.71 | −2.60 | −2.03 | −1.16 | −0.81 | −0.45 | −0.29 | −0.07 | −0.04 | −0.01 |

Dose responsive serum HBsAg level was observed in the AAV8-HBV mouse model after AD-81890 administration. A maximum HBsAg reduction of about 2.7 log 10 was observed after a single 9 mg/kg dose or 3 mg/kg q2w×6 of AD-81890. Animals receiving 3 mg/kg q2w×6 had sustained HBsAg reduction of greater than 2 log 10 for a total of approximately 8 weeks.

These in vivo studies demonstrate that AD-81890 is effective in reducing HBsAg in serum in the HBV-AAV mouse model.

Example 7

Specific Off-Target Analysis of AD-81890

A combination of in silico bioinformatics methods and in vitro methods were used to assess potential off-target activity of the antisense strand of AD-81890.

Bioinformatics

A set of dsRNA agents targeting the 'X' gene of the Hepatitis B virus (HBV) subtype ayw (GenBank nucleotide ID U95551; NCBI GeneID: 7276; SEQ ID NO:49) were designed using custom R and Python scripts. The circular U95551 HBV genome has a length of 3182 bases and the 'X' gene CDS region is coded in the NCBI record in the positions 1376-1840. Details of the dsRNA agent design and screening method are provided above and in WO2016/077321.

Transfection Screen of GalNAc-Conjugated dsRNA Agents for Off-Target Detection in HepG2.2.15 Cells To measure off-target inhibition, the response of endogenously expressed transcripts by qPCR was tested in the hepatocyte cell line HepG2.2.15. Cells were transfected in 96-well plates ($2 \times 10^4$ cells per well) with AD-81890 at a range of concentrations from 50 nM to 5 fM using Lipofectamine RNAiMax (ThermoFisher). After 24 hours, RNA was extracted from cells using MagMAX™-96 Total RNA Isolation Kit (ThermoFisher); and cDNA was generated using the ABI High Capacity cDNA reverse transfection kit (ThermoFisher). Samples were assayed for inhibition of HBV mRNA and potential off-target silencing. For quantification by qPCR, HBV expression was assessed using two different custom TaqMan assays, PORF-1 and SORF-2, which recognize different regions of HBV viral transcripts.

To assess off-target silencing, TaqMan probes specific to each potential off-target (Table 8) were used for quantification. qPCR was performed with a LightCycler 480 Real-Time PCR machine (Roche).

TABLE 8

Potential Off-Target Sequences of AD-81890

| Off-Target ID | Off-target Score | Mismatch Position[a] | Accession[b] | Target Gene |
|---|---|---|---|---|
| AD-81890_(Off-1) | 3 | 19, 16, 13 | NM_001040455.1 | SIDT2 |
| AD-81890_(Off-2) | 3.4 | 14, 11, 10 | NM_020861.1 | ZBTB2 |

[a]Mismatch positions are defined with respect to the antisense strand in the 5'-3' direction, therefore, position 1 corresponds to the base complementary to the 5'-most nucleotide of the antisense strand of AD-81890
[b]In case where multiple RefSeq IDs are associated with the same target gene and off-target profile, both IDs are listed.

To determine the extent of on-target (HBV) and potential off-target gene inhibition, relative RNA levels were determined by normalization to human GAPDH RNA expression from the same sample. Results were compared to transfected nonspecific dsRNA agent controls and error is expressed as standard deviation. IC50 of AD-81890 was 0.803 nM against the PORF1 transcript target and 0.766 nM against the SORF2 transcript target. No significant target knockdown was observed against the SIDT2 and ZBTB2 transcripts even at the highest concentration of AD-81890.

The extent of off-target inhibition by AD-81890 was assessed in dose response screens for the 2 potential off-targets from endogenously expressed transcripts in HepG2.2.15. AD-81890 did not inhibit expression for SIDT2 or ZBTB2 at any of the doses tested, while HBV inhibition was dose responsive. Fitting the dose-response data using a four-parameter fit model (XLfit) results in an IC50s of 803 pM and 766 pM for PORF-1 or SORF-2, respectively.

Example 8

In Vitro Analysis of AD-81890 Specificity Using RNA-SEQ in HepG2.2.15 Cells

The impact of dsRNA agent chemistry modification by comparing AD-66810 and AD-81890 in the HBV-expressing HepG2.2.15 cell line was measured using transcriptome-wide changes in expression levels with RNA-Seq. The AD-66810 and AD-81890 molecules have the same nucleotide sequence but differ by the substitution of a single glycol nucleic acid (GNA) at position 6 from the 5' end of molecule of antisense strand (see Table 2).

HepG2.2.15 cells, a HepG2 derived cell line stably transfected with full genome HBV, were diluted with culture media to a final concentration of 187,500 cells/mL, and 80 μL was pipetted into 96-well collagen coated plates (BD Biocoat, Cat #356407) to give a final concentration of 15,000 cells/well.

dsRNA agent stocks were diluted in 1×DPBS to the following concentrations: 1,000 nM or 100 nM. RNAiMAX (ThermoFisher, Cat #13778150) was diluted with Opti-MEM (ThermoFisher Cat #31985062) at a concentration of 0.3 μL RNAiMAX/10 μL Opti-MEM and incubated for 5 minutes at room temperature. After incubation, 10 μL/well was added to each well of 96-well collagen coated plates (BD Biocoat, Cat #356407), along with 10 μL/well of the appropriate dsRNA agent dilution, mixed gently and incubated for 20 minutes at room temperature. 80 μL of prepared cell suspension was added to each well to give final cell density of 15,000 cells/well and final dsRNA agent concentrations of 100 nM and 10 nM. Cells were incubated in a 37° C. incubator with 5% $CO_2$ for 16-22 hours. Cells were plated such that each experimental condition had 16 wells and the experiment was performed two times.

The ThermoFisher RNAqueous-96 Total RNA Isolation Kit was used to isolate RNA as per the protocol. Briefly, after 16-22 hours, the supernatant was aspirated from each well, 100 μL/well 1×DPBS was added to rinse away remaining media, then aspirated. 200 μL of Lysis/Binding Solution was added to each well in row 1 and row 5 of each plate, pipetted up and down several times, and transferred to the subsequent row such that 4 wells/condition were pooled to ensure adequate RNA recovery. This resulted in four replicates per condition. 100 μL 100% ethanol was added to each well of the culture plate containing lysates, mixed several times and transferred to the wells of the filter plate. Through a series of centrifugation steps (1,900×g, 1 minute) samples were washed with the provided wash solution, treated with DNase reagents, and eluted into 100 μL nuclease-free water. RNA concentration was determined with the NanoDrop 8000 Spectrophotometer (ThermoFisher).

RNA was further treated with TURBO DNase (Ambion). Each RNA sample (≤10 μg RNA/sample) was mixed with 2 μL DNase, 10 μL 10× buffer, and nuclease free water to a total volume of 100 μL, then incubated at 37° C. for 30 minutes. After DNase treatment, RNA was further purified with the RNeasy MinElute Cleanup Kit (Qiagen) as per the protocol. RNA was eluted in 30 μL nuclease free water, and the RNA concentration was determined with the NanoDrop 8000 Spectrophotometer. RNA was stored at −80° C. This RNA was subsequently used for cDNA library preparation with the TruSeq Stranded Total RNA Library Prep Kit (Illumina) and sequenced on the NextSeq500 desktop sequencer (Illumina), all according to manufacturers' instructions. Two experimental repeats were performed.

HepG2.2.15 cells were transfected in quadruplicate with 10 or 100 nM of AD-66810 or AD-81890 and cultured alongside untreated controls for 24 h. RNA extracted with the Purelink RNA kit (ThermoFisher) was used for cDNA library preparation with the TruSeq Stranded Total RNA Library Prep Kit with Ribo-Zero Human/Mouse/Rat for rRNA depletion (Illumina) and sequenced on the Next-Seq500 desktop sequencer (Illumina), all according to manufacturers' instructions. A total of 40 samples were pooled per NextSeq 500/550 High Output v2 (75 cycles) flow cell (Illumina). Two experimental repeats were performed.

Raw RNA-Seq reads were filtered with minimal mean quality scores of 25 and minimal remaining length of 36, using fastq-mcf. Filtered reads were simultaneously aligned to the Human (hg19/GRCh37) and HBV (GenBank nucleotide ID U95551; NCBI GeneID: 7276) genomes using STAR (version 2.4.2a). Due to the circular structure of the HBV genome, 46 base pairs were repeated at the end of a linearized version of the HBV sequence to allow for reads to map at the break point. Uniquely aligned reads mapping to exons were counted by featureCounts (version 1.5.0. All samples had >5M mapped reads. Differential gene expression analysis was performed in R (version 3.4.1) using the package DESeq2 (version 1.16.1). Multiple Testing Correction to obtain adjusted p-values was performed by DESeq2 using the method of Benjamini & Hochberg, 1995.

MA plots were used to visualize both on-target HBV knockdown and off-target effects. The analysis of GNA chemistry in mitigating global off-target effects was limited to downregulated genes (log 2 Fold Change <0). Upregulated genes (log 2 Fold Change >0) were considered secondary effects. Assessment of off-target effects was limited to the lowest (10 nM) dose since near maximal HBV knockdown was attained. To compare transcriptomic noise, genes that were significantly downregulated (adjusted p-value <0.05) were identified in AD-66810 and/or AD-81890. The extent of downregulation was visualized by a boxplot of log 2 Fold Change (FIG. 4), with statistical differences between AD-66810 and AD-81890 assessed using Welch's two-sided, two-sample t-test (Table 9).

Example 9

Evaluation of Human-Specific Hepatotoxicity in PXB-Mice

The PXB-mouse is a chimeric mouse with a humanized liver that is highly repopulated by human hepatocytes (PhoenixBio). The mouse is a urokinase-type plasminogen activator (uPA)/severe combined immunodeficiency (SCID) mice transplanted with human hepatocytes (humanized liver uPA/SCID mice) (Mercer et al., Nat. Med. 7:927-933, 2001). The reported humanized liver uPA/SCID mice has a replacement index (RI), the percent of human hepatocytes in the liver, of more than 70%. The mice can be used as a model for prediction of human drug metabolism, pharmacokinetics, and hepatotoxicity (Naritomi et al., Drug Metab Pharmacokinet. 33:31-39, 2018).

A study was performed in PBX-mice to compare hepatotoxicity of AD-66810 and AD-81890. Mice were dosed on Days 0, 21, 28, 35, and 42 with 12, 36, or 100 mg/kg of AD-66810, AD-81890, or PBS (control) by subcutaneous injection (n=4 per group). General condition observations and body weight measurement was performed twice per week through Day 49. Blood was collected by retro-orbital bleed twice weekly and serum was prepared using routine methods. A terminal bleed was performed, and animals were sacrificed by cardiac puncture and exsanguination. Necropsy was performed after exsanguination. The liver was harvested and weighed. Livers were divided for storage in RNAlater solution (Ambion), in formalin prior to paraffin embedding, and snap frozen.

All animals maintained body weight of more than 80% of the initial levels throughout the study period. In addition, the

TABLE 9

Statistical Testing of Significantly Downregulated Genes

| exp | dose | mean.AD-66810.lFC | mean.AD-81890.lFC | t.statistic | p.value | d.o.f. | N |
|---|---|---|---|---|---|---|---|
| 1 | 10 nM | −0.353 | −0.171 | −16.1 | 3.14E−52 | 1003 | 523 |
| 1 | 100 nM | −0.350 | −0.102 | −25.6 | 7.35E−123 | 1743 | 908 |
| 2 | 10 nM | −0.334 | −0.154 | −13.4 | 5.28E−37 | 757 | 391 |
| 2 | 100 nM | −0.314 | −0.179 | −13.1 | 1.35E−37 | 1693 | 858 | exp: experimental repeat;

Mean.AD-66810.lFC: Average $\log_2$ Fold Change of significantly downregulated genes in AD-66810 and/or AD-81890;

Mean.AD-81890.lFC: Average $\log_2$ Fold Change of significantly downregulated genes in AD-81890 and/or AD-66810;

t.statistic: t-statistic from Welch's two-sided, two-sample t-test;

p.value: p-value from Welch's two-sided, two-sample t-test;

d.o.f.: degrees of freedom;

N: Number of genes significantly downregulated (p < 0.05) in AD-66810 and/or AD-81890

Figure 4:
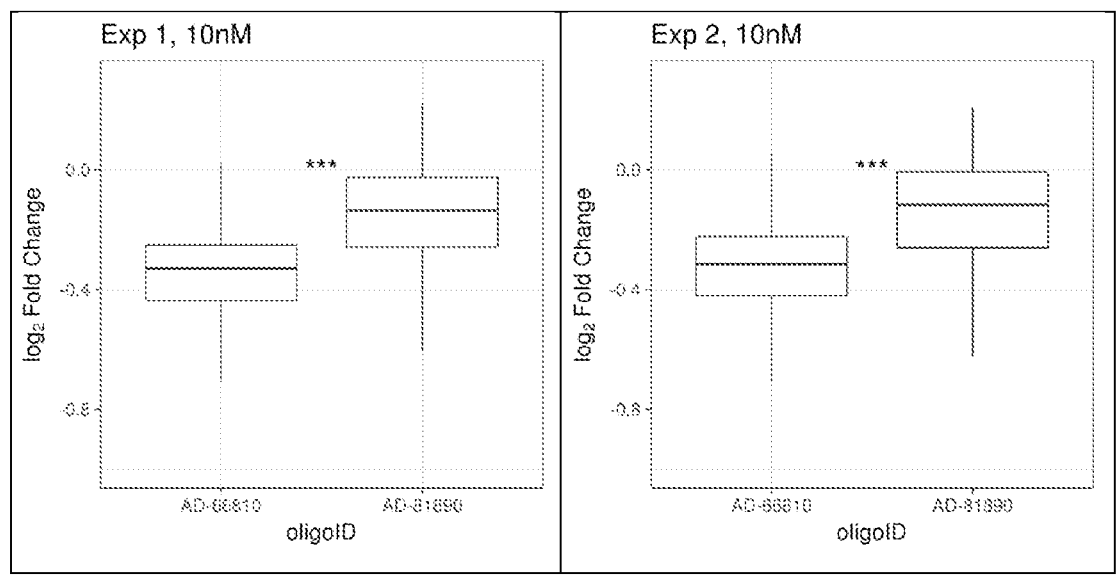
FIG. 4 shows boxplots showing log 2 Fold Change (treatment/control) for all genes that are significantly down-regulated (adjusted p-value <0.05, log 2 Fold Change <0) in AD-66810 or AD-81890. Thick horizontal lines represent median log 2 Fold Change, the vertical range of each box shows the interquartile range (IQR), and the whiskers extend to +/−1.58 IQR/sqrt(N), where N is the number of genes in each group. Statistical significance was assessed using Welch's two-sided, two-sample t-test.

Consistent reduction in the off-target effect with AD-81890 as compared to AD-66810 was observed across both experimental repeats (FIG. 4, Table 9). At 10 nM, AD-81890 showed a 52% (repeat 1) or 54% reduction (repeat 2) in the average log 2 Fold Change of the significantly downregulated genes as compared to AD-66810 (Table 9). At 100 nM, AD-81890 showed a 71% (repeat 1) or 43% reduction (repeat 2) in average log 2 Fold Change as compared to AD-66810 (Table 9). In all cases, the observed reduction in log 2 Fold Change was highly statistically significant. Therefore, AD-81890 had substantially lower levels of transcriptomic noise.

lowest arithmetic mean values of body weights in the compound-treated groups were higher than the control PBS-treated group.

Human serum albumin levels in blood were monitored throughout the course of the study. All surviving animals maintained blood h-Alb concentration of more than 7.0 mg/ml during the in-life phase of the study.

Figure 5A:
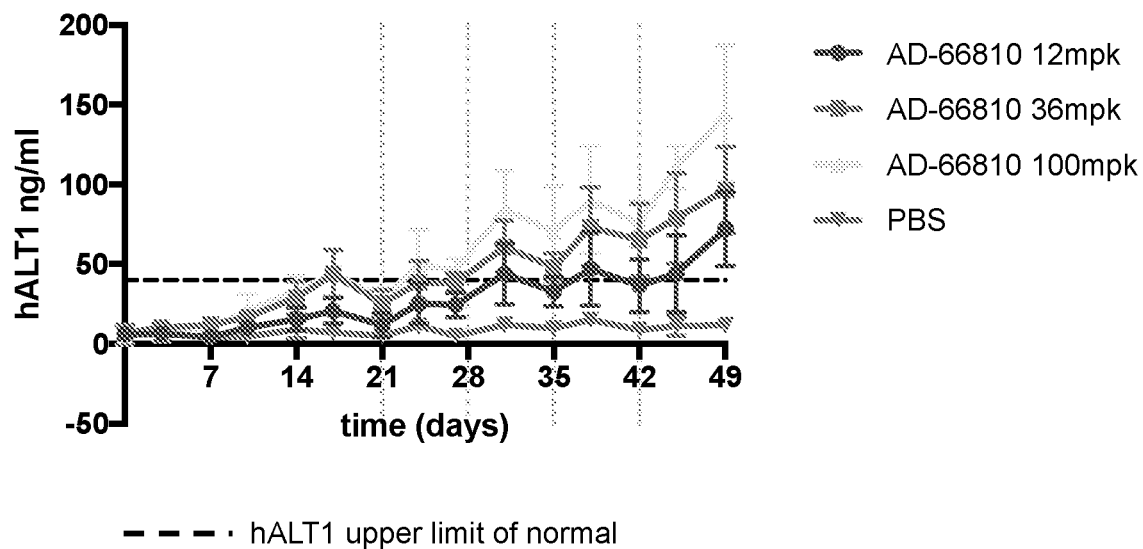
FIGS. 5A-5B show ALT levels in PXB-mice over time following administration of AD-66810 (FIG. 5A) or AD-81890 (FIG. 5B), relative to mice administered PBS.
Figure 5B:
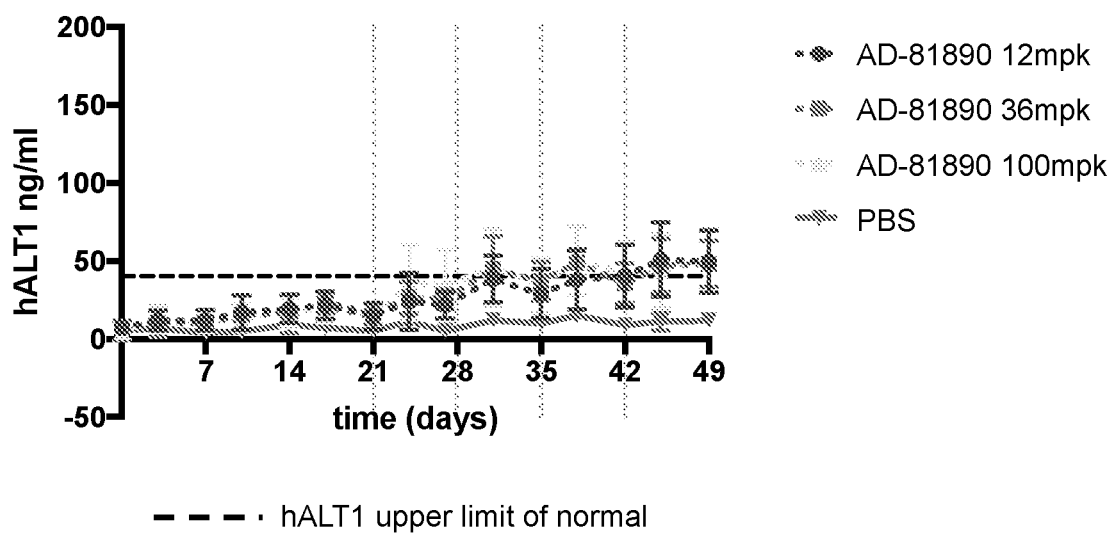

Liver enzymes were monitored throughout the course of the study. Specifically ALT, AST, ALP, GGT, TBIL, and TG were monitored throughout the study. The enzyme levels measured at day 49 for mice receiving AD-66810, AD-81890, or PBS are shown in Table 10 below. FIGS. 5A and 5B show ALT levels over time following administration of AD-66810 (FIG. 5A) or AD-81890 (FIG. 5B), relative to administration of PBS.

TABLE 10

Liver Enzyme Levels.

| Group | dsRNA agent | Dose (mg/kg) | ALT (U/L) | AST (U/L) | ALP (U/L) | GTT (U/L) | TBIL (U/L) | TG (U/L) |
|---|---|---|---|---|---|---|---|---|
| 1 | AD-66810 | 12 | 391 | 261 | 407 | 17 | 0.3 | 102 |
| 2 | AD-66810 | 36 | 505 | 293 | 398 | 22 | 0.2 | 85 |
| 3 | AD-66810 | 100 | 611 | 338 | 392 | 26 | 0.3 | 83 |
| 4 | AD-81890 | 12 | 293 | 210 | 375 | 13 | 0.3 | 95 |
| 5 | AD-81890 | 36 | 267 | 198 | 376 | 11 | 0.3 | 112 |
| 6 | AD-81890 | 100 | 330 | 237 | 410 | 14 | 0.2 | 103 |
| 7 | PBS | 0 | 139 | 146 | 329 | 10 | 0.2 | 110 |

For both test compound-treated groups, ALT, AST, ALP, and GGT showed an increase when compared with the control group. In addition, a dose-dependent change was demonstrated in ALT, AST, and GGT in the AD-66810-treated group.

In necropsy, there were no test compound-specific findings in either of the groups. When compared with the control group, there were no clear changes in relative (liver/body weight) liver weights of the animals in compound-treated groups.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

While specific embodiments have been illustrated and described, it will be readily appreciated that the various embodiments described above can be combined to provide further embodiments, and that various changes can be made therein without departing from the spirit and scope of the invention.

All of the Figures, U.S. patents, U.S. patent application publications, U.S. patent applications, foreign patents, foreign patent applications, and non-patent publications referred to in this specification or listed in the Application Data Sheet, including U.S. Provisional Patent application No. 62/718,314 filed Aug. 13, 2018 and International Application No. PCT/US2019/046142 filed Aug. 12, 2019, are incorporated herein by reference, in their entirety, unless otherwise stated. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim:

1. A double stranded ribonucleic acid (dsRNA) agent, comprising a sense strand and an antisense strand forming a double stranded region, wherein the antisense strand and the sense strand comprise the modified nucleotide sequences as set forth in, respectively:

(a)
(SEQ ID NO: 16)
5'-usGfsuga(Agn)gCfGfaaguGfcAfcacsusu-3'
and (SEQ ID NO: 29)
5'-gsusguGfcAfCfUfucgcuucaca-3';

(b)
(SEQ ID NO: 18)
5'-usGfsuga(Agn)gcgaaguGfdCAfcacsusu-3'
and (SEQ ID NO: 29)
5'-gsusguGfcAfCfUfucgcuucaca-3';

(c)
(SEQ ID NO: 20)
5'-usGfsudGa(Agn)gCfGfaaguGfcAfcacsusu-3'
and (SEQ ID NO: 29)
5'-gsusguGfcAfCfUfucgcuucaca-3';

(d)
(SEQ ID NO: 23)
5'-usGfsudGadAgdCGfaaguGfcAfcacsusu-3'
and (SEQ ID NO: 29)
5'-gsusguGfcAfCfUfucgcuucaca-3';

(e)
(SEQ ID NO: 24)
5'-usGfsuga(Agn)dGCfGfaaguGfcAfcacsusu-3'
and (SEQ ID NO: 29)
5'-gsusguGfcAfCfUfucgcuucaca-3';

(f)
(SEQ ID NO: 25)
5'-usGfsudGadAgdCGfaaguGfcAfdCacsusu-3'
and (SEQ ID NO: 29)
5'-gsusguGfcAfCfUfucgcuucaca-3';
or (g)
(SEQ ID NO: 28)
5'-usGfsuga(Agn)gCfGfaaguGfdCAfcacsusu-3'
and (SEQ ID NO: 29)
5'-gsusguGfcAfCfUfucgcuucaca-3';

wherein a, c, g, and u are 2'-O-methyladenosine-3'-phosphate, 2'-O-methylcytidine-3'-phosphate, 2'-O-methylguanosine-3'-phosphate, and 2'-O-methyluridine-3'-phosphate, respectively;

Af, Cf, Gf, and Uf are 2'-fluoroadenosine-3'-phosphate, 2'-fluorocytidine-3'-phosphate, 2'-fluoroguanosine-3'-phosphate, and 2'-fluorouridine-3'-phosphate, respectively;

dA, dC, dG, and dT are 2'-deoxyadenosine-3'-phosphate, 2'-deoxycytidine-3'-phosphate, 2'-deoxyguanosine-3'-phosphate, and 2'-deoxythymidine-3'-phosphate, respectively;

(Agn) is adenosine-glycol nucleic acid (GNA); and s is a phosphorothioate linkage.

2. The dsRNA agent of claim 1, wherein at least one strand comprises a 3' overhang of at least 1 nucleotide.

3. The dsRNA agent of claim 1, wherein the double stranded region is 19-21 nucleotide pairs in length.

4. The dsRNA agent of claim 1, wherein each strand independently has 19-23 nucleotides.

5. The dsRNA agent of claim 1, further comprising a ligand.

6. The dsRNA agent of claim 5, wherein the ligand is conjugated to the 3' end of the sense strand of the dsRNA agent.

7. The dsRNA agent of claim 6, wherein the ligand is an N-acetylgalactosamine (GalNAc) derivative.

8. The dsRNA agent of claim 7, wherein the ligand is

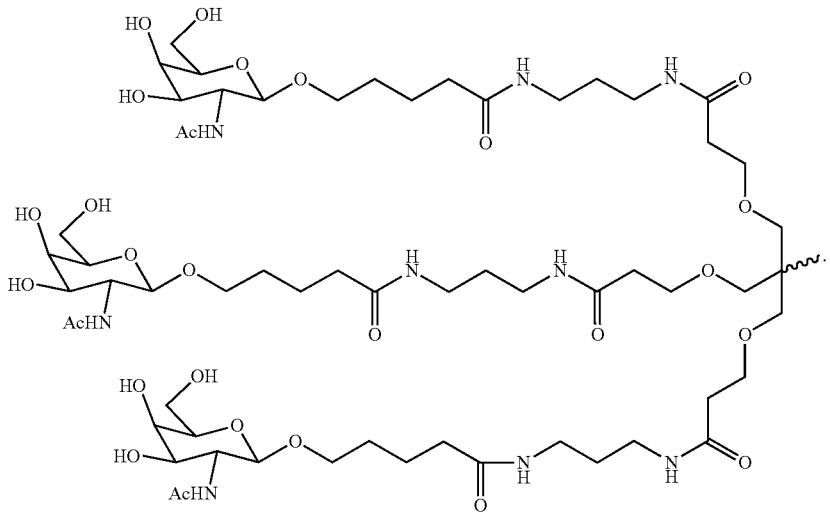 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

9. The dsRNA agent of claim 8, wherein the ligand is conjugated to the 3' end of the sense strand of the dsRNA agent according to the following structure:

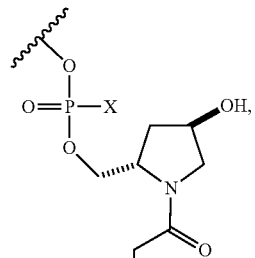
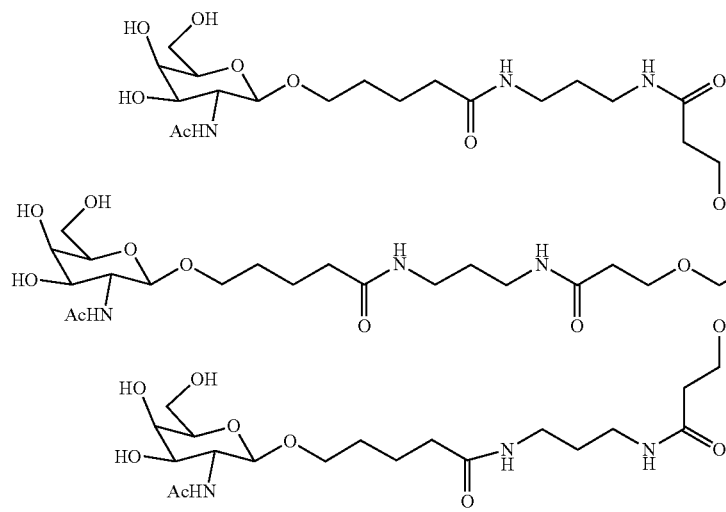

wherein X is O or S.

10. The dsRNA agent of claim 9, wherein the X is O.

11. The dsRNA agent of claim 1, wherein the antisense strand and the sense strand consist of the modified nucleotide sequences as set forth in, respectively:

(a)
```
                                        (SEQ ID NO: 16)
5'-usGfsuga(Agn)gCfGfaaguGfcAfcacsusu-3'
and (SEQ ID NO: 10)
5'-gsusguGfcAfCfUfucgcuucacaL96-3';
```

(b)
```
                                        (SEQ ID NO: 18)
5'-usGfsuga(Agn)gcgaaguGfdCAfcacsusu-3'
and (SEQ ID NO: 10)
5'-gsusguGfcAfCfUfucgcuucacaL96-3';
```

(c)
```
                                        (SEQ ID NO: 20)
5'-usGfsudGa(Agn)gCfGfaaguGfcAfcacsusu-3'
and (SEQ ID NO: 10)
5'-gsusguGfcAfCfUfucgcuucacaL96-3';
```

(d)
```
                                        (SEQ ID NO: 23)
5'-usGfsudGadAgdCGfaaguGfcAfcacsusu-3'
and (SEQ ID NO: 10)
5'-gsusguGfcAfCfUfucgcuucacaL96-3';
```

(e)
```
                                        (SEQ ID NO: 24)
5'-usGfsuga(Agn)dGCfGfaaguGfcAfcacsusu-3'
and (SEQ ID NO: 10)
5'-gsusguGfcAfCfUfucgcuucacaL96-3';
```

(f)
```
                                        (SEQ ID NO: 25)
5'-usGfsudGadAgdCGfaaguGfcAfdCacsusu-3'
and (SEQ ID NO: 10)
5'-gsusguGfcAfCfUfucgcuucacaL96-3';
or
```

(g)
```
                                        (SEQ ID NO: 28)
5'-usGfsuga(Agn)gCfGfaaguGfdCAfcacsusu-3'
and (SEQ ID NO: 10)
5'-gsusguGfcAfCfUfucgcuucacaL96-3';
``` wherein a, c, g, and u are 2'-O-methyladenosine-3'-phosphate, 2'-O-methylcytidine-3'-phosphate, 2'-O-methylguanosine-3'-phosphate, and 2'-O-methyluridine-3'-phosphate, respectively;

Af, Cf, Gf, and Uf are 2'-fluoroadenosine-3'-phosphate, 2'-fluorocytidine-3'-phosphate, 2'-fluoroguanosine-3'-phosphate, and 2'-fluorouridine-3'-phosphate, respectively;

dA, dC, dG, and dT are 2'-deoxyadenosine-3'-phosphate, 2'-deoxycytidine-3'-phosphate, 2'-deoxyguanosine-3'-phosphate, and 2'-deoxythymidine-3'-phosphate, respectively;

(Agn) is adenosine-glycol nucleic acid (GNA);

s is a phosphorothioate linkage; and

L96 is N-[tris(GalNAc-alkyl)-amidodecanoyl)]-4-hydroxyprolinol.

12. The dsRNA agent of claim 1, wherein the antisense strand and the sense strand consist of the modified nucleotide sequences as set forth in, respectively:

```
                                      (SEQ ID NO: 16)
5'-usGfsuga(Agn)gCfGfaaguGfcAfcacsusu-3'
and
                                      (SEQ ID NO: 10)
5'-gsusguGfcAfCfUfucgcuucacaL96-3';
``` wherein a, c, g, and u are 2'-O-methyladenosine-3'-phosphate, 2'-O-methylcytidine-3'-phosphate, 2'-O-methylguanosine-3'-phosphate, and 2'-O-methyluridine-3'-phosphate, respectively;

Af, Cf, Gf, and Uf are 2'-fluoroadenosine-3'-phosphate, 2'-fluorocytidine-3'-phosphate, 2'-fluoroguanosine-3'-phosphate, and 2'-fluorouridine-3'-phosphate, respectively;

dA, dC, dG, and dT are 2'-deoxyadenosine-3'-phosphate, 2'-deoxycytidine-3'-phosphate, 2'-deoxyguanosine-3'-phosphate, and 2'-deoxythymidine-3'-phosphate, respectively;

(Agn) is adenosine-glycol nucleic acid (GNA);

s is a phosphorothioate linkage; and

L96 is N-[tris(GalNAc-alkyl)-amidodecanoyl)]-4-hydroxyprolinol.

13. An isolated cell containing the dsRNA agent of claim 1.

14. A pharmaceutical composition comprising the dsRNA agent of claim 1 and a pharmaceutical excipient.

15. A method of inhibiting HBV gene expression or inhibiting replication of a HBV in a cell, the method comprising contacting the cell with the dsRNA agent of claim 1.

16. The method of claim 15, wherein the cell is within a human subject.

17. The method of claim 15, wherein the cell is in vitro.

18. A method of reducing the level of a Hepatitis B virus (HBV) antigen or reducing the viral load of HBV in a subject infected with HBV, comprising administering to the subject a therapeutically effective amount of the dsRNA agent of claim 1.

19. The method of claim 18, wherein the HBV antigen is HBsAg or HBeAg.

20. The method of claim 18, wherein the subject is HBeAg positive.

21. The method of claim 18, wherein the subject is HBeAg negative.

22. A method of treating a subject having a HBV infection, comprising administering to the subject a therapeutically effective amount of the dsRNA agent of claim 1, thereby treating the subject.

23. A method of treating a subject having a HBV-associated disorder, comprising administering to the subject a therapeutically effective amount of the dsRNA agent of claim 1, thereby treating the subject.

24. The method of claim 23, wherein the HBV-associated disorder is chronic hepatitis and the subject is HBeAg positive.

25. The method of claim 23, wherein the HBV-associated disorder is chronic hepatitis and the subject is HBeAg negative.

26. The method of claim 23, wherein the HBV-associated disorder is hepatitis D virus (HDV) infection.

27. The method of claim 22, wherein the dsRNA agent comprises a antisense strand comprising the modified nucleotide sequence as set forth in 5'-usGfsuga(Agn)gCfGfaaguGfcAfcacsusu-3' (SEQ ID NO:16), and a sense strand comprising the modified nucleotide sequence as set forth in 5'-gsusguGfcAfCfUfucgcuucacaL96-3' (SEQ ID NO:10);

wherein a, c, g, and u are 2'-O-methyladenosine-3'-phosphate, 2'-O-methylcytidine-3'-phosphate, 2'-O-methylguanosine-3'-phosphate, and 2'-O-methyluridine-3'-phosphate, respectively;

Af, Cf, Gf, and Uf are 2'-fluoroadenosine-3'-phosphate, 2'-fluorocytidine-3'-phosphate, 2'-fluoroguanosine-3'-phosphate, and 2'-fluorouridine-3'-phosphate, respectively;

dA, dC, dG, and dT are 2'-deoxyadenosine-3'-phosphate, 2'-deoxycytidine-3'-phosphate, 2'-deoxyguanosine-3'-phosphate, and 2'-deoxythymidine-3'-phosphate, respectively;

(Agn) is adenosine-glycol nucleic acid (GNA);

s is a phosphorothioate linkage; and

L96 is N-[tris(GalNAc-alkyl)-amidodecanoyl)]-4-hydroxyprolinol.

28. The method of claim 23, wherein the dsRNA agent comprises a antisense strand comprising the modified nucleotide sequence as set forth in 5'-usGfsuga(Agn)gCfGfaaguGfcAfcacsusu-3' (SEQ ID NO:16), and a sense strand comprising the modified nucleotide sequence as set forth in 5'-gsusguGfcAfCfUfucgcuucacaL96-3' (SEQ ID NO:10);

wherein a, c, g, and u are 2'-O-methyladenosine-3'-phosphate, 2'-O-methylcytidine-3'-phosphate, 2'-O-methylguanosine-3'-phosphate, and 2'-O-methyluridine-3'-phosphate, respectively;

Af, Cf, Gf, and Uf are 2'-fluoroadenosine-3'-phosphate, 2'-fluorocytidine-3'-phosphate, 2'-fluoroguanosine-3'-phosphate, and 2'-fluorouridine-3'-phosphate, respectively;

dA, dC, dG, and dT are 2'-deoxyadenosine-3'-phosphate, 2'-deoxycytidine-3'-phosphate, 2'-deoxyguanosine-3'-phosphate, and 2'-deoxythymidine-3'-phosphate, respectively;

(Agn) is adenosine-glycol nucleic acid (GNA);

s is a phosphorothioate linkage; and

L96 is N-[tris(GalNAc-alkyl)-amidodecanoyl)]-4-hydroxyprolinol.

29. The method of claim 28 wherein the HBV-associated disorder is chronic hepatitis and the subject is HBeAg positive.

30. The method of claim 28, wherein the HBV-associated disorder is chronic hepatitis and the subject is HBeAg negative.

31. The method of claim 28, wherein the HBV-associated disorder is hepatitis D virus (HDV) infection.

32. The method of claim 22, wherein the dsRNA agent comprises a antisense strand consisting of the modified nucleotide sequence as set forth in 5'-usGfsuga(Agn)gCfGfaaguGfcAfcacsusu-3' (SEQ ID NO:16), and a sense strand consisting of the modified nucleotide sequence as set forth in 5'-gsusguGfcAfCfUfucgcuucacaL96-3' (SEQ ID NO:10);

wherein a, c, g, and u are 2'-O-methyladenosine-3'-phosphate, 2'-O-methylcytidine-3'-phosphate, 2'-O-methylguanosine-3'-phosphate, and 2'-O-methyluridine-3'-phosphate, respectively;

Af, Cf, Gf, and Uf are 2'-fluoroadenosine-3'-phosphate, 2'-fluorocytidine-3'-phosphate, 2'-fluoroguanosine-3'-phosphate, and 2'-fluorouridine-3'-phosphate, respectively;

dA, dC, dG, and dT are 2'-deoxyadenosine-3'-phosphate, 2'-deoxycytidine-3'-phosphate, 2'-deoxyguanosine-3'-phosphate, and 2'-deoxythymidine-3'-phosphate, respectively;

(Agn) is adenosine-glycol nucleic acid (GNA);

s is a phosphorothioate linkage; and

L96 is N-[tris(GalNAc-alkyl)-amidodecanoyl)]-4-hydroxyprolinol.

33. The method of claim 23, wherein the dsRNA agent comprises a antisense strand consisting of the modified nucleotide sequence as set forth in 5'-usGfsuga(Agn)gCfGfaaguGfcAfcacsusu-3' (SEQ ID NO:16), and a sense strand consisting of the modified nucleotide sequence as set forth in 5'-gsusguGfcAfCfUfucgcuucacaL96-3' (SEQ ID NO:10);

wherein a, c, g, and u are 2'-O-methyladenosine-3'-phosphate, 2'-O-methylcytidine-3'-phosphate, 2'-O-methylguanosine-3'-phosphate, and 2'-O-methyluridine-3'-phosphate, respectively;

Af, Cf, Gf, and Uf are 2'-fluoroadenosine-3'-phosphate, 2'-fluorocytidine-3'-phosphate, 2'-fluoroguanosine-3'-phosphate, and 2'-fluorouridine-3'-phosphate, respectively;

dA, dC, dG, and dT are 2'-deoxyadenosine-3'-phosphate, 2'-deoxycytidine-3'-phosphate, 2'-deoxyguanosine-3'-phosphate, and 2'-deoxythymidine-3'-phosphate, respectively;

(Agn) is adenosine-glycol nucleic acid (GNA);

s is a phosphorothioate linkage; and

L96 is N-[tris(GalNAc-alkyl)-amidodecanoyl)]-4-hydroxyprolinol.

34. The method of claim 33 wherein the HBV-associated disorder is chronic hepatitis and the subject is HBeAg positive.

35. The method of claim 33, wherein the HBV-associated disorder is chronic hepatitis and the subject is HBeAg negative.

36. The method of claim 33, wherein the HBV-associated disorder is hepatitis D virus (HDV) infection.

* * * * *